US009487479B2

(12) United States Patent
Sadar et al.

(10) Patent No.: US 9,487,479 B2
(45) Date of Patent: Nov. 8, 2016

(54) SMALL MOLECULE INHIBITORS OF N-TERMINUS ACTIVATION OF THE ANDROGEN RECEPTOR

(75) Inventors: Marianne D. Sadar, West Vancouver (CA); Nasrin R. Mawji, Burnaby (CA); Jun Wang, New Westminster (CA); Raymond J. Andersen, Vancouver (CA); David E. Williams, Vancouver (CA); Mike Leblanc, Vancouver (CA); Lu-Ping Yan, Vancouver (CA)

(73) Assignees: The University of British Columbia, Vancouver, BC (CA); British Columbia Cancer Agency Branch, Vancouver, BC (CA)

( * ) Notice: Subject to any disclaimer, the term of this patent is extended or adjusted under 35 U.S.C. 154(b) by 1563 days.

(21) Appl. No.: 12/999,035

(22) PCT Filed: Aug. 24, 2009

(86) PCT No.: PCT/CA2009/001173
§ 371 (c)(1),
(2), (4) Date: May 31, 2011

(87) PCT Pub. No.: WO2010/020055
PCT Pub. Date: Feb. 25, 2010

(65) Prior Publication Data
US 2011/0230539 A1    Sep. 22, 2011

Related U.S. Application Data

(60) Provisional application No. 61/136,277, filed on Aug. 22, 2008.

(51) Int. Cl.
*C07D 207/38* (2006.01)
*A61K 31/495* (2006.01)

(52) U.S. Cl.
CPC ........... *C07D 207/38* (2013.01); *A61K 31/495* (2013.01)

(58) Field of Classification Search
None
See application file for complete search history.

(56) References Cited

U.S. PATENT DOCUMENTS

| 2008/0057068 A1 | 3/2008 | Dalton et al. |
| 2015/0344424 A1 | 12/2015 | Yan et al. |

FOREIGN PATENT DOCUMENTS

| JP | 03017057 A * | 1/1991 |
| WO | 00/01813 A2 | 1/2000 |
| WO | WO 2010/020055 A1 | 2/2010 |

OTHER PUBLICATIONS

Kostochka, et al., Pharmaceutical Chemistry Journal, 23:291 (1989).*
Fahey, et al., J. Chem. Ecol., 28:1773 (2002).*
Kricheldorf, H., Makromol. Chem. 178:905 (1977).*
Lu, et al., J. Nat. Prod., 61:1096 (1998).*
Sadar, et al., "Sintokamides A to E, Chlorinated Peptides from the Sponge *dysidea* sp. that Inhibit Transactivation of the N-Terminus of the Androgen Receptor in Prostate Cancer Cells," Org. Lett., 2008, 10(21), pp. 4947-4950.
Zarantonello et al., "Total Synthesis and Semi-Synthetic Approaches to Analogues of Antibacterial Natural Product Althiomycin," Bioorg. Med. Chem. Lett., 2002, 2, pp. 561-565.
Simmons et al., "Belamide A, a new antimitotic tetrapeptide from a Panamanian marine cyanobacterium," Tetrahedron Lett., 2006, 47, pp. 3387-3390.
Bisson et al., "Discovery of antiandrogen activity of nonsteroidal scaffolds of marketed drugs," PNAS 104(29):11927-11932, 2007.
Blaszczyk et al., "Osteoblast-Derived Factors Induce Androgen-Independent Proliferation and Expression of Prostate-Specific Antigen in Human Prostate Cancer Cells," Clinical Cancer Research 10:1860-1869, 2004.
Chang et al., "Development of Peptide Antagonists for the Androgen Receptor Using Combinatorial Peptide Phage Display," Molecular Endocrinology 19(10):2478-2490, 2005.
Dehm et al., "Selective Role of an $NH_2$-Terminal WxxLF Motif for Aberrant Androgen Receptor Activation in Androgen Depletion-Independent Prostate Cancer Cells," Cancer Research 67(20):10067-10077, 2007.
Estébanez-Perpiñáet al., "A surface on the androgen receptor that allosterically regulates coactivator binding," PNAS 104(41):16074-16079, 2007.
Estébanez-Perpiñáet al., "The Molecular Mechanisms of Coactivator Utilization in Ligand-dependent Transactivation by the Androgen Receptor," Journal of Biological Chemistry 280:8060-8068, 2005.
Gleave et al., "Acceleration of Human Prostate Cancer Growth in Vivo by Factors Produced by Prostate and Bone Fibroblasts," Cancer Research 51:3753-3761, 1991.
Gregory et al., "Epidermal Growth Factor Increases Coactivation of the Androgen Receptor in Recurrent Prostate Cancer," The Journal of Biological Chemistry 279(8):7119-7130, 2004.
Horoszewicz et al., "LNCaP Model of Human Prostatic Carcinoma," Cancer Research 43:1809-1818, 1983.
Hur et al., "Recognition and Accommodation at the Androgen Receptor Coactivator Binding Interface," PLoS Biology 2(9): 1303-1312, 2004.
Nazareth et al., "Activation of the Human Androgen Receptor through a Protein Kinase A Signaling Pathway," The Journal of Biological Chemistry 271(33):19900-19907, 1996.
Quayle et al., "Androgen receptor decoy molecules block the growth of prostate cancer," PNAS 104(4):1331-1336, 2007.
Sadar, "Androgen-independent Induction of Prostate-specific Antigen Gene Expression via Cross-talk between the Androgen Receptor and Protein Kinase A Signal Transduction Pathways," The Journal of Biological Chemistry 274(12):7777-7783, 1999.
Sadar, "Characterization of a New in Vivo Hollow Fiber Model for the Study of Progression of Prostate Cancer to Androgen Independence," Molecular Cancer Therapeutics 1:629-637, 2002.
Sato et al., "Intermittent Androgen Suppression Delays Progression to Androgen-independent Regulation of Prostate-specific Antigen Gene in the LNCaP Prostate Tumour model," J. Steriod Biochem. Molec. Biol. 58(2):139-146, 1996.

(Continued)

Primary Examiner — Michael Barker
(74) Attorney, Agent, or Firm — Cooley LLP

(57) ABSTRACT

Compounds having a structure of Formula (A) are provided. Uses of such compounds for treatment of various indications, including prostate cancer as well as methods of treatment involving such compounds are provided. Uses of compounds having a structure of Formula (F) for treatment of various indications, including prostate cancer as well as methods of treatment involving such compounds are also provided.

54 Claims, 6 Drawing Sheets

(56) References Cited

OTHER PUBLICATIONS

Sato et al., "A Metastatic and Androgen-sensitive Human Prostate Cancer Model Using Intraprostatic Inoculation of LNCaP Cells in SCID Mice," Cancer Research 57:1584-1589, 1997.
Taplin et al., "Selection for Androgen Receptor Mutations in Prostate Cancers Treated with Androgen Antagonist," Cancer Research 59:2511-2515, 1999.
Ueda et al., "Ligand-independent Activation of the Androgen Receptor by Interleukin-6 and the Role of Steroid Receptor Coactivator-1 in Prostate Cancer Cells," The Journal of Biological Chemistry 277(41):38087-38094, 2002.
Ueda et al., "Activation of the Androgen Receptor N-terminal Domain by Interleukin-6 via MAPK and STAT3 Signal Transduction Pathways," The Journal of Biological Chemistry 277(9):7076-7085, 2002.
Berge, S.M. et al., "Pharmaceutical Salts." Pharmaceutical Sciences, 66(1):1-19 (1977).
Brantley et al., "Synthetic studies of trichloroleucine marine natural products. Michael addition of LiCCl3 to N-crotonylcamphor sultam." Organic Letters, 1(13): 2165-2167 (1999).
Bruckheimer, E.M. et al., "Apoptosis in prostate carcinogenesis A growth regulator and a therapeutic target." Cell Tissue Res, 301:153-162 (2000).
CAS Registry No. 88274-93-5, entered STN Nov. 16, 1984.
Clinton and Hua, "Estrogen action in human ovarian cancer." Critical Reviews in Oncology/Hematology, 25:1-9 (1997).
Culig, Zoran et al., "Androgen Receptor Activation in Prostatic Tumor Cell Lines by Insulin-like Growth Factor-I, Keratinocyte Growth Factor, and Epidermal Growth Factor." Cancer Research, 54:5474-5478 (1994).
Dehm, S. et al., "Ligand-independent Androgen Receptor Activity is Activation Function-2-independent and Resistant to Antiandrogens in Androgen Refractory Prostate Cancer Cells." The Journal of Biological Chemistry, 281(38):27882-27893 (2006).
Dehm, S. et al., "Splicing of a Novel Androgen Receptor Exon Generates a Constitutively Active Androgen Receptor that Mediates Prostate Cancer Therapy Resistance." Cancer Research, 68:5469-5477 (2008).
Edmondson, J. M. et al., "The human ovarian surface epithelium is an androgen responsive tissue." British Journal of Cancer, 86:879-885 (2002).
Erickson and Wells, "New polychlorinated metabolites from a Barrier Reef collection of the sponge Dysidea herbacea." Australian Journal of Chemistry, 35(1): 31-38 (1982).
European Application No. EP 09807798.5, Extended European Search Report dated May 8, 2012.
Guinan, P.D. et al., "Impotence Therapy and Cancer of the Prostate." The American Journal of Surgery, 131:599-600 (1976).
Guo, Zhiyong et al., "A Novel Androgen Receptor Splice Variant Is Up-regulated during Prostate Cancer Progression and Promotes Androgen Depletion-Resistant Growth." Cancer Research, 69:2305-13 (2009).
He, B. et al., "Structural Basis for Androgen Receptor Interdomain and Coactivator Interactions Suggests a Transition in Nuclear Receptor Activation Function Dominance." Molecular Cell, 16:425-438 (2004).
Helzlsouer, Kathy J., et al., "Serum Gonadotropins and Steroid Hormones and the Development of Ovarian Cancer." JAMA, 274(24):1926-1930 (1995).
Hofheinz and Oberhansli, "Dysidin, a novel chlorine containing natural product from the spong Dysidea herbacea", Helv. Chim. Acta, 60: 660-669 (1977) (with English Summary).
Hu, R. et al., "Ligand-Independent Androgen Receptor Variants Derived from Splicing of Cryptic Exons Signify Hormone-Refractory Prostate Cancer." Cancer Research, 69:16-22 (2009).
Huber, P.R. et al., "Prostate Specific Antigen. Experimental and Clinical Observations." Scand. J. Urol Nephrol., 104:33-39 (1987).
Isaacs, J.T., "Antagonistic Effect of Androgen on Prostatic Cell Death." The Prostate, 5:545-557 (1984).
Jackson, J. A. et al., "Prostatic Complications of Testosterone Replacement Therapy." Arch Intern Med., 149:2365-2366 (1989).
Jenster, G. et al., "Domains of the Human Androgen Receptor Involved in Steroid Binding, Transcriptional Activation, and Subcellular Localization." Molecular Endocrinology, 5:1396-1404 (1991).
Kaighn, M.E. et al., "Prostate Carcinoma: Tissue Culture Cell Lines." National Cancer Institute Monograph, 49:17-21 (1978).
Kim, D. et al., "Androgen Receptor Expression and Cellular Proliferation During Transition from Androgen-Dependent to Recurrent Growth after Castration in the CWR22 Prostate Cancer Xenograft." American Journal of Pathology, 160(1):219-226 (2002).
Kazlauskas et al., "A new sesquiterpene from the sponge Dysidea herbacea." Tetrahedron Letters, 19 (Issue 49): 4949-4950 (1978).
Kazlauskas et al., "Two sesquiterpene furans with new carbocyclic ring systems and related thiol acetates from a species of the sponge genus." Tetrahedron Letters, 19 (Issue 49): 4951-4954 (1978).
Miller, J.I. et al., "The Clinical Usefulness of Serum Prostate Specific Antigen After Hormonal Therapy of Metastatic Prostate Cancer." The Journal of Urology, 147:956-961 (1992).
Noble, R. L., "The development of prostatic adenocarcinoma in Nb Rats following prolonged sex hormone administration." Cancer Research, 37:1929-1933 (1977).
Noble, R. L., "Sex steroids as a cause of adenocarcinoma of the dorsal prostate in Nb Rats, and their influence on the growth of transplants." Oncology, 34:138-141 (1977).
Orjala et al., "Barbamide, a chlorinated metabolite with molluscicidal activity from the Caribbean cyanobacterium Lyngbya majuscula." Journal of Natural Products, 59(4): 427-430 (1996).
PCT/CA2009/001173, International Search Report and Written Opinion dated Dec. 7, 2009.
PCT/CA2009/001173, International Preliminary Report on Patentability dated Feb. 22, 2011.
PCT/US2015/033385, International Search Report and Written Opinion dated Aug. 28, 2015.
Rao and Slotman, "Endocrine Factors in Common Epithelial Ovarian Cancer." Endocrine Reviews, 12(1):14-26 (1991).
Reid, J. et al., "Conformational Analysis of the Androgen Receptor Amino-terminal Domain Involved in Transactivation." The Journal of Biological Chemistry, 277:20079-20086 (2002).
Risch, H.A., "Hormonal Etiology of Epithelial Ovarian Cancer, With a Hypothesis Concerning the Role of Androgens and Progesterone." Journal of the National Cancer Institute, 90(23):1774-1786 (1998).
Roberts, J. T. et al., "Adenocarcinoma of Prostate in 40-Year-Old Body-Builder." Lancet, 2:742 (1986).
Ross, R.K. et al., "Androgen Metabolism and Prostate Cancer: Establishing a Model of Genetic Susceptibility." European Urology, 35:355-361 (1999).
Sadar, M. et al., "Prostate cancer: molecular biology of early progression to androgen independence." Endocrine-Related Cancer, 6:487-502 (1999).
Snoek, R. et al., "Induction of Cell-free, In Vitro Transcription by Recombinant Androgen Receptor Peptides." J. Steroid Biochem. Mol. Biol., 59:243-250 (1996).
Still, W. C. et al., "Rapid Chromatographic Technique for Preparative Separations with Moderate Resolution." J. Org. Chem., 43(14):2923-2925 (1978).
Su, Jing-Yu, et al. "Three new diketopiperazines from a marine sponge Dysidea fragilis." Journal of Natural Products, 56(4): 637-642 (1993).
Sun, S. et al., "Castration resistance in human prostate cancer is conferred by a frequently occurring androgen receptor splice variant." The Journal of Clinical Investigation, 120(8):2715-2730 (2010).
Tanji, N. et al., "Growth Factors: Rules in Andrology." Archives of Andrology, 47:1-7 (2001).
Thomson, A.A., "Role of androgens and fibroblast growth factors in prostatic development." Reproduction, 121:187-195 (2001).

(56) References Cited

OTHER PUBLICATIONS

Ueda, T. et al., "Activation of the Androgen Receptor N-terminal Domain by Interleukin-6 via MAPK and STAT3 Signal Transduction Pathways." The Journal of Biological Chemistry, 277(9):7076-7085 (2002).

Van Der Kwast, T.H. et al., "Androgen Receptors in Endocrine-Therapy-Resistant Human Prostate Cancer." Inter. J. Cancer, 48:189-193 (1991).

Wilding, G., "The Importance of Steroid Hormones in Prostate Cancer." Cancer Surveys, 14:113-130 (1992).

Willard et al., "Total synthesis of (.+−.)-dysidin, a marine metabolite containing an N-acyl-O-methyltetramic acid." The Journal of Organic Chemistry, 49(19): 3489-3493 (1984).

Wilson, J.D. et al., "Long-Term Consequences of Castration in Men: Lessons from the Skoptzy and the Eunuchs of the Chinese and Ottoman Courts." The Journal of Clinical Endocrinology & Metabolism, 84:4324-4331 (1999).

Hosseini et al., "Dipeptide Analogues Containing 4-Ethoxy-3-pyrrolin-2-ones," *Organic Letters* 8(10):2103-2106 (2006).

Hosseini et al., "Pyrrolidinone-modified di- and tripeptides: highly diastereoselective preparation and investigation of their stability," *Organic & Biomolecular Chemistry* 5:3486-3494 (2007).

Jin et al., "Total Synthesis of Sintokamide C," *Organic Letters* 12(5):1100-1103 (2010).

Luesch et al., "Structurally diverse new alkaloids from Palauan collections of the apratoxin-producing marine cyanobacterium *Lyngbya* sp.," *Tetrahedron* 58:7959-7966 (2002).

Unson et al., "New Polychlorinated Amino Acid Derivatives from the Marine Sponge *Dysidea herbacea*," *J. Org. Chem.* 58:6336-6343 (1993).

Williams and Lemke, *Foye's Principles of Medicinal Chemistry*, Fifth Edition (14 Pages) (2002).

\* cited by examiner 06-80: 138.9 +/- 46.9 RLU
Approximately 90% inhibition

CB3.1                    R1881

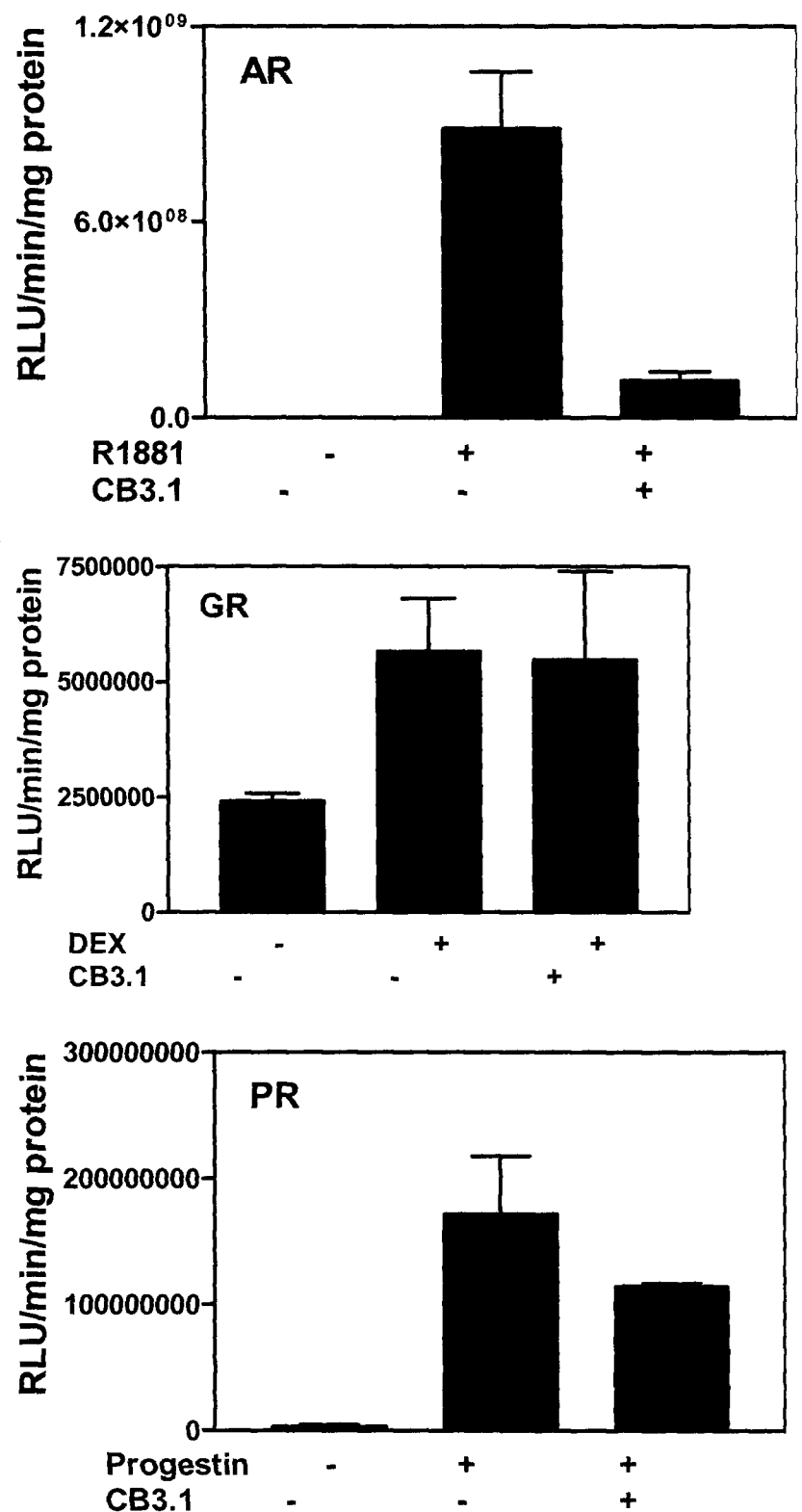
FIGURES 2A-C

FIGURE 6
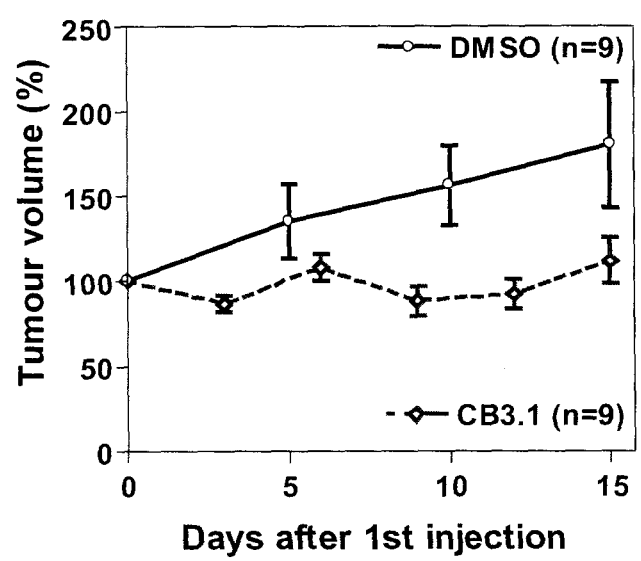

SMALL MOLECULE INHIBITORS OF N-TERMINUS ACTIVATION OF THE ANDROGEN RECEPTOR

CROSS REFERENCE TO RELATED APPLICATIONS

This application is a National Stage Entry of PCT/CA2009/001173, filed on Aug. 24, 2009, which claims the benefit of U.S. Provisional Patent Application Ser. No. 61/136,277 entitled "SMALL MOLECULE INHIBITORS OF N-TERMINUS ACTIVATION OF THE ANDROGEN RECEPTOR" filed on Aug. 22, 2008, the disclosures of which are incorporated herein by reference in their entirety.

STATEMENT REGARDING FEDERALLY SPONSORED RESEARCH

This invention was made in part with government support under grant number W81XWH-05-1-0058 (PC040768), awarded by U.S. Army Medical Research and Materiel Command. The United States government may have certain rights in the invention.

TECHNICAL FIELD

This invention relates to therapeutics, their uses and methods for the treatment of various indications, including various cancers. In particular the invention relates to therapies and methods of treatment for cancers such as prostate cancer, including all stages and androgen dependent, androgen-sensitive and androgen-independent (also referred to as hormone refractory, castration resistant, androgen deprivation resistant, androgen ablation resistant, androgen depletion-independent, castration-recurrent, and anti-androgen-recurrent).

BACKGROUND

Androgens mediate their effects through the androgen receptor (AR). Androgens play a role in a wide range of developmental and physiological responses and are involved in male sexual differentiation, maintenance of spermatogenesis, and male gonadotropin regulation. Several lines of evidence show that androgens are associated with the development of prostate carcinogenesis. Firstly, androgens induce prostatic carcinogenesis in rodent models and men receiving androgens in the form of anabolic steroids have a higher incidence of prostate cancer. Second, prostate cancer does not develop if humans or dogs are castrated before puberty. Castration of adult males causes involution of the prostate and apoptosis of prostatic epithelium while eliciting no effect on other male external genitalia. This dependency on androgens provides the underlying rationale for treating prostate cancer with chemical or surgical castration (androgen ablation).

Androgens also play a role in female cancers. One example is ovarian cancer where elevated levels of androgens are associated with an increased risk of developing ovarian cancer. The AR has been detected in a large majority of ovarian cancers whereas Estrogen receptor-alpha (ERa) and the progesterone receptor are detected in less than 50% of ovarian tumors.

The only effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of androgens (androgen-independent disease). Androgen-independent disease is biochemically characterized before the onset of symptoms by a rising titre of serum prostate-specific antigen (PSA). Once the disease becomes androgen-independent most patients succumb within two years.

The AR has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the AR results in its activation such that the receptor can effectively bind to its specific DNA consensus site, termed the androgen response element (ARE), on the promoter and enhancer regions of "normally" androgen regulated genes (such as PSA) to initiate transcription. The AR can be activated in the absence of androgen by stimulation of the cAMP-dependent protein kinase (PKA) pathway, with interleukin-6 (IL-6) and by various growth factors. The mechanism of ligand-independent transformation of the AR has been shown to involve: 1) increased nuclear AR protein suggesting nuclear translocation; 2) increased AR/ARE complex formation; and 3) the NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR may be activated in the absence of testicular androgens by alternative signal transduction pathways in androgen-independent disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the AR include nonsteroidal antiandrogens such as bicalutamide (Casodex™), nilutamide, and flutamide and the steroidal antiandrogen, cyproterone acetate. These antiandrogens target the LBD of the AR and predominantly fail presumably due to poor affinity and mutations that lead to activation of the AR by these same antiandrogens (Taplin, M. E., et al. *Cancer Res.,* 59, 2511-2515 (1999)).

Conventional therapy has concentrated on androgen-dependent activation of the AR through its C-terminal domain. Recent studies developing antagonists to the AR have concentrated on the C-terminus and specifically: 1) the allosteric pocket and AF-2 activity (Estébanez-Perpiñá et al 2007, *PNAS* 104, 16074-16079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñá et al 2005, *JBC* 280, 8060-8068; He et al 2004, *Mol Cell* 16, 425-438).

The AR-NTD is also a target for drug development (e.g. WO 2000/001813), since the NTD plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR carboxy-terminus domain, this has not been the case for the NTD due to its high flexibility and intrinsic disorder in solution (Reid et al 2002 *J. Biol. Chem.* 277, 20079-20086) thereby hampering virtual docking drug discovery approaches.

SUMMARY

This invention is based in part on the fortuitous discovery that compounds described herein modulate androgen receptor (AR) activity. Specifically, compounds identified herein, show inhibition of AR N-Terminal Domain (NTD) transactivation, which may be useful for blocking in vivo tumor growth in the presence and absence of androgens.

The compounds described herein may be used for in vivo or in vitro research uses (i.e. non-clinical) to investigate the mechanisms of orphan and nuclear receptors (including steroid receptors such as the androgen receptor). Furthermore, these compounds may be used individually or as part of a kit for in vivo or in vitro research to investigate signal transduction pathways and/or the activation of orphan and nuclear receptors using recombinant proteins, cells maintained in culture, and/or animal models. Alternatively, the compounds described herein may be combined with commercial packaging and/or instructions for use.

This invention is also based in part on the surprising discovery that the compounds described herein, may also be used to modulate the androgen receptor activity either in vivo or in vitro for both research and therapeutic uses. The compounds may be used in an effective amount so that androgen receptor activity may be modulated. The androgen receptor may be mammalian. The androgen receptor may be human. In particular, the compounds may be used to inhibit transactivation of the AR N-terminal domain (NTD). The compounds modulatory activity may be used in either an in vivo or an in vitro model for the study of at least one of the following indications: prostate cancer, breast cancer, ovarian cancer, endometrial cancer, hair loss, acne, hirsutism, ovarian cysts, polycystic ovary disease, precocious puberty, and age-related macular degeneration. Furthermore, the compounds modulatory activity may be used for the treatment of at least one of the following indications: prostate cancer, breast cancer, ovarian cancer, endometrial cancer, hair loss, acne, hirsutism, ovarian cysts, polycystic ovary disease, precocious puberty (testoxicosis) and age-related macular degeneration. The indication for treatment may be prostate cancer. The prostate cancer may be androgen-independent prostate cancer. The prostate cancer may be androgen-dependent prostate cancer.

In accordance with one embodiment, there is provided a compound having a structure of Formula A:

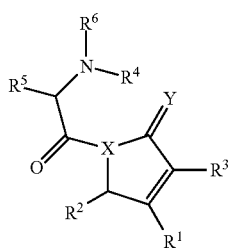

(A)

or a salt thereof, wherein: X may be C or N; Y may be O or S;

$R^1$ may be H, OH, J, OJ, SJ, or NJJ', wherein J or J' may be a one to ten carbon linear, branched, non-aromatic cyclic, or aromatic or partially aromatic cyclic, saturated or unsaturated, optionally substituted alkyl group, wherein the optional substituent may be selected from one or more of: oxo, COOH, COOR, CONH$_2$, CONHR, CONR$_2$, R, OH, OR, F, Cl, Br, I, NH$_2$, NHR, NR$_2$, CN, SH, SR, SO$_3$H, SO$_3$R, SO$_2$R, OSO$_3$R, and NO$_2$, and wherein R may be an linear, or branched saturated and unsubstituted $C_1$-$C_{10}$ alkyl;

$R^2$ may be H or an amino acid side chain, except proline and phenylalanine or a one to ten carbon linear, branched, or non-aromatic cyclic, saturated or unsaturated, optionally substituted alkyl group, wherein the optional substituent may be selected from one or more of: oxo, COOH, COOR, CONH$_2$, CONHR, CONR$_2$, R, OH, OR, F, Cl, Br, I, NH$_2$, NHR, NR$_2$, CN, SH, SR, SO$_3$H, SO$_3$R, SO$_2$R, OSO$_3$R, and NO$_2$, and wherein R may be an linear, or branched saturated and unsubstituted $C_1$-$C_{10}$ alkyl;

$R^3$ may be H, OH, OG, SG, NGG' or a one to ten carbon linear, branched, or non-aromatic cyclic, or aromatic or partially aromatic cyclic, saturated or unsaturated, optionally substituted alkyl group, wherein G and G' may be a one to ten carbon linear, branched, non-aromatic cyclic, or aromatic or partially aromatic cyclic, saturated or unsaturated, optionally substituted alkyl group and wherein the optional substituent may be selected from one or more of: oxo, COOH, OH, COOR, CONH$_2$, CONHR, CONR$_2$, R, F, Cl, Br, I, NH$_2$, CN, SH, SO$_3$H, and NO$_2$, wherein R may be an unsubstituted $C_1$-$C_{10}$ alkyl; and $R^4$ and $R^6$ may be independently selected from the group consisting of: H or an amino acid side chain, except proline and phenylalanine, or a one to ten carbon linear, branched, aromatic or partially aromatic cyclic, or non-aromatic cyclic, saturated or unsaturated, optionally substituted alkyl group, wherein the optional substituent may be selected from one or more of: oxo, COOH, OH, OR, R, F, Cl, Br, I, NH$_2$, NHR, NR$_2$, CN, SH, SR, SO$_3$H, SO$_3$R, SO$_2$R, OSO$_3$R, and NO$_2$, and wherein R may be an unsubstituted $C_1$-$C_{10}$ alkyl, provided that both $R^4$ and $R^6$ are not H and provided that neither $R^4$ and $R^6$ are:

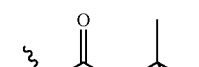

t-Boc

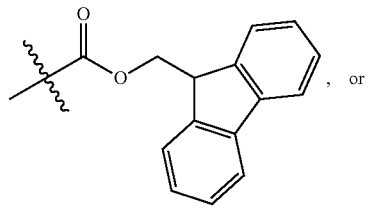

, or

Fmoc

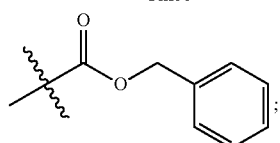

;

Cbz and $R^5$ may be H or an amino acid side chain, except proline and phenylalanine or a one to ten carbon linear, branched, or non-aromatic cyclic, saturated or unsaturated, optionally substituted alkyl group, wherein the optional substituent may be selected from one or more of: oxo, COOH, $CONH_2$, OH, F, Cl, Br, I, $NH_2$, $SO_3H$, and $NO_2$;

-------- may be a single bond or a double bond;

and provided that the compound is not:

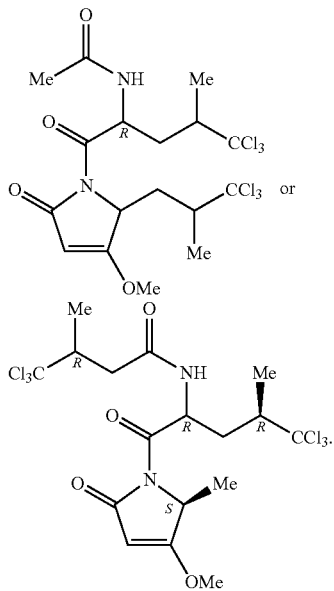

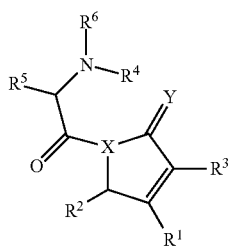

In accordance with a further embodiment, there is provided a compound having a structure of Formula A:

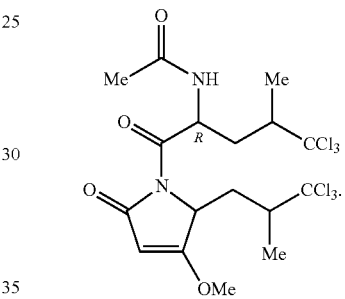

or a salt thereof, wherein: X may be C or N; Y may be O or S;

$R^1$ may be H, OH, J or OJ, wherein J may be a one to ten carbon linear, branched, non-aromatic cyclic, or aromatic cyclic, saturated or unsaturated, optionally substituted alkyl group, wherein the optional substituent may be selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted C1-C10 alkyl;

$R^2$ may be H or a one to ten carbon linear, branched, or non-aromatic cyclic, saturated or unsaturated, optionally substituted alkyl group, wherein the optional substituent may be selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted C1-C10 alkyl;

$R^3$ may be H, OH or a one to ten carbon linear, branched, or non-aromatic cyclic, saturated or unsaturated, optionally substituted alkyl group, wherein the optional substituent may be selected from one or more of: oxo, COOH, OH, F, Cl, Br, I, $NH_2$, CN, SH, $SO_3H$, and $NO_2$; and $R^4$ and $R^6$ are independently selected from the group consisting of: H or a one to ten carbon linear, branched, or non-aromatic cyclic, saturated or unsaturated, optionally substituted alkyl group, wherein the optional substituent may be selected from one or more of: oxo, COOH, OH, F, Br, I, $NH_2$, CN, SH, $SO_3H$, and $NO_2$, and wherein an alkyl carbon may be optionally substituted with a O, provided that both $R^4$ and $R^6$ are not H and provided that neither $R^4$ and $R^6$ are: t-Boc; Fmoc; and Cbz (as described herein); and $R^5$ may be H or a one to ten carbon linear, branched, or non-aromatic cyclic, saturated or unsaturated, optionally substituted alkyl group, wherein the optional substituent may be selected from one or more of: oxo, COOH, OH, F, Cl, Br, I, $NH_2$, $SO_3H$, and $NO_2$;

-------- may be a single bond or a double bond;

and provided that the compound is not:

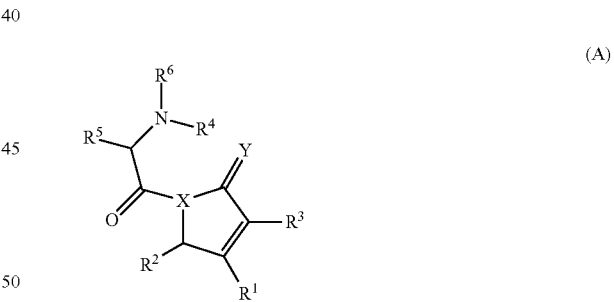

In accordance with a further embodiment, there is provided a compound having a structure of Formula A:

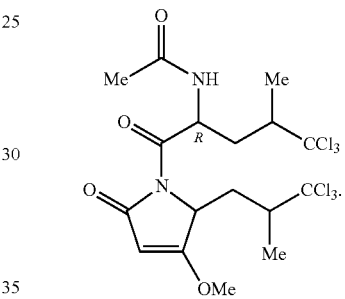

or a salt thereof, wherein: X may be C or N; Y may be O or S;

$R^1$ may be H, OH, J, or OJ, wherein J may be a one to ten carbon linear, branched, non-aromatic cyclic, or aromatic cyclic, saturated or unsaturated, optionally substituted alkyl group, wherein the optional substituent may be selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted C1-C10 alkyl;

$R^2$ may be H or a one to ten carbon linear, branched, or non-aromatic cyclic, saturated or unsaturated, optionally substituted alkyl group, wherein the optional substituent may be selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted $C1$-$C10$ alkyl;

$R^3$ may be H, OH or a one to ten carbon linear, branched, or non-aromatic cyclic, saturated or unsaturated, optionally substituted alkyl group, wherein the optional substituent may be selected from one or more of: oxo, COOH, OH, F, Cl, Br, I, $NH_2$, CN, SH, $SO_3H$, and $NO_2$; and $R^4$ and $R^6$ are independently selected from the group consisting of: H or $COOCH_2CH_3$, provided that both $R^4$ and $R^6$ are not H;

$R^5$ may be H or a one to ten carbon linear, branched, or non-aromatic cyclic, saturated or unsaturated, optionally substituted alkyl group, wherein the optional substituent may be selected from one or more of: oxo, COOH, OH, F, Cl, Br, I, $NH_2$, $SO_3H$, and $NO_2$; and -------- may be a single bond or a double bond.

In accordance with a further embodiment, there is provided a compound having a structure of Formula B:

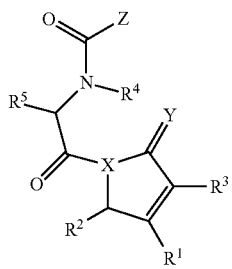

(B)

or a salt thereof, wherein: X may be C or N; Y may be O or S;

$R^1$ may be H, OH, J, OJ, SJ, or NJJ', wherein J or J' may be a one to ten carbon linear, branched, non-aromatic cyclic, or aromatic cyclic, saturated or unsaturated, optionally substituted alkyl group, wherein the optional substituent may be selected from one or more of: oxo, COOH, OH, OR, F, Cl, Br, I, $NH_2$, CN, SH, $SO_3H$, and $NO_2$;

$R^2$ may be H or a one to ten carbon linear, branched, or non-aromatic cyclic, saturated or unsaturated, optionally substituted alkyl group, wherein the optional substituent may be selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted $C1$-$C10$ alkyl;

$R^3$ may be H, OH, OG, SG, NGG' or a one to ten carbon linear, branched, or non-aromatic cyclic, saturated or unsaturated, optionally substituted alkyl group, wherein G and G' are a one to ten carbon linear, branched, or non-aromatic cyclic, saturated or unsaturated alkyl group and wherein the optional substituent may be selected from one or more of: oxo, COOH, OH, F, Cl, Br, I, $NH_2$, CN, SH, $SO_3H$, and $NO_2$; and $R^4$ may be H or a one to ten carbon linear, branched, aromatic cyclic, or non-aromatic cyclic, saturated or unsaturated, optionally substituted alkyl group, wherein the optional substituent may be selected from one or more of: oxo, COOH, OH, OR, R, F, Cl, Br, I, $NH_2$, NHR, $NR_2$, CN, SH, SR, $SO_3H$, $SO_3R$, $SO_2R$, $OSO_3R$, and $NO_2$, and wherein R may be an unsubstituted $C_1$-$C_{10}$ alkyl, provided that $R^4$ is not: t-Boc; Fmoc; and Cbz (as described herein); and $R^5$ may be H or a one to ten carbon linear, branched, or non-aromatic cyclic, saturated or unsaturated, optionally substituted alkyl group, wherein the optional substituent may be selected from one or more of: oxo, COOH, OH, F, Cl, Br, I, $NH_2$, $SO_3H$, and $NO_2$;

Z may be an optionally substituted Bu, Pr, Et, or Me, wherein the optional substituent may be selected from one or more of: oxo, COOH, OH, F, Cl, Br, I, $NH_2$, $SO_3H$, and $NO_2$;

-------- may be a single bond or a double bond;

and provided that the compound is not:

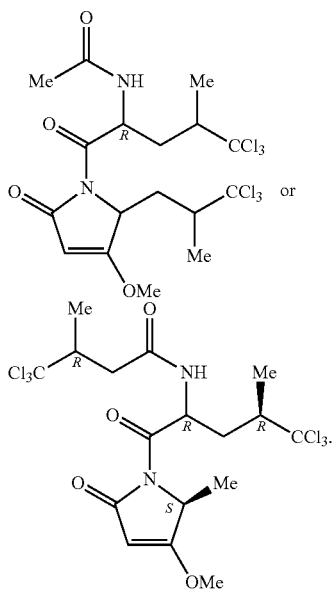

$R^3$ may be H, OH, OG, or a one to ten carbon linear, or branched, saturated or unsaturated, optionally substituted alkyl group, wherein G may be a one to ten carbon linear, or branched, saturated or unsaturated alkyl group and wherein the optional substituent may be selected from one or more of: oxo, COOH, OH, F, Cl, Br, I, $NH_2$, CN, SH, $SO_3H$, and $NO_2$. Alternatively, $R^3$ may be H, OH, OBu, OPr, OEt, or OMe. Alternatively, $R^3$ may be H.

$R^1$ may be H, OH, J, or OJ, wherein J may be a one to ten carbon linear, branched, non-aromatic cyclic, or aromatic cyclic, saturated or unsaturated, optionally substituted alkyl group, wherein the optional substituent may be selected from one or more of: oxo, COOH, OH, F, Cl, Br, I, $NH_2$, and $NO_2$. Alternatively, $R^1$ may be H, OH, J, or OJ, wherein J may be a one to four carbon linear, or branched, saturated or unsaturated, optionally substituted alkyl group, wherein the optional substituent may be selected from one or more of: oxo, COOH, OH, F, Cl, Br, I, and $NH_2$. $R^1$ may also be H, OH, OBu, OPr, OEt, OMe, Bu, Pr, Et, or Me. Alternatively, $R^1$ may be H, OH, J, or OJ, wherein J may be a one to four carbon linear, or branched, saturated or unsaturated, optionally substituted alkyl group, wherein the optional substituent may be selected from one or more of: oxo, OH, F, Cl, Br, I, and $NH_2$. $R^1$ may also be H, OH, OBu, OPr, OEt, or OMe. $R^1$ may be OME.

-------- may be a double bond.

$R^2$ may be H or a one to ten carbon linear, or branched, saturated or unsaturated, optionally substituted alkyl group, wherein the optional substituent may be selected from one or more of: oxo, COOH, OH, F, Cl, Br, I, $NH_2$, and $NO_2$.

Alternatively, $R^2$ may be H or a one to four carbon linear, or branched, saturated optionally substituted alkyl group, wherein the optional substituent may be selected from one or more of: oxo, OH, F, Cl, Br, I, and $NH_2$. Alternatively, $R^2$ may be H or a one to four carbon linear, or branched, saturated optionally substituted alkyl group, wherein the optional substituent may be one or more halogens. Alternatively, $R^2$ may be H or a one to four carbon linear, or branched, saturated optionally substituted alkyl group, wherein the optional substituent may be one or more Cl moieties.

$R^4$ may be H or a one to ten carbon linear, or branched, saturated or unsaturated, optionally substituted alkyl group, wherein the optional substituent may be selected from one or more of: oxo, COOH, OH, F, Cl, Br, I, $NH_2$, SH, $SO_3H$, and $NO_2$. Alternatively, $R^4$ may be H or a one to four carbon linear, or branched, saturated optionally substituted alkyl group, wherein the optional substituent may be selected from one or more of: oxo, OH, F, Cl, Br, I, and $NH_2$. Alternatively, $R^4$ may be H or a one to four carbon linear, or branched, saturated optionally substituted alkyl group, wherein the optional substituent may be selected from one or more halogens. Alternatively, $R^4$ may be H or a one to four carbon linear, or branched, saturated optionally substituted alkyl group, wherein the optional substituent may be one or more halogens. Alternatively, $R^4$ may be H or a one to four carbon linear, or branched, saturated optionally substituted alkyl group, wherein the optional substituent may be one or more Cl moieties.

$R^5$ may be H or a one to ten carbon linear, or branched, saturated or unsaturated, optionally substituted alkyl group, wherein the optional substituent may be selected from one or more of: oxo, COOH, OH, F, Cl, Br, I, $NH_2$, $SO_3H$, and $NO_2$. Alternatively, $R^5$ may be H or a one to four carbon linear, or branched, saturated optionally substituted alkyl group, wherein the optional substituent may be selected from one or more of: oxo, OH, F, Cl, Br, I, and $NH_2$. Alternatively, $R^5$ may be H or a one to four carbon linear, or branched, saturated optionally substituted alkyl group, wherein the optional substituent may be one or more halogens. Alternatively, $R^5$ may be H or a one to four carbon linear, or branched, saturated optionally substituted alkyl group, wherein the optional substituent may be one or more Cl moieties.

X may be N. Y may be O.

Z may be an optionally substituted Bu, Pr, Et, or Me, wherein the optional substituent may be selected from one or more of: oxo, OH, F, Cl, Br, and I. Alternatively, Z may be an optionally substituted Bu, Pr, Et, or Me, wherein the optional substituent may be selected from one or more of: F, Cl, Br, and I.

In accordance with a further embodiment, there is provided a compound having a structure of Formula C:

(C)

or a salt thereof, wherein; A may be Bu, Pr, Et, or Me; M may be H, OH, OBu, OPr, OEt, OMe, Bu, Pr, Et, or Me; T may be

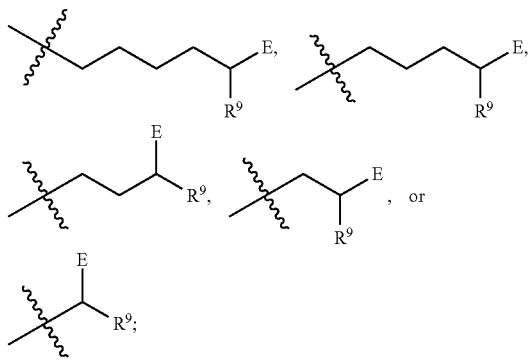

E may be Bu, Pr, Et, or Me;
Q may be

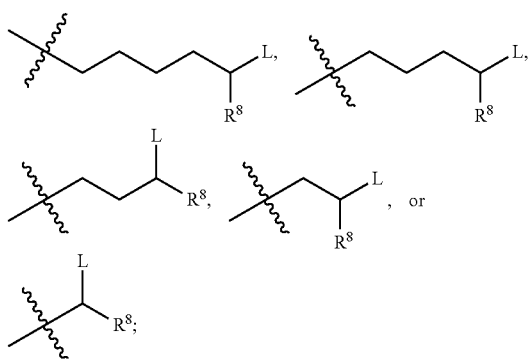

L may be Bu, Pr, Et, or Me; $R^8$ may be $Cl_3C$, $Cl_2HC$, $ClH_2C$, Bu, Pr, Et, or Me; and $R^9$ may be $Cl_3C$, $Cl_2HC$, $ClH_2C$, Bu, Pr, Et, or Me; and wherein; A, T, E, Q, and L are optionally substituted, wherein the optional substituent may be selected from one or more of: oxo, COOH, OH, F, Cl, Br, I, $NH_2$, $SO_3H$, and $NO_2$.

In accordance with a further embodiment, there is provided a compound having a structure of Formula D:

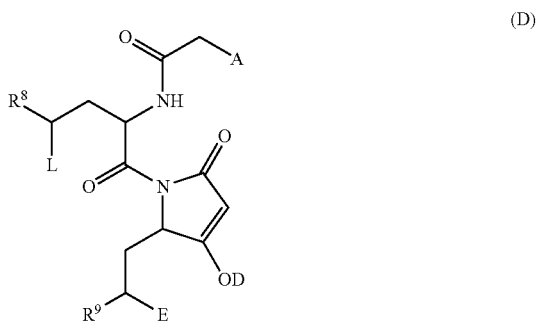

(D)

or a salt thereof, wherein, A may be Bu, Pr, Et, or Me; D may be Bu, Pr, Et, or Me; E may be Bu, Pr, Et, or Me; L may be Bu, Pr, Et, or Me; $R^8$ may be $Cl_3C$, $Cl_2HC$, $ClH_2C$, Bu, Pr, Et, or Me; and $R^9$ may be $Cl_3C$, $Cl_2HC$, $ClH_2C$, Bu, Pr, Et, or Me.

In accordance with a further embodiment, there is provided a compound having a structure of Formula E:

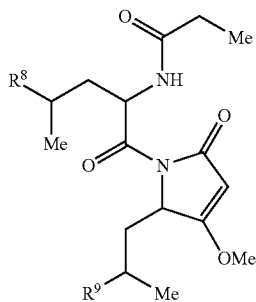
(E)

or a salt thereof, wherein, $R^8$ may be $Cl_3C$, $Cl_2HC$, $ClH_2C$, Et, or Me; and $R^9$ may be $Cl_3C$, $Cl_2HC$, $ClH_2C$, Et, or Me.

In accordance with a further embodiment, there is provided a compound or a salt thereof, selected from one or more of the following:

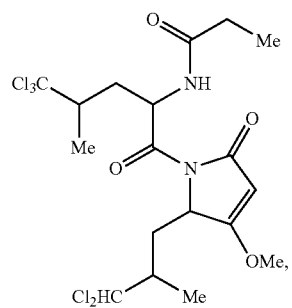

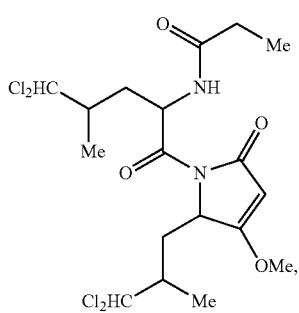

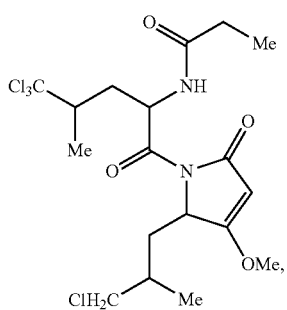

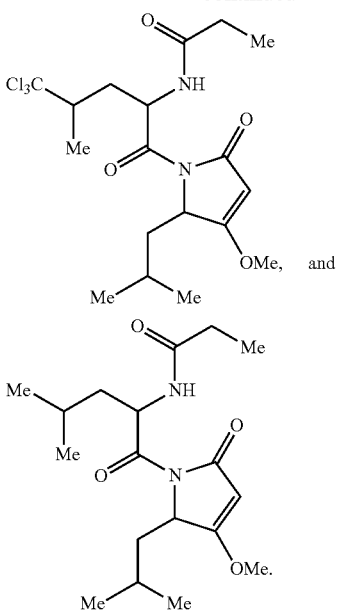

and

In accordance with a further embodiment, there is provided a compound or a salt thereof, selected from one or more of the following:

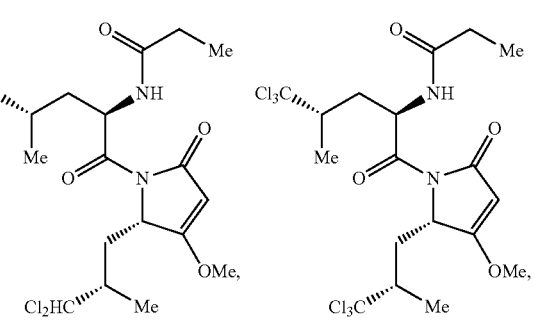

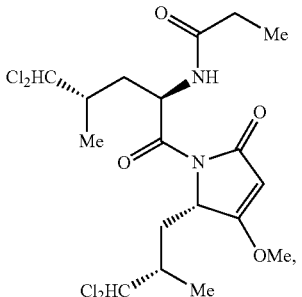

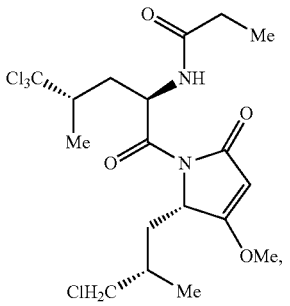

-continued

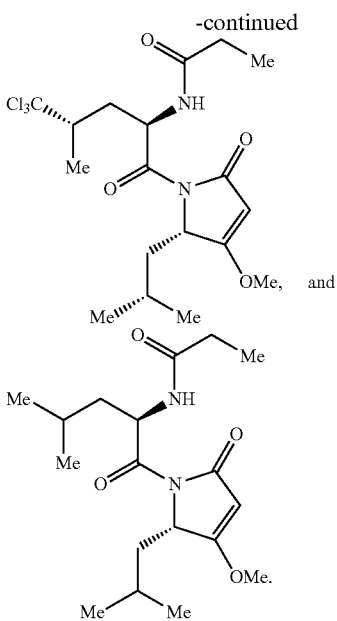

In accordance with a further embodiment, there is provided a method for modulating AR activity, the method including administering to a mammalian cell a compound having a structure of Formula A:

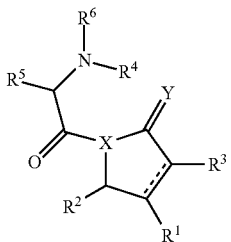

(A)

or a salt thereof, wherein: X may be C or N; Y may be O or S;

$R^1$ may be H, OH, J, OJ, SJ, or NJJ', wherein J or J' may be a one to ten carbon linear, branched, non-aromatic cyclic, or aromatic cyclic, saturated or unsaturated, optionally substituted alkyl group, wherein the optional substituent may be selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted $C_1$-$C_{10}$ alkyl;

$R^2$ may be H or a one to ten carbon linear, branched, or non-aromatic cyclic, saturated or unsaturated, optionally substituted alkyl group, wherein the optional substituent may be selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted $C_1$-$C_{10}$ alkyl;

$R^3$ may be H, OH, OG, SG, NGG' or a one to ten carbon linear, branched, or non-aromatic cyclic, saturated or unsaturated, optionally substituted alkyl group, wherein G and G' are a one to ten carbon linear, branched, or non-aromatic cyclic, saturated or unsaturated, optionally substituted alkyl group and wherein the optional substituent may be selected from one or more of: oxo, COOH, OH, F, Cl, Br, I, $NH_2$, CN, SH, $SO_3H$, and $NO_2$;

$R^4$ and $R^6$ are independently selected from the group consisting of H or a one to ten carbon linear, branched, aromatic cyclic, or non-aromatic cyclic, saturated or unsaturated, optionally substituted alkyl group, wherein the optional substituent may be selected from one or more of: oxo, COOH, OH, OR, R, F, Cl, Br, I, $NH_2$, NHR, $NR_2$, CN, SH, SR, $SO_3H$, $SO_3R$, $SO_2R$, $OSO_3R$, and $NO_2$, and wherein R may be an linear, or branched saturated and unsubstituted $C_1$-$C_{10}$ alkyl;

$R^5$ may be H or a one to ten carbon linear, branched, or non-aromatic cyclic, saturated or unsaturated, optionally substituted alkyl group, wherein the optional substituent may be selected from one or more of: oxo, COOH, OH, F, Cl, Br, I, $NH_2$, $SO_3H$, and $NO_2$; and -------- may be a single bond or a double bond.

Alternatively, the compound for use in the methods/uses described herein may have the structure of any one of Formulas A-E as described herein.

In accordance with a further embodiment, there is provided a use of a compound as set out herein for modulating androgen receptor (AR) activity. Alternatively, the use may be for the preparation of a medicament for modulating androgen receptor (AR). Alternatively, the use may be for the treatment of or for the preparation of a medicament for the treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration. The indication may be prostate cancer. The prostate cancer may be androgen-independent prostate cancer. The prostate cancer may be androgen-dependent prostate cancer.

In accordance with another embodiment, there is provided a pharmaceutical composition comprising a compound having a structure of any one of Formulas A, B, C, D, E as set out above or any of the compounds set out above and a pharmaceutically acceptable excipient.

In accordance with another embodiment, there is provided a pharmaceutical composition comprising a compound according to any one of the above compounds and a pharmaceutically acceptable excipient.

In accordance with a further embodiment, there is provided a method of screening for androgen receptor modulating compounds, wherein the compounds screened are selected from compounds described herein.

In accordance with a further embodiment, there is provided one or more of the compounds described herein for modulating androgen receptor (AR) activity.

The compounds described herein are meant to include all racemic mixtures and all individual enantiomers or combinations thereof, whether or not they are represented herein. An optional substituent may halogen. $R_2$, $R_4$, $R_5$, and $R_6$ may be the side chain of any naturally occurring amino acid or a substituted variant thereof. Alternatively, $R_2$ is not proline or phenylalanine. Alternatively, $R_4$, and $R_6$ are not proline or phenylalanine. Alternatively, $R_5$ is not proline. The amino acid side chain may be selected from the aliphatic side chains valine, leucine, isoleucine or a mono-, di-, or tri-halogenated-methyl version of the side chains of valine, leucine or isoleucine. The amino acid side chain may be selected from the hydrophobic side chains alanine, valine, leucine, isoleucine, tryptophan, methionine, cysteine and glycine. Alternatively, the amino acid side chain may be selected from the hydrophilic side chains asparagine, glutamine, serine, threonine, and tyrosine. Alternatively, the amino acid side chain may be selected from the basic side chains lysine, arginine, and histidine. Alternatively, the amino acid side chain may be selected from the basic side chains aspartate and glutamate. Alternatively, the amino acid side chain may be selected from any of the side chains listed herein or a mono-, di-, or tri-halogenated versions thereof. The halogen may be F, Cl, Br, or I. Alternatively, $R_1$, $R_2$, $R_3$, $R_4$, $R_5$, and $R_6$ may be a one to ten carbon substituted or unsubstituted acyl such as acetyl, propionyl, butanoyl or pentanoyl.

The mammalian cell may be a human cell. The modulating AR activity may be for inhibiting AR N-terminal domain activity. The modulating AR activity may be for inhibiting AR N-terminal domain (NTD) activity. The modulating may be in vivo. The modulating AR activity may be for treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration. The indication may be prostate cancer. The prostate cancer may be androgen-independent prostate cancer. The prostate cancer may be androgen-dependent prostate cancer.

In accordance with a further embodiment, there is provided a method for preparing a compound of the formula (K):

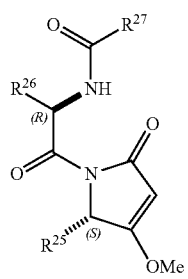

(K)

wherein:
$R^{25}$ may be H or an amino acid side chain, except proline and phenylalanine or a one to ten carbon linear, branched, or non-aromatic cyclic, saturated or unsaturated, optionally substituted alkyl group, wherein the optional substituent may be selected from one or more of: oxo, COOH, COOR', CONH$_2$, CONHR', CONR'$_2$, R', OH, OR', F, Cl, Br, I, NH$_2$, NHR', NR'$_2$, CN, SH, SR', SO$_3$H, SO$_3$R', SO$_2$R', OSO$_3$R', and NO$_2$, and wherein R' may be a linear, or branched saturated and unsubstituted $C_1$-$C_{10}$ alkyl;

$R^{26}$ may be H or an amino acid side chain, except proline and phenylalanine or a one to ten carbon linear, branched, or non-aromatic cyclic, saturated or unsaturated, optionally substituted alkyl group, wherein the optional substituent may be selected from one or more of: oxo, COOH, CONH$_2$, OH, F, Cl, Br, I, NH$_2$, SO$_3$H, and NO$_2$; and $R^{27}$ may be an optionally substituted Bu, Pr, Et, or Me, wherein the optional substituent may be selected from one or more of: oxo, COOH, OH, F, Cl, Br, I, NH$_2$, SO$_3$H, and NO$_2$.

In accordance with another embodiment, there is provided a use of a compound of the Formula (F):

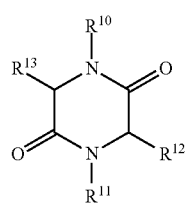

(F)

or a pharmaceutically acceptable salt thereof for the modulation of androgen receptor (AR) activity, wherein:

$R^{10}$ may be H or a one to ten carbon linear, branched, or cyclic, saturated or unsaturated, optionally substituted alkyl group, wherein the optional substituent may be selected from one or more of: oxo, COOH, $R^{14}$, OH, OR$^{14}$, F, Cl, Br, I, NH$_2$, NHR$^{14}$, NR$^{14}$$_2$, CN, SH, SR$^{14}$, SO$_3$H, SO$_3$R$^{14}$, SO$_2$R$^{14}$, OSO$_3$R$^{14}$, and NO$_2$, and wherein R$^{14}$ may be an unsubstituted $C_1$-$C_{10}$ linear, branched, or cyclic, saturated or unsaturated alkyl group;

$R^{11}$ may be H or a one to ten carbon linear, branched, or cyclic, saturated or unsaturated, optionally substituted alkyl group, wherein the optional substituent may be selected from one or more of: oxo, COOH, $R^{15}$, OH, OR$^{15}$, F, Cl, Br, I, NH$_2$, NHR$^{15}$, NR$^{15}$$_2$, CN, SH, SR$^{15}$ SO$_3$H, SO$_3$R$^{15}$, SO$_2$R$^{15}$, OSO$_3$R$^{15}$, and NO$_2$, and wherein R$^{15}$ may be an unsubstituted $C_1$-$C_{10}$ linear, branched, or cyclic, saturated or unsaturated alkyl group;

$R^{12}$ may be H or a one to ten carbon linear, branched, or cyclic, saturated or unsaturated, optionally substituted alkyl group, wherein the optional substituent may be selected from one or more of: oxo, COOH, $R^{16}$, OH, OR$^{16}$, F, Cl, Br, I, NH$_2$, NHR$^{16}$, NR$^{16}$$_2$, CN, SH, SR$^{16}$, SO$_3$H, SO$_3$R$^{16}$, SO$_2$R$^{16}$, OSO$_3$R$^{16}$, and NO$_2$, and wherein R$^{16}$ may be an unsubstituted $C_1$-$C_{10}$ linear, branched, or cyclic, saturated or unsaturated alkyl group; and $R^{13}$ may be H or a one to ten carbon linear, branched, or cyclic, saturated or unsaturated, optionally substituted alkyl group, wherein the optional substituent may be selected from one or more of: oxo, COOH, $R^{17}$, OH, OR$^{17}$, F, Cl, Br, I, NH$_2$, NHR$^{17}$, NR$^{17}$$_2$, CN, SH, SR$^{17}$, SO$_3$H, SO$_3$R$^{17}$, SO$_2$R$^{17}$, OSO$_3$R$^{17}$, and NO$_2$, and wherein R$^{17}$ may be an unsubstituted $C_1$-$C_{10}$ linear, branched, or cyclic, saturated or unsaturated alkyl group.

In an embodiment, $R^{10}$ may be, for example, and without limitation, H, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy, wherein each of $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy is unsubstituted or substituted with one or more substituents each of which may be independently oxo, COOH, R$^{14}$, OH, OR$^{14}$, F, Cl, Br, I, NH$_2$, NHR$^{14}$, NR$^{14}$$_2$, CN, SH, SR$^{14}$, SO$_3$H, SO$_3$R$^{14}$, SO$_2$R$^{14}$, OSO$_3$R$^{14}$, or NO$_2$, wherein R$^{14}$ may be, for example, and without limitation, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, or a 5- to 10-membered aromatic heterocyclic group containing one or more heteroatoms which are independently N, S or O;

$R^{11}$ may be, for example, and without limitation, H, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy, wherein each of $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy is unsubstituted or substituted with one or more substituents each of which may be independently oxo, COOH, $R^{15}$, OH, OR$^{15}$, F, Cl, Br, I, NH$_2$, NHR$^{15}$, NR$^{15}_2$, CN, SH, SR$^{15}$, SO$_3$H, SO$_3$R$^{15}$, SO$_2$R$^{15}$, OSO$_3$R$^{15}$, or NO$_2$, wherein $R^{15}$ may be, for example, and without limitation, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, or a 5- to 10-membered aromatic heterocyclic group containing one or more heteroatoms which are independently N, S or O;

$R^{12}$ may be, for example, and without limitation, H, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy, wherein each of $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy is unsubstituted or substituted with one or more substituents each of which may be the independently oxo, COOH, $R^{16}$, OH, OR$^{16}$, F, Cl, Br, I, NH$_2$, NHR$^{16}$, NR$^{16}_2$, CN, SH, SR$^{16}$, SO$_3$H, SO$_3$R$^{16}$, SO$_2$R$^{16}$, OSO$_3$R$^{16}$, or NO$_2$, wherein $R^{16}$ may be, for example, and without limitation, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, or a 5- to 10-membered aromatic heterocyclic group containing one or more heteroatoms which are independently N, S or O; and $R^{13}$ may be, for example, and without limitation, H, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy, wherein each of $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{1-10}$ acyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, a 5- to 10-membered aromatic heterocyclic group containing one or more heteroatoms which are independently N, S or O, or $C_{1-10}$ alkoxy is unsubstituted or substituted with one or more substituents each of which may be independently oxo, COOH, $R^{17}$, OH, OR$^{17}$, F, Cl, Br, I, NH$_2$, NHR$^{17}$, NR$^{17}_2$, CN, SH, SR$^{17}$, SO$_3$H, SO$_3$R$^{17}$, SO$_2$R$^{17}$, OSO$_3$R$^{17}$, or NO$_2$, wherein $R^{17}$ may be, for example, and without limitation, $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, or a 5- to 10-membered aromatic heterocyclic group containing one or more heteroatoms which are independently N, S or O.

In an embodiment, $R^{10}$ may be, for example, and without limitation, H or unsubstituted $C_{1-10}$ alkyl. In another embodiment, $R^{10}$ may be, for example, and without limitation, Me.

In an embodiment, $R^{11}$ may be, for example, and without limitation, H or unsubstituted $C_{1-10}$ alkyl. In another embodiment, $R^{11}$ may be, for example, and without limitation, Me.

In another embodiment, $R^{12}$ may be, for example, and without limitation, H, $C_{1-10}$ alkyl or $C_{2-10}$ alkenyl, wherein each of $C_{1-10}$ alkyl or $C_{2-10}$ alkenyl is unsubstituted or substituted with one or more substituents each of which may be the independently oxo, COOH, $R^{16}$, OH, OR$^{16}$, F, Cl, Br, I, NH$_2$, NHR$^{16}$, NR$^{16}_2$, CN, SH, SR$^{16}$, SO$_3$H, SO$_3$R$^{16}$, SO$_2$R$^{16}$, OSO$_3$R$^{16}$, or NO$_2$, wherein $R^{16}$ may be $C_{1-10}$ alkyl, $C_{2-10}$ alkenyl, $C_{2-10}$ alkynyl, $C_{3-10}$ cycloalkyl, $C_{3-10}$ cycloalkenyl, $C_{3-10}$ cycloalkynyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently N, S or O, or a 5- to 10-membered aromatic heterocyclic group containing one or more heteroatoms which are independently N, S or O. In another embodiment, $R^{12}$ may be the side chain of any naturally occurring amino acid or a substituted variant thereof. The amino acid side chain may be selected from the aliphatic side chains valine, leucine, isoleucine or a mono-, di-, or tri-halogenated-methyl version of the side chains of valine, leucine or isoleucine. The amino acid side chain may be selected from the hydrophobic side chains alanine, valine, leucine, isoleucine, tryptophan, methionine, cysteine and glycine. The amino acid side chain may be selected from the hydrophilic side chains asparagine, glutamine, serine, threonine, and tyrosine. Alternatively, the amino acid side chain may be selected from the basic side chains lysine, arginine, and histidine. Alternatively, the amino acid side chain may be selected from the basic side chains aspartate and glutamate. Alternatively, the amino acid side chain may be selected from any of the side chains listed herein or a mono-, di-, or tri-halogenated versions thereof. The halogen may be F, Cl, Br, or I. In a further embodiment, $R^{12}$ may be, for example, and without limitation, a side chain of valine, leucine, isoleucine or a substituted variant thereof. In another embodiment, $R^{12}$ may be, for example, and without limitation, a mono-, di-, or halogenated-methyl variant of the side chain of valine, leucine or isoleucine. In yet another embodiment, $R^{12}$ may be, for example, and without limitation, —CH$_2$—CH(CH$_3$)CH$_3$; —CH$_2$—CH (CR$^{18}$$_3$)CH$_3$; —CH$_2$—CH(CHR$^{18}$$_2$)CH$_3$; —CH$_2$—CH(CH$_2$R$^{18}$)CH$_3$; —CH$_2$—CH(CR$^{18}$$_3$)CH$_2$R$^{18}$; —CH$_2$—CH(CHR$^{18}$$_2$)CH$_2$R$^{18}$; —CH$_2$—CH(CH$_2$R$^{18}$)CH$_2$R$^{18}$; —CH$_2$—CH(CR$^{18}$$_3$)CHR$^{18}$$_2$; —CH$_2$—CH(CHR$^{18}$$_2$)CHR$^{18}$$_2$; —CH$_2$—CH(CH$_2$R$^{18}$)CHR$^{18}$$_2$; —CH$_2$—CH(CR$^{18}$$_3$)CR$^{18}$$_3$; —CH$_2$—CH(CHR$^{18}$$_2$)CR$^{18}$$_3$; —CH$_2$—CH(CH$_2$R$^{18}$)CR$^{18}$$_3$; —CH(CH$_3$)CH$_3$; —CH(CR$^{18}$$_3$)CH$_3$; —CH(CHR$^{18}$$_2$)CH$_3$; —CH(CH$_2$R$^{18}$)CH$_3$; —CH(CR$^{18}$$_3$)CH$_2$R$^{18}$; —CH(CHR$^{18}$$_2$)CH$_2$R$^{18}$; —CH(CH$_2$R$^{18}$)CH$_2$R$^{18}$; —CH(CR$^{18}$$_3$)CHR$^{18}$$_2$; —CH(CHR$^{18}$$_2$)CHR$^{18}$$_2$; —CH(CH$_2$R$^{18}$)CHR$^{18}$$_2$; —CH(CR$^{18}$$_3$)CR$^{18}$$_3$; —CH(CHR$^{18}$$_2$)CR$^{18}$$_3$; —CH(CH$_2$R$^{18}$)CR$^{18}$$_3$; —CH(CH$_3$)—CH(CH$_3$)CH$_3$; —CH(CH$_3$)—CH(CR$^{18}$$_3$)CH$_3$; —CH(CH$_3$)—CH(CHR$^{18}$$_2$)CH$_3$; —CH(CH$_3$)—CH(CH$_2$R$^{18}$)CH$_3$; —CH(CH$_3$)—CH(CR$^{18}$$_3$)CH$_2$R$^{18}$; —CH(CH$_3$)—CH(CHR$^{18}$$_2$)CH$_2$R$^{18}$; —CH(CH$_3$)—CH(CH$_2$R$^{18}$)CH$_2$R$^{18}$; —CH(CH$_3$)—CH(CR$^{18}$$_3$)CHR$^{18}$$_2$; —CH(CH$_3$)—CH(CHR$^{18}$$_2$)CHR$^{18}$$_2$; —CH(CH$_3$)—CH(CH$_2$R$^{18}$)CHR$^{18}$$_2$; —CH(CH$_3$)—CH(CR$^{18}$$_3$)CR$^{18}$$_3$; —CH(CH$_3$)—CH(CHR$^{18}$$_2$)CR$^{18}$$_3$; or —CH(CH$_3$)—CH(CH$_2$R$^{18}$)CR$^{18}$$_3$, wherein R$^{18}$ may be, for example, and without limitation, F, Cl, Br or I. In an embodiment, R$^{18}$ may be, for example, and without limitation, Cl. In yet another embodiment, R$^{12}$ may be, for example, and without limitation, —CH$_2$—CH(CCl$_3$)CH$_3$ or —CH$_2$—CH(CHCl$_2$)CH$_3$. Alternatively, R$^{12}$ may be a one to ten carbon substituted or unsubstituted acyl such as acetyl, propionyl, butanoyl or pentanoyl.

In another embodiment, R$^{13}$ may be, for example, and without limitation, H, C$_{1-10}$ alkyl or C$_{2-10}$ alkenyl, wherein each of C$_{1-10}$ alkyl or C$_{2-10}$ alkenyl is unsubstituted or substituted with one or more substituents each of which may be independently oxo, COOH, R$^{17}$, OH, OR$^{17}$, F, Cl, Br, I, NH$_2$, NHR$^{17}$, NR$^{17}$$_2$, CN, SH, SR$^{17}$, SO$_3$H, SO$_3$R$^{17}$, SO$_2$R$^{17}$, OSO$_3$R$^{17}$, or NO$_2$, wherein R$^{17}$ may be C$_{1-10}$ alkyl, C$_{2-10}$ alkenyl, C$_{2-10}$ alkynyl, C$_{3-10}$ cycloalkyl, C$_{3-10}$ cycloalkenyl, C$_{3-10}$ cycloalkynyl, C$_{6-10}$ aryl, C$_{6-9}$ aryl-C$_{1-4}$ alkyl, C$_{6-8}$ aryl-C$_{2-4}$ alkenyl, C$_{6-8}$ aryl-C$_{2-4}$ alkynyl, a 4- to 10-membered non-aromatic heterocyclic group containing one or more heteroatoms which are independently N, S or O, or a 5- to 10-membered aromatic heterocyclic group containing one or more heteroatoms which are independently N, S or O. In another embodiment, R$^{13}$ may be the side chain of any naturally occurring amino acid or a substituted variant thereof. The amino acid side chain may be selected from the aliphatic side chains valine, leucine, isoleucine or a mono-, di-, or tri-halogenated-methyl version of the side chains of valine, leucine or isoleucine. The amino acid side chain may be selected from the hydrophobic side chains alanine, valine, leucine, isoleucine, tryptophan, methionine, cysteine and glycine. The amino acid side chain may be selected from the hydrophilic side chains asparagine, glutamine, serine, threonine, and tyrosine. Alternatively, the amino acid side chain may be selected from the basic side chains lysine, arginine, and histidine. Alternatively, the amino acid side chain may be selected from the basic side chains aspartate and glutamate. Alternatively, the amino acid side chain may be selected from any of the side chains listed herein or a mono-, di-, or tri-halogenated versions thereof. The halogen may be F, Cl, Br, or I. In yet another embodiment, R$^{13}$ may be, for example, and without limitation, a mono-, di-, or halogenated-methyl variant of the side chain of valine, leucine or isoleucine. In an embodiment, R$^{13}$ may be, for example, and without limitation, —CH$_2$—CH(CH$_3$)CH$_3$; —CH$_2$—CH(CR$^{19}$$_3$)CH$_3$; —CH$_2$—CH(CHR$^{19}$$_2$)CH$_3$; —CH$_2$—CH(CH$_2$R$^{19}$)CH$_3$; —CH$_2$—CH(CR$^{19}$$_3$)CH$_2$R$^{19}$; —CH$_2$—CH(CHR$^{19}$$_2$)CH$_2$R$^{19}$; —CH$_2$—CH(CH$_2$R$^{19}$)CH$_2$R$^{19}$; —CH$_2$—CH(CR$^{19}$$_3$)CHR$^{19}$$_2$; —CH$_2$—CH(CHR$^{19}$$_2$)CHR$^{19}$$_2$; —CH$_2$—CH(CH$_2$R$^{19}$)CHR$^{19}$$_2$; —CH$_2$—CH(CR$^{19}$$_3$)CR$^{19}$$_3$; —CH$_2$—CH(CHR$^{19}$$_2$)CR$^{19}$$_3$; —CH$_2$—CH(CH$_2$R$^{19}$)CR$^{19}$$_3$; —CH(CH$_3$)CH$_3$; —CH(CR$^{19}$$_3$)CH$_3$; —CH(CHR$^{19}$$_2$)CH$_3$; —CH(CH$_2$R$^{19}$)CH$_3$; —CH(CR$^{19}$$_3$)CH$_2$R$^{19}$; —CH(CHR$^{19}$$_2$)CH$_2$R$^{19}$; —CH(CH$_2$R$^{19}$)CH$_2$R$^{19}$; —CH(CR$^{19}$$_3$)CHR$^{19}$$_2$; —CH(CHR$^{19}$$_2$)CHR$^{19}$$_2$; —CH(CH$_2$R$^{19}$)CHR$^{19}$$_2$; —CH(CR$^{19}$$_3$)CR$^{19}$$_3$; —CH(CHR$^{19}$$_2$)CR$^{19}$$_3$; —CH(CH$_2$R$^{19}$)CR$^{19}$$_3$; —CH(CH$_3$)—CH(CH$_3$)CH$_3$; —CH(CH$_3$)—CH(CR$^{19}$$_3$)CH$_3$; —CH(CH$_3$)—CH(CHR$^{19}$$_2$)CH$_3$; —CH(CH$_3$)—CH(CH$_2$R$^{19}$)CH$_3$; —CH(CH$_3$)—CH(CR$^{19}$$_3$)CH$_2$R$^{19}$; —CH(CH$_3$)—CH(CHR$^{19}$$_2$)CH$_2$R$^{19}$; —CH(CH$_3$)—CH(CH$_2$R$^{19}$)CH$_2$R$^{19}$; —CH(CH$_3$)—CH(CR$^{19}$$_3$)CHR$^{19}$$_2$; —CH(CH$_3$)—CH(CHR$^{19}$$_2$)CHR$^{19}$$_2$; —CH(CH$_3$)—CH(CH$_2$R$^{19}$)CHR$^{19}$$_2$; —CH(CH$_3$)—CH(CR$^{19}$$_3$)CR$^{19}$$_3$; —CH(CH$_3$)—CH(CHR$^{19}$$_2$)CR$^{19}$$_3$; or —CH(CH$_3$)—CH(CH$_2$R$^{19}$)CR$^{19}$$_3$, wherein R$^{19}$ may be, for example, and without limitation, F, Cl, Br or I. In an embodiment, R$^{19}$ may be, for example, and without limitation, Cl. In another embodiment, R$^{13}$ may be, for example, and without limitation, —CH$_2$—CH(CCl$_3$)CH$_3$ or —CH$_2$—CH(CHCl$_2$)CH$_3$. Alternatively, R$^{13}$ may be a one to ten carbon substituted or unsubstituted acyl such as acetyl, propionyl, butanoyl or pentanoyl.

In accordance with another embodiment, there is provided a use of the compound of the formula:

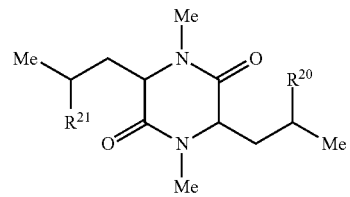

or a pharmaceutically acceptable salt thereof for the modulation of androgen receptor (AR) activity, wherein each of R$^{20}$ and R$^{21}$ may be independently, for example, and without limitation, CCl$_3$ or CHCl$_2$.

According to another embodiment, there is provided a use of the compound of the formula:

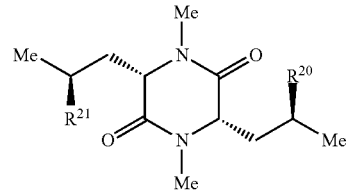

or a pharmaceutically acceptable salt thereof for the modulation of androgen receptor (AR) activity, wherein each of R$^{20}$ and R$^{21}$ may be independently, for example, and without limitation, CCl$_3$ or CHCl$_2$.

In a further embodiment, there is provided a use of the compound of the formula:

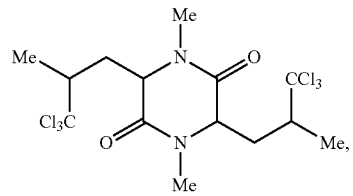

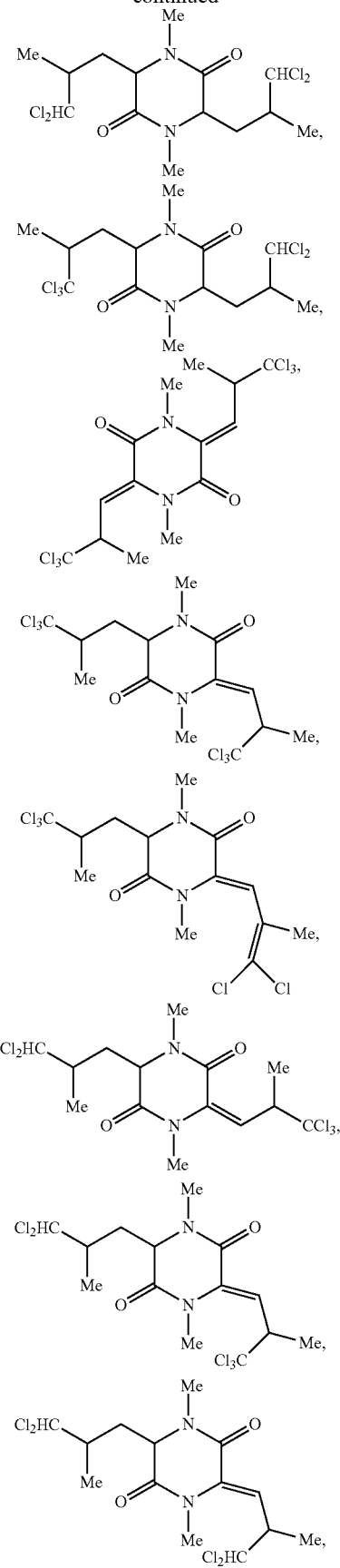
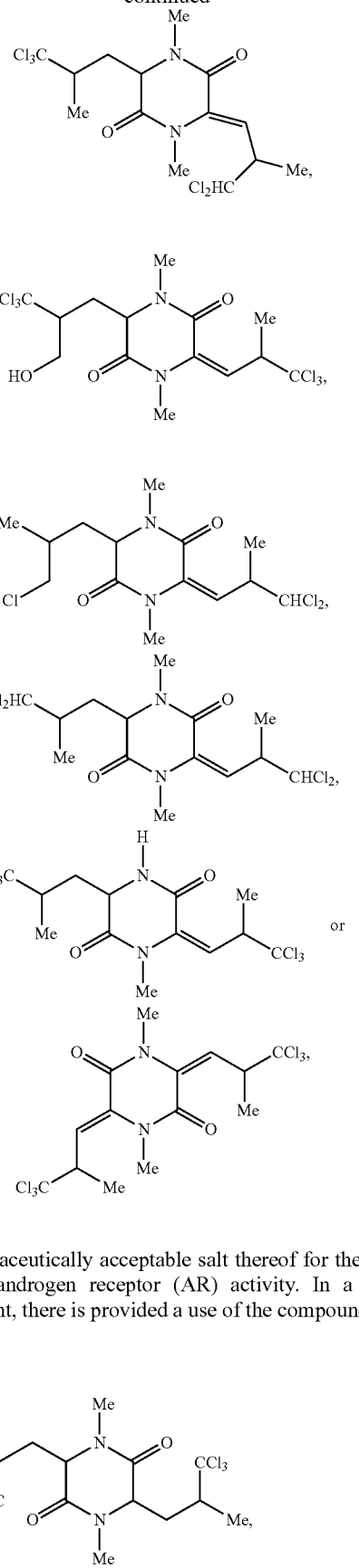
or a pharmaceutically acceptable salt thereof for the modulation of androgen receptor (AR) activity. In a further embodiment, there is provided a use of the compound of the formula:
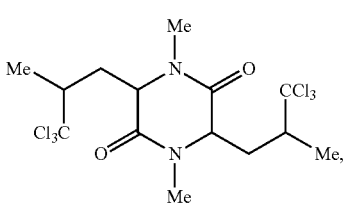

-continued
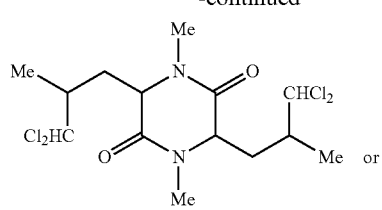
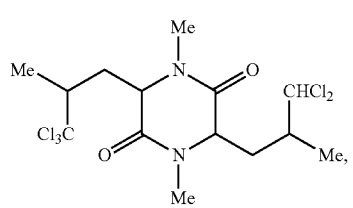
or a pharmaceutically acceptable salt thereof for the modulation of androgen receptor (AR) activity.
In a further embodiment, there is provided a use of the compound of the formula:
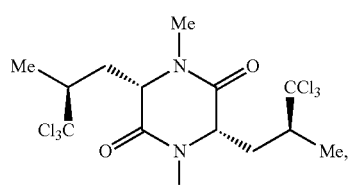
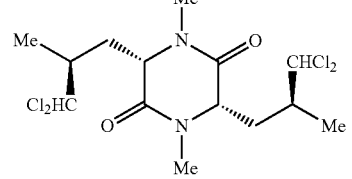
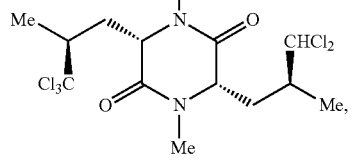
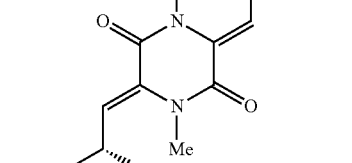
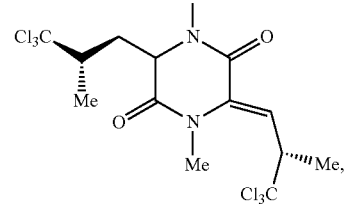
-continued
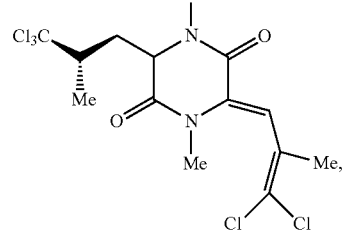
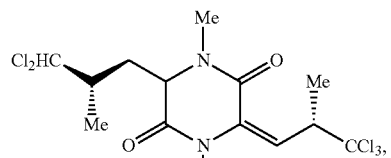
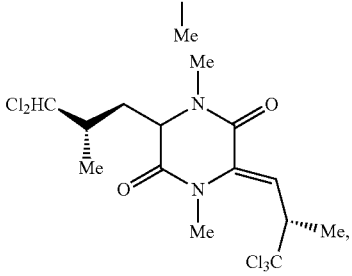
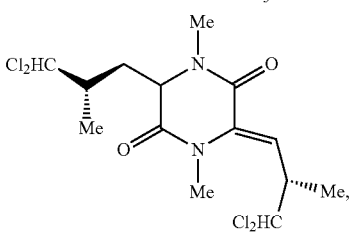
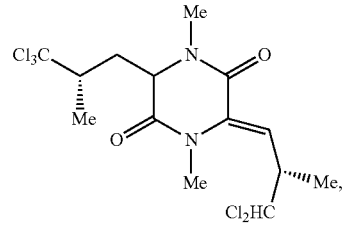
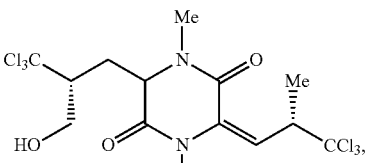
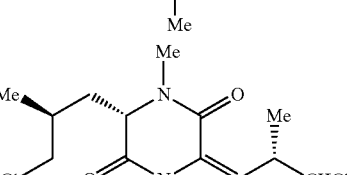
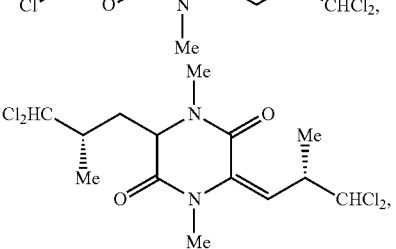

-continued

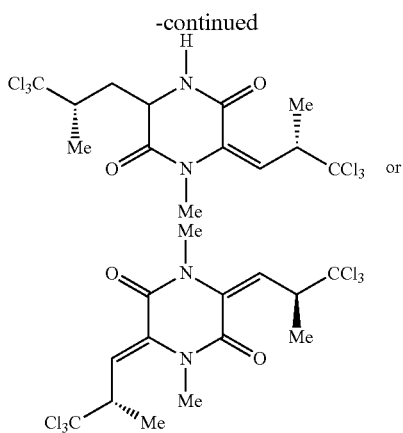

or a pharmaceutically acceptable salt thereof for the modulation of androgen receptor (AR) activity. In a further embodiment, there is provided a use of the compound of the formula:

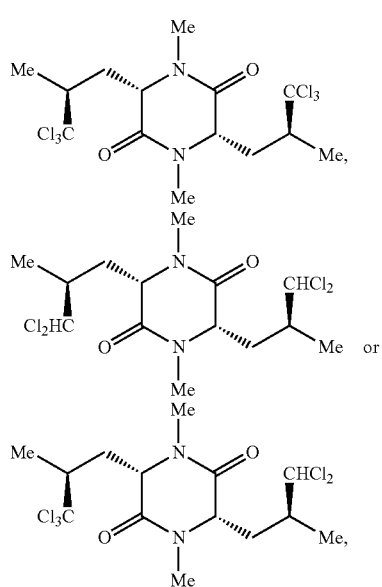

or a pharmaceutically acceptable salt thereof for the modulation of androgen receptor (AR) activity.

In accordance with a further embodiment, there is provided a use of a compound as set out above for modulating androgen receptor (AR) activity. Alternatively, the use may be for the preparation of a medicament for modulating androgen receptor (AR). Alternatively, the use may be for the treatment of or for the preparation of a medicament for the treatment of at least one indication selected from the group consisting of prostate cancer, breast cancer, ovarian cancer, endometrial cancer, hair loss, acne, hirsutism, ovarian cysts, polycystic ovary disease, precocious puberty, and age-related macular degeneration. The indication may be prostate cancer. The prostate cancer may be androgen-independent prostate cancer. The prostate cancer may be androgen-dependent prostate cancer. In accordance with another embodiment, there is provided a method for modulating AR activity, the method including administering to a mammalian cell a compound as set out above or a salt thereof.

In accordance with another embodiment, there is provided a pharmaceutical composition comprising a compound as set out above or any of the compounds set out herein and a pharmaceutically acceptable excipient.

In accordance with a further embodiment, there is provided a method of screening for androgen receptor modulating compounds, wherein the compounds screened are selected from compounds described herein.

In accordance with a further embodiment, there is provided one or more of the compounds described herein for modulating androgen receptor (AR) activity.

The compounds described herein are meant to include all racemic mixtures and all individual enantiomers or combinations thereof, whether or not they are represented herein.

The amino acid side chain may be selected from one or more of the following or one or more of the following groupings of side chains:

Amino acid side chains (excluding Proline)

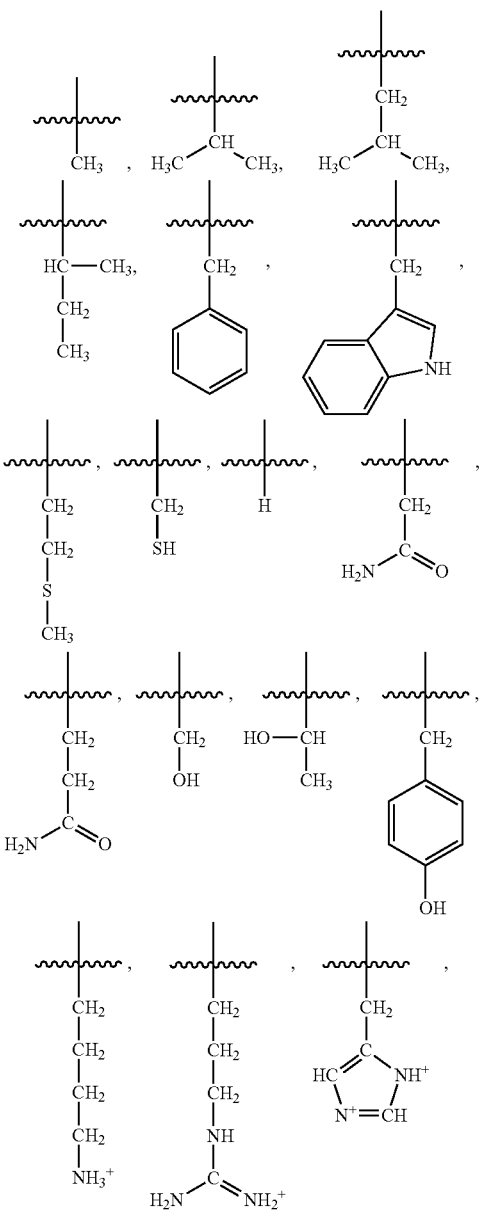

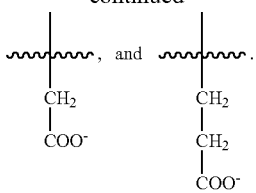, and
Hydrophobic (nonpolar) amino acid side chains excluding Proline
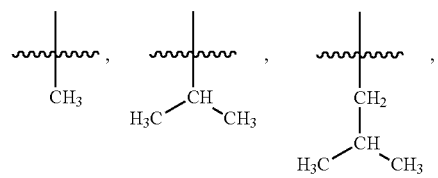
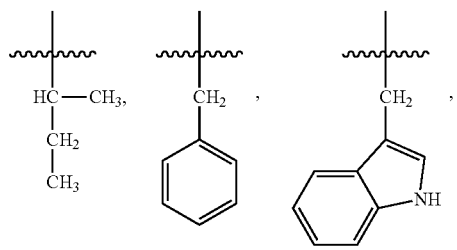
Hydrophilic (polar) amino acid side chains
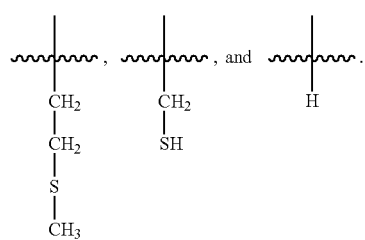
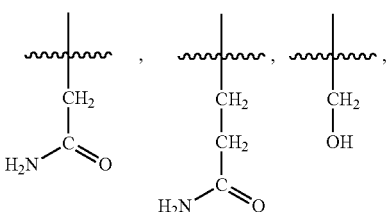
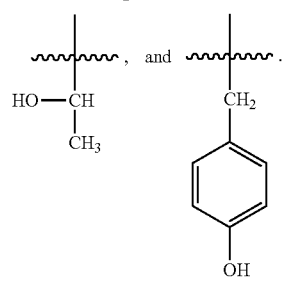
Basic amino acid side chains
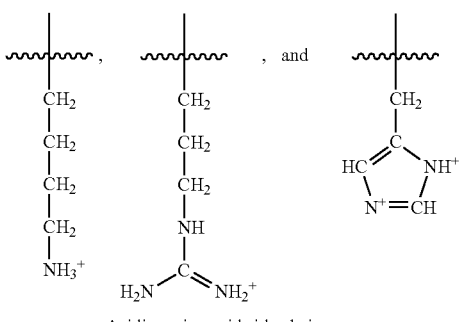
Acidic amino acid side chains
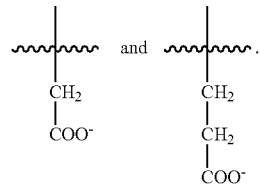
Aliphatic amino acid side chains
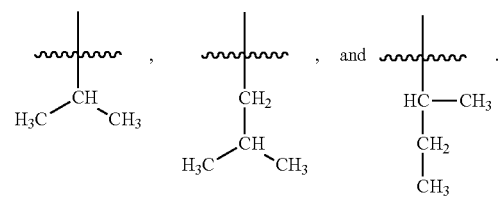
Aromatic amino acid side chains
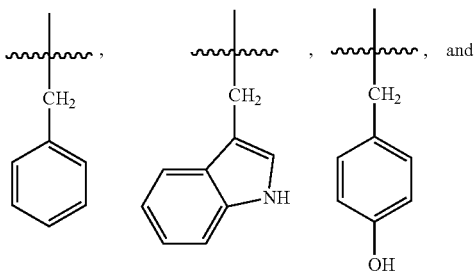
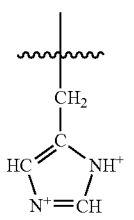
Charged amino acid side chains
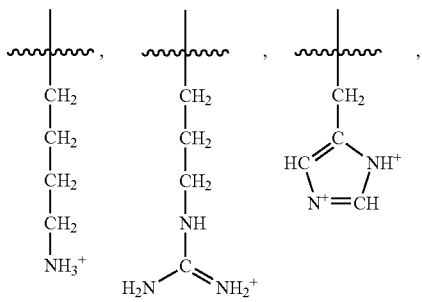

-continued

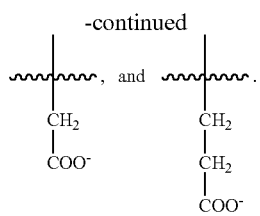

BRIEF DESCRIPTION OF THE DRAWINGS

FIG. 2A-C shows that CB3.1 (5 µg/ml) inhibited ARE-luciferase activity but did NOT inhibit GRE-luciferase activity or PRE-luciferase activity in LNCaP cells that were transfected with expression vectors for GR and PR and their relevance reporter gene constructs (PSA-luc, GRE-luc or PRE-luc) and exposed to their respective steroid (10 nM, black bars) for 24 h. White bars represent no steroid (ethanol control). Wherein glucocorticoid receptor (GR) and progesterone receptor (PR).

FIG. 6 shows a time course showing LNCaP xenograft volume in response to Sintokamide A (CB3.1). CB3.1 reduced the size of the tumors while DMSO-treated tumors continued to grow. Animals were castrated 7 days before 1$^{st}$ injection and tumor volume was set to 100%. Injections were made every 3 days at a dose of 30 mg/kg body weight every 3 days. B. Photograph is of a representative harvested LNCaP xenograft treated with CB3.1. The black bar represents 10 mm.

DETAILED DESCRIPTION

Figure 1A:
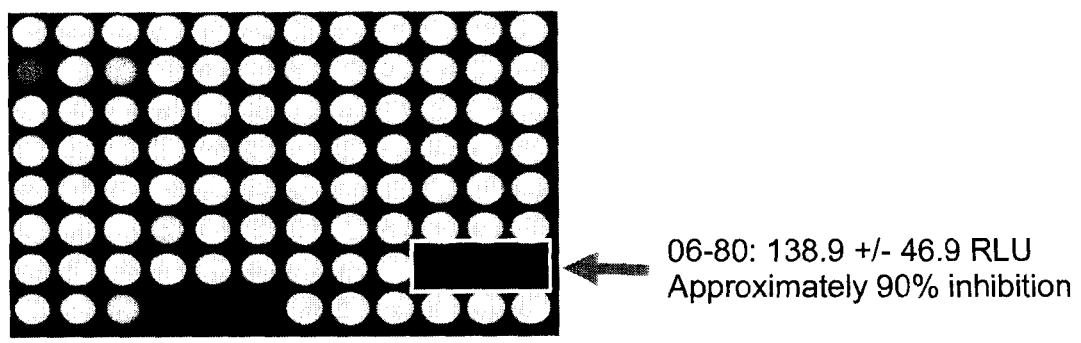
FIG. 1A shows a CLIPR image of luciferase activity in lystates of LNCaP cells stably transfected with ARR3-luc and treated with R1881 and marine extracts (10 ug/ml) for 48 hr. All wells were treated with R1881 (1 nM) and extracts added in triplicate across the rows (4 extracts per row). The boxed wells represent 06-80 (in triplicate) on this plate and show greater than 90% inhibition.

Novel compounds described herein include Sintokamides A (1) to E (5) which all appear to be related to a small family of chlorinated peptides that have been isolated from marine sponges [a] Kazlauskas, R. Murphy, P. T.; Wells, R. J.; Schoenholzer, P. *Tetrahedron Lett.* 1978, 4951-, b) Kazlauskas, R. Murphy, P. T.; Wells, R. J. *Tetrahedron Lett.* 1978, 4949-, c) Hofheinz, W.; Oberhansli, W. E. Helv. Chim. Acta 1977, 60, 660-, d) Erickson, K.; Wells, R. *Aust. J. Chem.* 1982, 35, 31-38, e) Unson, M. D.; Rose, C. B.; Faulkner, D. J.; Brinen, L. S.; Steiner, J. R.; Clardy, J. *J. Org. Chem.* 1993, 58, 6336-6343], nudibranchs [Fahey, S. J.; Garson, M. J. *J. Chem. Ecol.* 2002, 28, 1773-1785], and cyanobacteria [Orjala, J.; Gerwick, W. H. *J. Nat. Prod.* 1996, 59, 427-430]. Furthermore, synthesis and modifications are described in, for example, Willard et al, *J. Org. Chem.*, 1984, 49, 3489-3493 and Brantley et al, *Organic Letters,* 1999, vol 1, No. 13, 2165-2167.

As used herein, the phrase "C$_{x-y}$ alkyl" or "C$_x$-C$_y$ alkyl" is used as it is normally understood to a person of skill in the art and often refers to a chemical entity that has a carbon skeleton or main carbon chain comprising a number from x to y (with all individual integers within the range included, including integers x and y) of carbon atoms. For example a "C$_{1-10}$ alkyl" is a chemical entity that has 1, 2, 3, 4, 5, 6, 7, 8, 9 or 10 carbon atom(s) in its carbon skeleton or main chain.

As used herein, the term "cyclic C$_{x-y}$ alkyl" or "cyclic C$_x$-C$_y$ alkyl" is used as it is normally understood to a person of skill in the art and often refers to a compound or a chemical entity in which at least a portion of the carbon skeleton or main chain of the chemical entity is bonded in such a way so as to form a 'loop', circle or ring of atoms that are bonded together. The atoms do not have to all be directly bonded to each other, but rather may be directly bonded to as few as two other atoms in the 'loop'. Non-limiting examples of cyclic alkyls include benzene, toluene, cyclopentane, bisphenol and 1-chloro-3-ethylcyclohexane.

As used herein, the term "branched" is used as it is normally understood to a person of skill in the art and often refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl are tert-butyl and isopropyl.

As used herein, the term "unbranched" is used as it is normally understood to a person of skill in the art and often refers to a chemical entity that comprises a skeleton or main chain that does not split off into more that one contiguous chain. Non-limiting examples of unbranched alkyls are methyl, ethyl, n-propyl, and n-butyl.

As used herein, the term "substituted" is used as it is normally understood to a person of skill in the art and often refers to a chemical entity that has one chemical group replaced with a different chemical group that contains one or more heteroatoms. Unless otherwise specified, a substituted alkyl is an alkyl in which one or more hydrogen atom(s) is/are replaced with one or more atom(s) that is/are not hydrogen(s). For example, chloromethyl is a non-limiting example of a substituted alkyl, more particularly an example of a substituted methyl. Aminoethyl is another non-limiting example of a substituted alkyl, more particularly it is a substituted ethyl. The functional groups described herein may be substituted with, for example, and without limitation, 1, 2, 3, 4, 5, 6, 7, 8, 9 or 10 substituents.

As used herein, the term "unsubstituted" is used as it is normally understood to a person of skill in the art and often refers to a chemical entity that is a hydrocarbon and/or does not contain a heteroatom. Non-limiting examples of unsubstituted alkyls include methyl, ethyl, tert-butyl, and pentyl.

As used herein, the term "saturated" when referring to a chemical entity is used as it is normally understood to a person of skill in the art and often refers to a chemical entity that comprises only single bonds. Non-limiting examples of saturated chemical entities include ethane, tert-butyl, and $N^+H_3$.

As used herein the term "halogenated" is used as it would normally be understood to a person of skill in the art and refers to a moiety or chemical entity in which a hydrogen atom is replaced with a halogen atom such as chlorine, fluorine, iodine or bromine. For example, a chlorinated side chain of a naturally occurring amino acid refers to a side chain of a naturally occurring amino acid wherein one or more hydrogen atoms occurring in the side chain of the naturally occurring amino acid is replaced with one or more chlorine atoms.

Non-limiting examples of saturated $C_1$-$C_{10}$ alkyl may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{10}$ alkenyl may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{10}$ alkynyl may include ethynyl, propynyl, butynyl, pentynyl, hexynyl, heptynyl, octynyl, nonynyl and decynyl. Saturated $C_1$-$C_{10}$ alkyl, $C_2$-$C_{10}$ alkenyl or $C_2$-$C_{10}$ alkynyl may be, for example, and without limitation, interrupted by one or more heteroatoms which are independently nitrogen, sulfur or oxygen.

Non-limiting examples of the saturated $C_3$-$C_{10}$ cycloalkyl group may include cyclopropanyl, cyclobutanyl, cyclopentanyl, cyclohexanyl, cycloheptanyl, cyclooctanyl, cyclononanyl and cyclodecanyl. Non-limiting examples of the $C_3$-$C_{10}$ cycloalkenyl group may include cyclopropenyl, cyclobutenyl, cyclopentenyl, cyclohexenyl, cycloheptenyl, cyclooctenyl, cyclononanenyl and cyclodecanenyl. Non-limiting examples of $C_3$-$C_{10}$ cycloalkynyl may include cyclopropynyl, cyclobutynyl, cyclopentynyl, cyclohexynyl, cycloheptynyl and cyclooctynyl. Non-limiting examples of the $C_6$-$C_{10}$ aryl group may include phenyl (Ph), pentalenyl, indenyl, naphthyl, and azulenyl. The $C_{6-9}$ aryl-$C_{1-4}$ alkyl group may be, for example, and without limitation, a $C_{1-4}$ alkyl group as defined anywhere above having a $C_{6-9}$ aryl group as defined anywhere above as a substituent. The $C_{6-8}$ aryl-$C_{2-4}$ alkenyl group may be, for example, and without limitation, a $C_{2-4}$ alkenyl as defined anywhere above having a $C_{6-8}$ aryl group as defined anywhere above as a substituent. The $C_{6-8}$ aryl-$C_{2-4}$ alkynyl group may be, for example, and without limitation, a $C_{2-4}$ alkynyl group as defined anywhere above having a $C_{6-8}$ aryl group as defined anywhere above as a substituent. Non-limiting examples of the 4- to 10-membered non-aromatic heterocyclic group containing one or more heteroatoms which are independently nitrogen, sulfur or oxygen may include pyrrolidinyl, pyrrolinyl, piperidinyl, piperazinyl, imidazolinyl, pyrazolidinyl, imidazolydinyl, morpholinyl, tetrahydropyranyl, azetidinyl, oxetanyl, oxathiolanyl, phthalimide and succinimide. Non-limiting examples of the 5- to 10-membered aromatic heterocyclic group containing one or more heteroatoms which are independently nitrogen, sulfur or oxygen may include pyrrolyl, pyridinyl, pyridazinyl, pyrimidinyl, pirazinyl, imidazolyl, thiazolyl and oxazolyl.

Non-limiting examples of one to ten carbon substituted or unsubstituted acyl include acetyl, propionyl, butanoyl and pentanoyl. Non-limiting examples of $C_1$-$C_{10}$ alkoxy include methoxy, ethoxy, propoxy and butoxy.

The amino acid side chains of naturally occurring amino acids (as often denoted herein using "(aa)") are well known to a person of skill in the art and may be found in a variety of text books such as "Molecular Cell Biology" by James Darnell et al. Third Edition, published by Scientific American Books in 1995. Often the naturally occurring amino acids are represented by the formula $(NH_2)C(COOH)(H)(R)$, where the chemical groups in brackets are each bonded to the carbon not in brackets. R represents the side chain in this particular formula.

As used herein, the symbol

denotes the bond at a point of attachment between two chemical entities, one of which is depicted and the other of which is typically not depicted. For example,

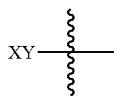

indicates that the chemical entity "XY" is bonded to another chemical entity via the point of attachment bond. Furthermore, the specific point of attachment to the non-depicted chemical entity may be specified by inference. For example The compound $CH_3$—$R^3$, wherein $R^3$ is H or

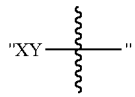

infers that when $R^3$ is "XY", the point of attachment bond is the same bond as the bond by which $R^3$ is depicted as being bonded to $CH_3$.

Examples of naturally occurring amino acid side chains or chlorinated versions thereof include: —$CH_2$—$CH(CH_3)$$CH_3$; —$CH_2$—$CH(CCl_3)CH_3$; —$CH_2$—$CH(CHCl_2)CH_3$; —$CH_2$—$CH(CH_2Cl)CH_3$; —$CH_2$—$CH(CCl_3)CH_2Cl$; —$CH_2$—$CH(CHCl_2)CH_2Cl$; —$CH_2$—$CH(CH_2Cl)CH_2Cl$; —$CH_2$—$CH(CCl_3)CHCl_2$; —$CH_2$—$CH(CHCl_2)CHCl_2$; —$CH_2$—$CH(CH_2Cl)CHCl_2$; —$CH_2$—$CH(CCl_3)CCl_3$; —$CH_2$—$CH(CHCl_2)CCl_3$; —$CH_2$—$CH(CH_2Cl)CCl_3$; —$CH(CH_3)CH_3$; —$CH(CCl_3)CH_3$; —$CH(CHCl_2)CH_3$; —$CH(CH_2Cl)CH_3$; —$CH(CCl_3)CH_2Cl$; —$CH(CHCl_2)CH_2Cl$; —$CH(CH_2Cl)CH_2Cl$; —$CH(CCl_3)CHCl_2$; —$CH(CHCl_2)CHCl_2$; —$CH(CH_2Cl)CHCl_2$; —$CH(CCl_3)CCl_3$; —$CH(CHCl_2)CCl_3$; —$CH(CH_2Cl)CCl_3$; —$CH(CH_3)$—$CH(CH_3)CH_3$; —$CH(CH_3)$—$CH(CCl_3)CH_3$; —$CH(CH_3)$—$CH(CHCl_2)CH_3$; —$CH(CH_3)$—$CH(CH_2Cl)CH_3$; —$CH(CH_3)$—$CH(CCl_3)CH_2Cl$; —$CH(CH_3)$—$CH(CHCl_2)CH_2Cl$; —$CH(CH_3)$—$CH(CH_2Cl)CH_2Cl$; —$CH(CH_3)$—$CH(CCl_3)CHCl_2$; —$CH(CH_3)$—$CH(CHCl_2)CHCl_2$; —$CH(CH_3)$—$CH(CH_2Cl)CHCl_2$; —$CH(CH_3)$—$CH(CCl_3)CCl_3$; —$CH(CH_3)$—$CH(CHCl_2)CCl_3$; and —$CH(CH_3)$—$CH(CH_2Cl)CCl_3$.

The embodiments involving the formulae as described herein include all possible stereochemical alternatives, including those illustrated or described herein.

In some embodiments, the compounds as described herein or acceptable salts thereof above may be used for systemic treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. In some embodiments, the compounds as described herein or acceptable salts thereof above may be used in the preparation of a medicament or a composition for systemic treatment of an indication described herein. In some embodiments, methods of systemically treating any of the indications described herein are also provided. Some aspects of this invention, make use of compositions comprising a compound described herein and a pharmaceutically acceptable excipients or carrier. In some embodiments, the prostate cancer is androgen-independent prostate cancer (also referred to as hormone refractory, castration resistant, androgen deprivation resistant, androgen ablation resistant, androgen depletion-independent, castration-recurrent, anti-androgen-recurrent). In some embodiments the prostate cancer is androgen-dependent or androgen-sensitive. Methods of treating any of the indications described herein are also provided. Such methods may include administering a compound as described herein or a composition of a compound as described herein, or an effective amount of a compound as described herein or composition of a compound as described herein to a subject in need thereof.

According to some embodiments, prodrugs of the compounds as described herein are also provided. Those of ordinary skill in the art will appreciate that prodrugs are compounds which are converted to the compounds as described herein or salts thereof under specified conditions. Specified conditions may include, for example, and without limitation, in vivo enzymatic or non-enzymatic means. Conversion of the prodrug may occur, for example, and without limitation, spontaneously, or it may be catalyzed, induced by another agent, or a change in a physical parameter or environmental parameter, for example, an enzyme, light, acid, temperature or pH. In some embodiments, the prodrug may have little or no pharmacological activity themselves, and then when converted into the compounds as described herein have the desired activity. Prodrugs may be prepared, for example, and without limitation, by converting appropriate functional groups (for example, a carboxylic acid functional group —COOH, an alcohol functional group —OH, or primary or secondary amine functional group) in the compounds as described herein with suitable moieties. Suitable moieties would be understood to and can be determined by those of ordinary skill in the art. For example, and without limitation, a prodrug can be formed by converting a primary or secondary amino functionality to an amide functionality. For example, and without limitation, a prodrug can be formed by converting a carboxylic acid functionality to an ester functionality, or converting an alcohol functionality to an ether functionality. A prodrug moiety may be, for example, and without limitation, a protecting group that acts to mask a functional group, a group that acts as a substrate for one or more active or passive transport mechanism, or a group that acts to impart or enhance a property of the compound, for example, solubility, bioavailability or localization. In some embodiments, the compounds as described herein or salts thereof may themselves be prodrugs of other compounds as described herein.

Compounds as described herein may be in the free form or in the form of a salt thereof. In some embodiments, compounds as described herein may be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid, an inorganic acid, an organic base or an inorganic base, or by anion exchange or cation exchange from other salts. Those skilled in the art will appreciate that preparation of salts may occur in situ during isolation and/or purification of the compounds or preparation of salts may occur by separately reacting an isolated and/or purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association with the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and/or amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions in accordance with this invention may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents include those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, $20^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition according to the invention includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (e.g. HIFU).

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances, however, such as in severe disease conditions, it may be necessary to administer substantial excesses of the compositions. Some compounds of this invention may be toxic at some concentrations. Titration studies may be used to determine toxic and non-toxic concentrations. Toxicity may be evaluated by examining a particular compound's or composition's specificity across cell lines using PC3 cells as a negative control that do not express AR. Animal studies may be used to provide an indication if the compound has any effects on other tissues. Systemic therapy that targets the AR will not likely cause major problems to other tissues since antiandrogens and androgen insensitivity syndrome are not fatal.

Compounds as described herein may be administered to a subject. As used herein, a "subject" may be a human, non-human primate, rat, mouse, cow, horse, pig, sheep, goat, dog, cat, etc. The subject may be suspected of having or at risk for having a cancer, such as prostate cancer, breast cancer, ovarian cancer or endometrial cancer, or suspected of having or at risk for having acne, hirsutism, alopecia, benign prostatic hyperplasia, ovarian cysts, polycystic ovary disease, precocious puberty, or age-related macular degeneration. Diagnostic methods for various cancers, such as prostate cancer, breast cancer, ovarian cancer or endometrial cancer, and diagnostic methods for acne, hirsutism, alopecia, benign prostatic hyperplasia, ovarian cysts, polycystic ovary disease, precocious puberty, or age-related macular degeneration and the clinical delineation of cancer, such as prostate cancer, breast cancer, ovarian cancer or endometrial cancer, diagnoses and the clinical delineation of acne, hirsutism, alopecia, benign prostatic hyperplasia, ovarian cysts, polycystic ovary disease, precocious puberty, or age-related macular degeneration are known to those of ordinary skill in the art.

Compounds described herein may be used for treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. Compounds described herein may be used for treatment of prostate cancer. Compounds described herein may be used for treatment of androgen-independent prostate cancer. Compounds described herein may be used for treatment of androgen-dependent prostate cancer. Compounds described herein may be used for preparation of a medicament for treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. Compounds described herein may be used for the preparation of a medicament for treatment of prostate cancer. Compounds described herein may be used for the preparation of a medicament for treatment of androgen-independent prostate cancer. Compounds described herein may be used for the preparation of a medicament for treatment of androgen-dependent prostate cancer. Compounds described herein may be used in a method for treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. The method may comprise administering to a subject in need thereof an effective amount of a compound described herein. Compounds described herein may be used in a method of treatment of prostate cancer, the method comprising administering to a subject in need thereof an effective amount of a compound described herein. Compounds described herein may be used in a method of treatment of androgen-independent prostate cancer, the method comprising administering to a subject in need thereof an effective amount of a compound described herein.

Compounds described herein may be used in a method of treatment of androgen-dependent prostate cancer, the method comprising administering to a subject in need thereof an effective amount of a compound described herein.

Compounds described herein may also be used in assays and for research purposes. Ligand-independent activation of the AR refers to transactivation of the AR in the absence of androgen (ligand) by, for example, stimulation of the cAMP-dependent protein kinase (PKA) pathway with forskolin (FSK). Some compounds and compositions of this invention may inhibit both FSK and androgen (e.g. R1881) induction of ARE-luciferase (ARE-luc). Such compounds may block a mechanism that is common to both ligand-dependent and ligand-independent activation of the AR. This could involve any step in activation of the AR including dissociation of heatshock proteins, essential posttranslational modifications (e.g., acetylation, phosphorylation), nuclear translocation, protein-protein interactions, formation of the transcriptional complex, release of co-repressors, and/or increased degradation. Some compounds and compositions of this invention may inhibit R1881 only and may interfere with a mechanism specific to ligand-dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism may be used to treat such conditions. Some compounds and compositions of this invention may only inhibit FSK induction and may be specific inhibitors to ligand-independent activation of the AR. These compounds and compositions may interfere with the cascade of events that normally occur with FSK and/or PKA activity or any downstream effects that may play a role on the AR (e.g. FSK increases MAPK activity which has a potent effect on AR activity). Examples may include an inhibitor of cAMP and or PKA or other kinases. Some compounds and compositions of this invention may induce basal levels of activity of the AR (no androgen or stimulation of the PKA pathway). Some compounds and compositions of this invention may increase induction by R1881 or FSK. Such compounds and compositions may stimulate transcription or transactivation of the AR. Some compounds and compositions of this invention may inhibit activity of the androgen receptor N-terminal domain (AR-NTD). Interleukin-6 (IL-6) also causes ligand-independent activation of the AR in LNCaP cells and can be used in addition to FSK. Compounds and compositions of this invention may interact with the AR-NTD or with another protein required for transactivation of the AR-NTD.

Compounds for use in the present invention may be obtained from medical sources or modified using known methodologies from naturally occurring compounds. In addition, methods of preparing or synthesizing compounds of the present invention will be understood by a person of skill in the art having reference to known chemical synthesis principles. For example, Willard et al, *J. Org. Chem.*, 1984, 49, 3489-3493 as well as Brantley et al, *Organic Letters*, 1999, vol 1, No. 13, 2165-2167 describe suitable synthetic procedures that may be considered and suitably adapted for preparing compounds of Formulas A-E.

General methodologies for chemical preparation of compounds of Formulas A-E are described in the following non-limiting exemplary schemes.

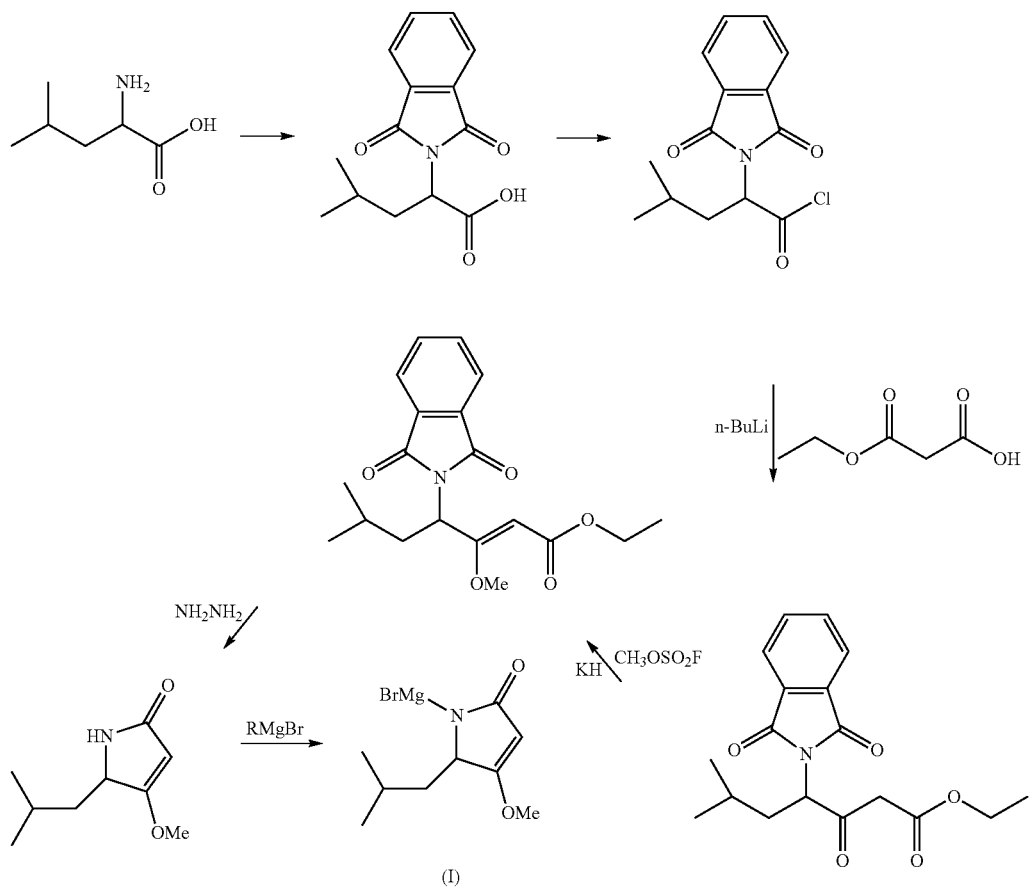

(I)

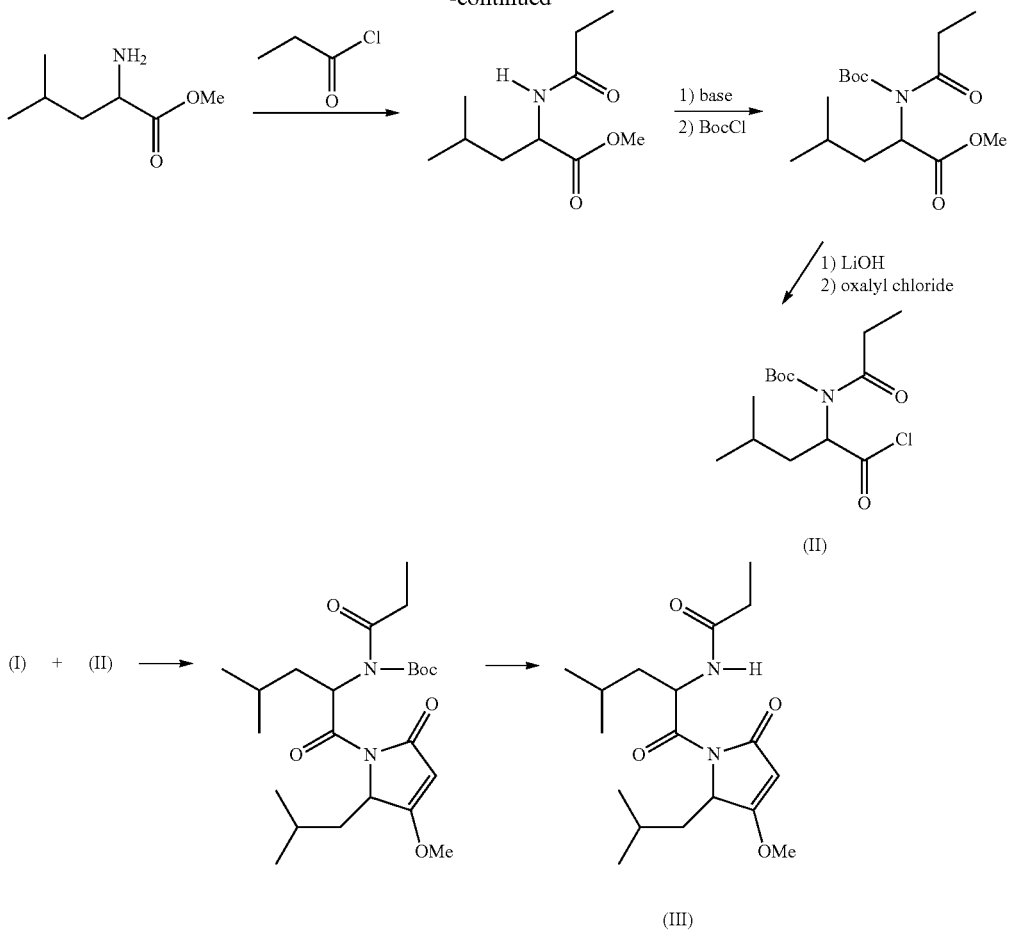
Compounds of Formulae A-E may also be prepared by the chemical methodologies described in the following non-limiting exemplary scheme.
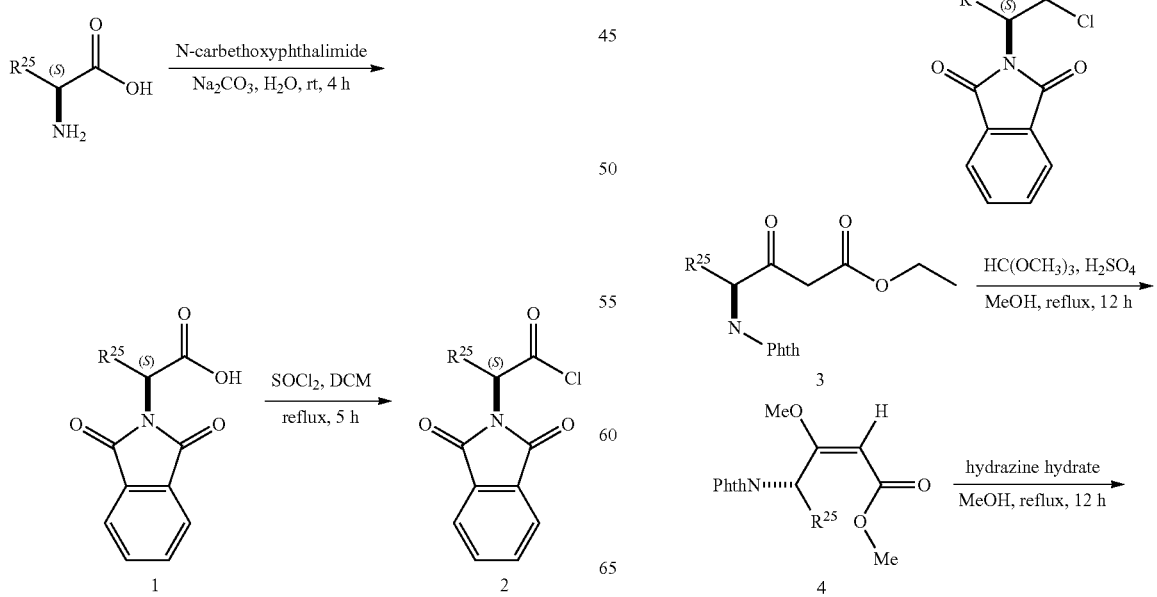

-continued
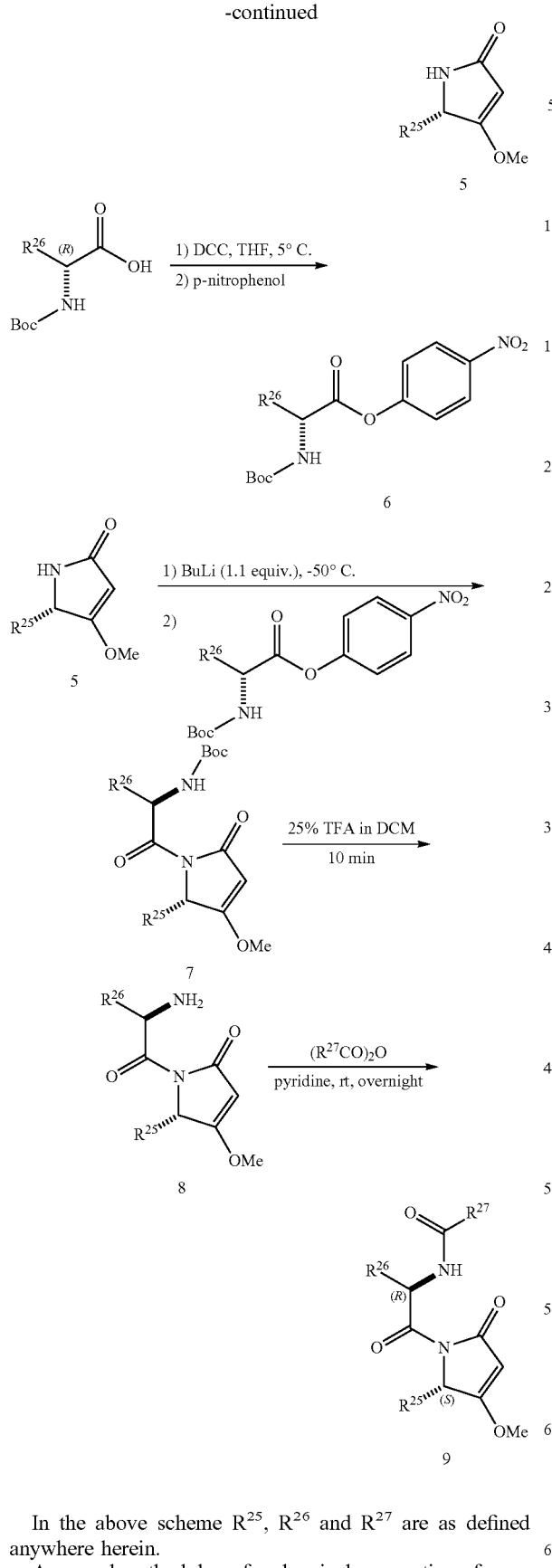
In the above scheme $R^{25}$, $R^{26}$ and $R^{27}$ are as defined anywhere herein.
A general methodology for chemical preparation of compounds of Formulae A-E are also described in the following exemplary non-limiting scheme using an unhalogenated leucine side chain as an example.
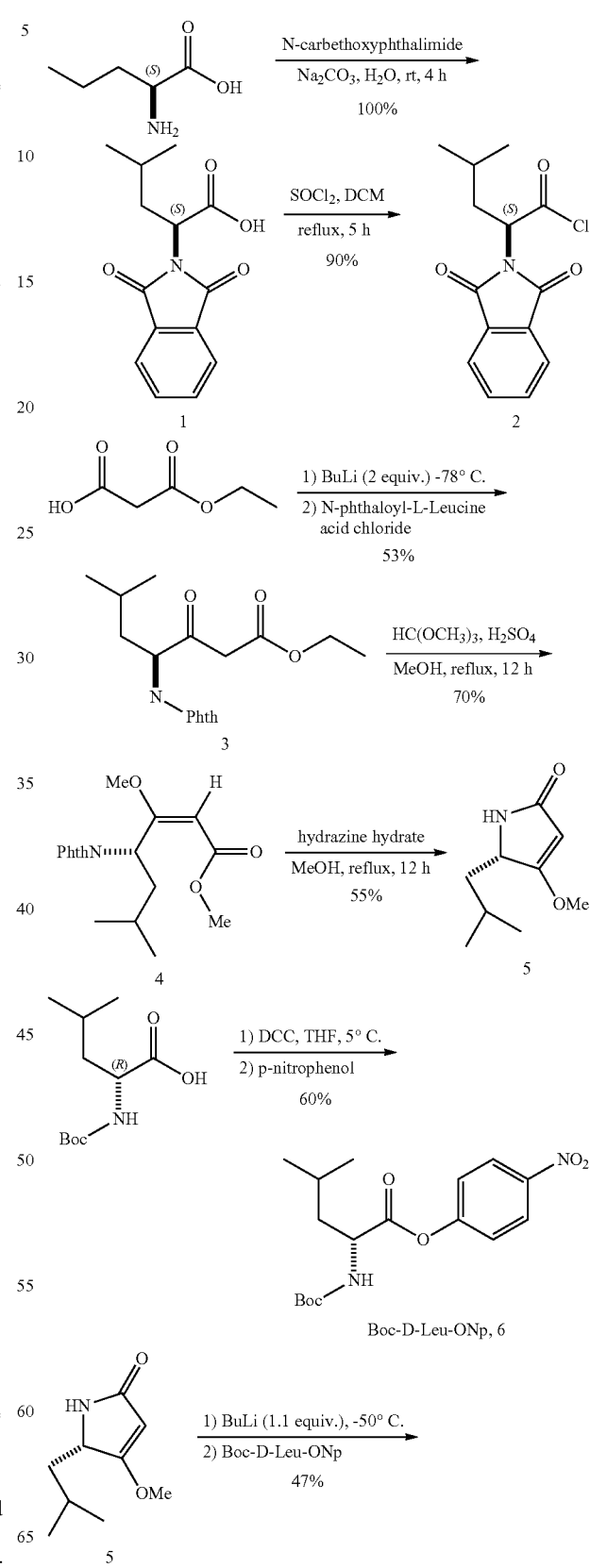

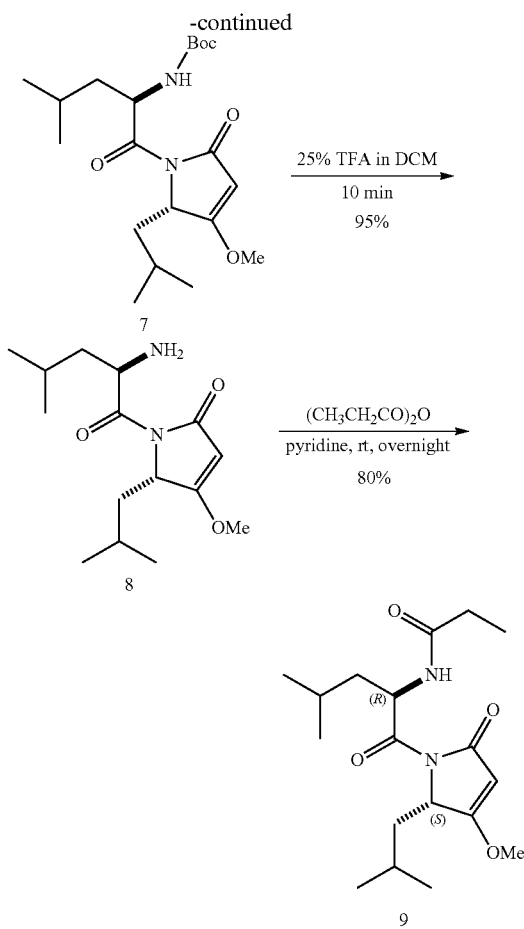

Methods for providing a halogenated version can be adapted from the art, including the procedure for providing a trichloromethyl substituent described in Brantley, S. et al., (1999) Organic Letters 1:2165-67.

In accordance with another embodiment, there is provided a method of preparing a compound of the formula (K):

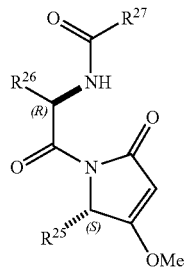

(K)

wherein: $R^{25}$ may be H or an amino acid side chain, except proline and phenylalanine or a one to ten carbon linear, branched, or non-aromatic cyclic, saturated or unsaturated, optionally substituted alkyl group, wherein the optional substituent may be selected from one or more of: oxo, COOH, COOR', CONH$_2$, CONHR', CONR'$_2$, R', OH, OR', F, Cl, Br, I, NH$_2$, NHR', NR'$_2$, CN, SH, SR', SO$_3$H, SO$_3$R', SO$_2$R', OSO$_3$R', and NO$_2$, and wherein R' may be an linear, or branched saturated and unsubstituted $C_1$-$C_{10}$ alkyl; $R^{26}$ may be H or an amino acid side chain, except proline and phenylalanine or a one to ten carbon linear, branched, or non-aromatic cyclic, saturated or unsaturated, optionally substituted alkyl group, wherein the optional substituent may be selected from one or more of: oxo, COOH, CONH$_2$, OH, F, Cl, Br, I, NH$_2$, SO$_3$H, and NO$_2$; and $R^{27}$ may be an optionally substituted Bu, Pr, Et, or Me, wherein the optional substituent may be selected from one or more of: oxo, COOH, OH, F, Cl, Br, I, NH$_2$, SO$_3$H, and NO$_2$.

In an embodiment, $R^{25}$ may be H or a one to ten carbon linear, branched, or non-aromatic cyclic, saturated or unsaturated, optionally substituted alkyl group, wherein the optional substituent may be selected from one or more of: oxo, COOH, R', OH, OR', F, Cl, Br, I, NH$_2$, NHR', NR'$_2$, CN, SH, SR', SO$_3$H, SO$_3$R', SO$_2$R', OSO$_3$R', and NO$_2$, and wherein R' may be an linear, or branched saturated and unsubstituted $C_1$-$C_{10}$, alkyl. In another embodiment, $R^{25}$ may be H or a one to ten carbon linear, or branched, saturated or unsaturated, optionally substituted alkyl group, wherein the optional substituent may be selected from one or more of: oxo, COOH, OH, F, Cl, Br, I, NH$_2$, and NO$_2$. Alternatively, $R^{25}$ may be H or a one to four carbon linear, or branched, saturated optionally substituted alkyl group, wherein the optional substituent may be selected from one or more of: oxo, OH, F, Cl, Br, I, and NH$_2$. In an embodiment, for example, and without limitation, $R^{25}$ may have the same definitions as $R^2$ described anywhere herein.

In an embodiment, $R^{26}$ may be H or a one to ten carbon linear, branched, or non-aromatic cyclic, saturated or unsaturated, optionally substituted alkyl group, wherein the optional substituent may be selected from one or more of: oxo, COOH, OH, F, Cl, Br, I, NH$_2$, SO$_3$H, and NO$_2$. Alternatively, $R^{26}$ may be H or a one to four carbon linear, or branched, saturated optionally substituted alkyl group, wherein the optional substituent may be selected from one or more of: oxo, OH, F, Cl, Br, I, and NH$_2$. In an embodiment, for example, and without limitation, $R^{26}$ may have the same definitions as $R^5$ described anywhere herein.

In an embodiment, $R^{27}$ may be an optionally substituted Bu, Pr, Et, or Me, wherein the optional substituent may be selected from one or more of: oxo, OH, F, Cl, Br, and I. Alternatively, $R^{27}$ may be an optionally substituted Bu, Pr, Et, or Me, wherein the optional substituent may be selected from one or more of: F, Cl, Br, and I. In an embodiment, for example, and without limitation, $R^{27}$ may have the same definitions as Z described anywhere herein.

According to one embodiment, the method may comprise, for example, and without limitation, mixing a compound of the formula (Q):

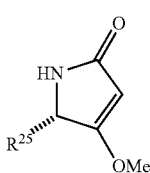

(Q)

wherein $R^{25}$ is as defined anywhere above, with n-BuLi to form a mixture, and reacting the mixture with a compound of the formula (S):

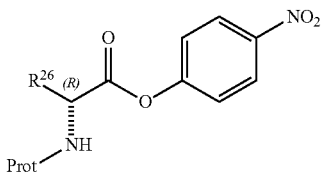

wherein $R^{26}$ is as defined anywhere above and Prot is a protecting group, to form a compound of the formula (T):

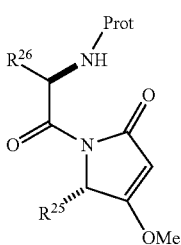

wherein $R^{25}$ and $R^{26}$ are as defined anywhere above and Prot is a protecting group; deprotecting the compound of the formula (T) to form a compound of the formula (U):

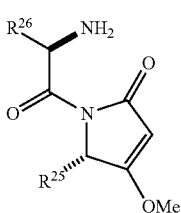

wherein $R^{25}$ and $R^{26}$ are as defined anywhere above; and reacting the compound of the formula (U) with a compound of the formula (V):

wherein $R^{27}$ is as defined anywhere above, in pyridine to form the compound of the formula (K).

According to one embodiment, the compound of the formula (Q) may be mixed with n-BuLi, for example, and without limitation, in a solvent. The solvent is not particularly limited and suitable solvents would be understood to and can be determined by those of ordinary skill in the art. In an embodiment, the solvent may be, for example, and without limitation, an aprotic solvent. In an embodiment, the solvent may be, for example, and without limitation, diethyl ether, dimethylformamide (DMF) or tetrahydrofuran (THF). In an embodiment, the solvent may be, for example, and without limitation, THF. Suitable temperatures for mixing the compound of the formula (Q) with n-BuLi would be understood to and can be determined by those of ordinary skill in the art. In an embodiment, the compound of the formula (Q) may be mixed with n-BuLi, for example, and without limitation, at a temperature of about −50° C. or less, and including any specific value within this range, such as for example, and without limitation, −50° C. In an embodiment, the temperature of mixing may be, for example, −50° C.

According to another embodiment, the mixture may be reacted with the compound of the formula (S), for example, and without limitation, in a solvent. The solvent is not particularly limited and suitable solvents would be understood to and can be determined by those of ordinary skill in the art. In an embodiment, the solvent may be, for example, and without limitation, an aprotic solvent. In an embodiment, the solvent may be, for example, and without limitation, diethyl ether, dimethylformamide (DMF) or tetrahydrofuran (THF). In an embodiment, the solvent may be, for example, and without limitation, THF.

The protecting group, Prot, of the compound of the formula (S) and of the compound of the formula (T) is not particularly limited and suitable amine protecting groups would be understood to and can be determined by those of ordinary skill in the art. In an embodiment, the protecting group may be, for example, and without limitation, a tert-butyloxycarbonyl (Boc) group or carbobenzyloxy (Cbz) group. In an embodiment, the protecting group may be, for example, and without limitation, Boc.

Suitable methods of deprotecting or removing the protecting group, Prot, from the compound of the formula (T) would be understood to and can be determined by those of ordinary skill in the art. In an embodiment, the compound of the formula (T) may be deprotected with, for example, and without limitation, a strong acid. In an embodiment, the compound of the formula (T) may be deprotected with, for example, and without limitation, trifluoroacetic acid (TFA). In an embodiment, deprotection of the compound of the formula (T) may occur, for example, and without limitation, in a solvent. In an embodiment, the solvent may be, for example, and without limitation, dichloromethane (DCM), DMF chloroform or THF. In an embodiment, the solvent may be, for example, and without limitation, DCM.

Suitable reaction temperatures for the compound of the formula (U) with the compound of the formula (V) would be understood to and can be determined by those of ordinary skill in the art. In an embodiment, the compound of the formula (U) may be reacted with the compound of the formula (V), for example, and without limitation, from about −20° C. or greater, to and including, about 100° C., and including any specific value within this range. In an embodiment, the compound of the formula (U) may be reacted with the compound of the formula (V), for example, and without limitation, at room temperature.

According to another embodiment, the method of preparing the compound of the formula (K) may further comprise, for example, and without limitation, mixing, in any order, a compound of the formula (R):

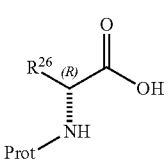

wherein $R^{26}$ and Prot are as defined anywhere above, with p-nitrophenol and with a carbodiimide-containing compound to form the compound of the formula (S):

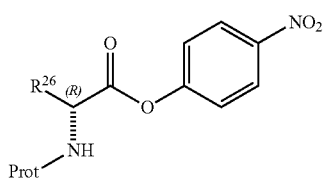

(S)

wherein $R^{26}$ and Prot are as defined anywhere above. The compound of the formula (R), p-nitrophenol and the carbodiimide-containing compound may be, for example, and without limitation, mixed in any order. In an embodiment, for example, and without limitation, the compound of the formula (R) may be mixed with p-nitrophenol before mixing with the carbodiimide-containing compound. In an embodiment, for example, and without limitation, the compound of the formula (R) may be mixed with the carbodiimide-containing compound before mixing p-nitrophenol. In an embodiment, for example, and without limitation, the compound of the formula (R), p-nitrophenol, and the carbodiimide-containing compound may be mixed at the same time. In an embodiment, the compound of the formula (S) may be formed, for example, and without limitation, in a solvent. Suitable solvents would be understood to and can be determined by those of ordinary skill in the art. In an embodiment, the compound of the formula (S) may be formed, for example, and without limitation, in DMF, THF, a dialkyl ether solvent, or a halogenated solvent. In an embodiment, the solvent may be, for example, and without limitation, DMF, DCM or THF. In an embodiment, the solvent may be, for example, and without limitation, THF. Suitable reaction temperatures for forming the compound of the formula (S) would be understood to and can be determined by those of ordinary skill in the art. In an embodiment, the reaction temperature for forming the compound of the formula (S) may be, for example, and without limitation, from about −20° C. or greater, to and including, about 50° C., and including any specific value within this range. In an embodiment, the reaction temperature for forming the compound of the formula (S) may be, for example, and without limitation, 5° C. In an embodiment, the carbodiimide-containing compound may be, for example, and without limitation, dicyclohexylcarbodiimide (DCC) or diisopropylcarbodiimide (DIPC). In an embodiment, the carbodiimide-containing compound may be, for example, and without limitation, DCC.

According to another embodiment, the method for preparing the compound of the formula (K) may further comprise, for example, and without limitation, reacting a compound of the formula (P):

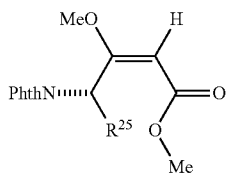

(P)

wherein $R^{25}$ is as defined anywhere above, with hydrazine monohydrate in MeOH to form the compound of the formula (Q):

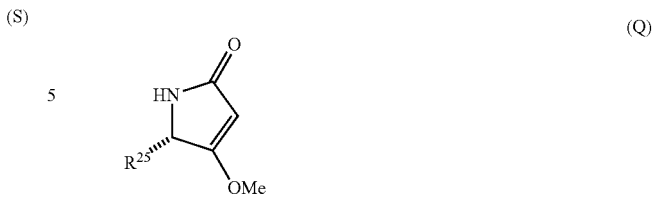

(Q)

wherein $R^{25}$ is as defined anywhere above.

According to another embodiment, the method for preparing the compound of the formula (K) may further comprise, for example, and without limitation, reacting a compound of the formula (O):

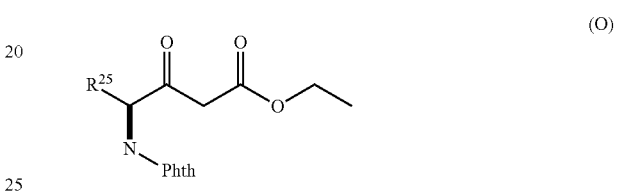

(O)

wherein $R^{25}$ is as defined in anywhere above, with trimethyl orthoformate in the presence of concentrated $H_2SO_4$ as a catalyst and in MeOH to form the compound of the formula (P):

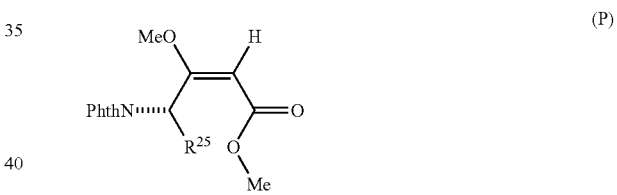

(P)

wherein $R^{25}$ is as defined anywhere above. In an embodiment, MeOH may be, for example, and without limitation, anhydrous MeOH.

According to another embodiment, the method for preparing the compound of the formula (K) may further comprise, for example, and without limitation, reacting a compound of the formula (M):

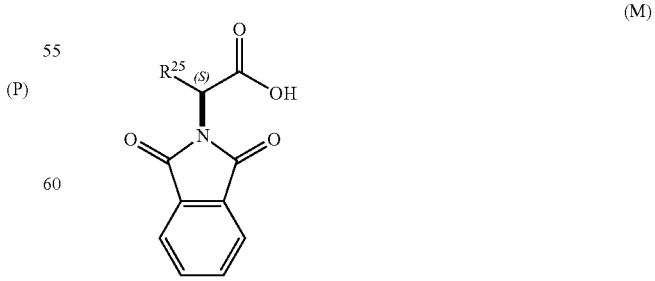

(M)

wherein $R^{25}$ is as defined anywhere above, with a chlorinating agent to form a compound of the formula (N):

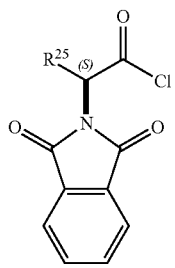

wherein R$^{25}$ is as defined anywhere above; and
reacting the compound of the formula (N) with a suspension, the suspension formed by mixing monoethyl malonate with an alkyllithium compound, to form the compound of the formula (O):

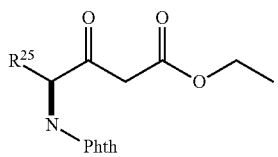

wherein R$^{25}$ is as defined anywhere above. In an embodiment, the chlorinating agent may be, for example, and without limitation, SOCl$_2$, oxalyl chloride or phosphorus trichloride (PCl$_3$). In an embodiment, the chlorinating agent may be, for example, and without limitation, SOCl$_2$. In an embodiment, the compound of the formula (M) may be, for example, and without limitation, reacted with the chlorinating agent in a solvent. Suitable solvents would be understood to and can be determined by those of ordinary skill in the art. In an embodiment, the solvent may be, for example, and without limitation, DCM, THF, DMF, chloroform or diethyl ether. In an embodiment, the solvent may be, for example, and without limitation, DCM. In an embodiment, the suspension may be formed by, for example, and without limitation, mixing monoethyl malonate with the alkyllithium compound in a solvent. In an embodiment, the alkyllithium compound may be, for example, and without limitation, ethyllithium, propyllithium, pentyllithium, phenyllithium or butyllithium (n-BuLi). In an embodiment, the alkyllithium compound may be, for example, and without limitation, n-BuLi. Suitable reactions temperatures for the compound of the formula (N) with the suspension would be understood to or can be determined by those of ordinary skill in the art. In an embodiment, the compound of the formula (N) may be, for example, and without limitation, reacted with the suspension at a temperature of about −50° C. or below and including any specific temperature within this range. In an embodiment, the compound of the formula (N) may be, for example, and without limitation, reacted with the suspension at a temperature of about −78° C.

According to another embodiment, the method for preparing the compound of the formula (K) may further comprise, for example, and without limitation, reacting a compound of the formula (L):

wherein R$^{25}$ is as defined anywhere above, with N-carbethoxyphthalimide in the presence of Na$_2$CO$_3$ and H$_2$O at about room temperature to form the compound of the formula (M):

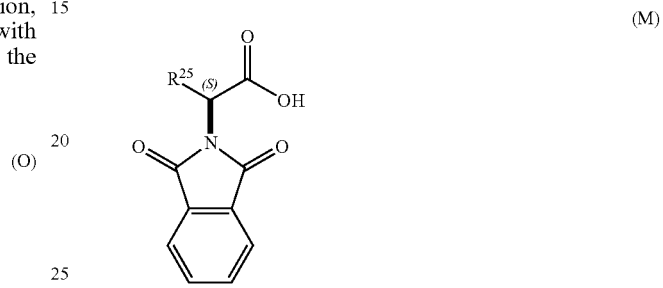

wherein R$^{25}$ is as defined anywhere above.

In some embodiments, there is further provided a compound of the formula (L), (M), (N), (O), (P), (Q), (R), (S), (T) or (U), wherein R$^{25}$, R$^{26}$ and R$^{27}$ are as defined anywhere above. In some embodiments, for example, and without limitation, R$^{25}$ and R$^{26}$ may independently be a mono-, di- or tri-chlorinated-methyl side chain of leucine.

Various alternative embodiments and examples of the invention are described herein. These embodiments and examples are illustrative and should not be construed as limiting the scope of the invention.

General Methodologies
Cell Lines, Androgen and Reporters

LNCaP cells were employed initially for all experiments because they are well-differentiated human prostate cancer cells in which ligand-independent activation of the AR by FSK has been characterized (Nazareth et al 1996 *J. Biol. Chem.* 271, 19900-19907; and Sadar 1999 *J. Biol. Chem.* 274, 7777-7783). LNCaP cells express endogenous AR and secrete prostate-specific antigen (PSA) (Horoszewicz et al 1983 *Cancer Res.* 43, 1809-1818). LNCaP cells can be grown either as monolayers in cell culture or as tumors in the well-characterized xenograft model that progresses to androgen independence in castrated hosts (Sato et al 1996 *J. Steroid Biochem. Mol. Biol.* 58, 139-146; Gleave et al 1991 *Cancer Res.* 51, 3753-3761; Sato et al 1997 *Cancer Res.* 57, 1584-1589; and Sadar et al 2002 *Mol. Cancer Ther.* 1(8), 629-637). PC3 human prostate cancer cells do not express functional AR (Kaighn et al 1978 Natl. *Cancer Inst. Monogr.* 49, 17-21) and were used to test specificity of compound for the AR. Small molecules that specifically target the AR-NTD should have no effect on PC3 cells. This means that they should not alter the proliferation of PC3 cells if they specifically block the AR to mediate their inhibitory effects. R1881 was employed since it is stable and avoids problems associated with the labile physiological ligand dihydrotestosterone (DHT). Reporter specificity may be determined using several alternative reporter gene constructs. Some well characterized ARE-driven reporter gene constructs that have been used extensively are the PSA (6.1 kb) enhance/promoter which contains several AREs and is highly inducible by androgens as well as by FSK (Ueda et al 2002 A *J. Biol. Chem.* 277, 7076-7085) and the ARR3-thymidine kinase (tk)-luciferase, which is an artificial reporter construct that contains three tandem repeats of the rat probasin ARE1 and ARE2 regions upstream of a luciferase reporter (Snoek et al 1996 *J. Steroid Biochem. Mol. Biol.* 59, 243-250). CMV-luc (no AREs and is constitutively active) was employed to determine that a compound does not have a general inhibitory effect on transcription.

Animal Models

Some experiments involved the use of SCID mice. SCID mice were chosen because the human cell lines and transplantable tumors survive in immunocompromised animals and SCID mice show the best take rates. All procedures have been approved by the University of British Columbia Committee for Animal Ethics and are annually reviewed. In the event of an emergency where proper animal care can not be provided, animals are euthanized at the discretion of the veterinarians or Animal Care Team. Veterinarians are responsible for inspections and consultation. The signed Animal Care Certificate specifically states, "The Animal Care Committee has examined and approved the use of animals for the above experimental project or teaching course, and have been given an assurance that the animals involved will be cared for in accordance with the principles contained in Care of Experimental Animals—A Guide for Canada, published by the Canadian Council on Animal Care."

Subcutaneous Xenografts

Six to eight-week old male athymic SCID mice were inoculated subcutaneously in the flank region via a 27-gauge needle with a 150 μl suspension of LNCaP or PC3 human prostate cancer cells ($1 \times 10^6$ cells). The inoculations took place while the animal was under isofluorane anaesthesia. The tumor take rate is approximately 75%. Mice bearing tumors of 100 mm³ were randomly assigned to treatment groups. Castration was performed as described below. Tumor volume (formula: L×W×H×0.5236) was measured in mice bearing LNCaP subcutaneous tumors that became palpable or visible and at least 40 mm³. The animals were monitored daily and tumors were measured every 5 days.

Duration of Experiments

Assessment of tumor volume (not to exceed 1000 mm³) was the criteria to determine termination of subcutaneous xenograft experiments.

Histology and Immunohistochemistry

For routine histology, major organs and xenografts were harvested upon completion of the experiment and were fixed in 10% neutral buffered formalin and then embedded in paraffin. Fixed sections were cut and stained with H&E. To determine possible effects of compounds on the proliferation rates and apoptosis in xenografts, Ki-67 immunostaining and the TUNEL assay was performed. Ki-67 immunostaining used the MIB-1 monoclonal antibody at an IgG concentration of 0.5 μg/ml (1:50) on processed tissue sections. Levels of AR were determined by immunohistochemistry or Western blot analysis.

Androgen Withdrawal to Induce Progression

Androgen withdrawal was completed by castration. Under isofluorane anaesthesia, a 5 mm vertical incision was used to gently withdraw the epididymal fat pad, to which the testis were attached, and to remove the testis from body. The cord connecting the testis to the blood supply was ligated with a suture, then cut. The cord was then returned to the abdominal cavity. Surgical suture was used to close the incision. To relieve pain, buprenorphine (0.05 mg/kg) was injected prior to surgery.

Xenograft and Organ Retrieval

All xenografts and major organs were retrieved for analyses. Retrieval was performed after sacrifice by cardiac arrest by $CO_2$ gas and the xenografts or organs were removed for immunohistochemistry analysis.

Euthanasia

Animals were sacrificed by cardiac arrest by $CO_2$ gas. This method is the policy set by the Animal Care Committee and is environmentally sensitive, effective, economic, and ethically approved.

EXAMPLES

Example 1

Assay Guided Fractionation and Isolation of Compounds

Specimens of *Dysidea* sp. were collected by hand using SCUBA at a depth of about 15 m near Palau Sintok, Karimunjawa archipelago, Indonesia, in June 2006 (N 55° 02.52, E 119° 19.48). The sponge was identified by Professor Rob van Soest, University of Amsterdam, and a voucher sample has been deposited at the Zoological Museum of Amsterdam (ZMA POR. 20602).

The freshly collected grey sponge (140 g) was initially preserved in MeOH and transported to Vancouver, British Columbia, Canada at room temperature over a 5 day period after which the sample was frozen. The sponge was cut into small pieces, immersed in and subsequently extracted repeatedly with MeOH (3×200 mL). The combined methanolic extracts were concentrated in vacuo and the resultant oil was then partitioned between EtOAc (4×5 mL) and $H_2O$ (20 mL). The combined EtOAc extract was evaporated to dryness and the resulting purple oil was chromatographed on Sephadex LH-20 using 4:1 MeOH/$CH_2Cl_2$ as eluent to give a fraction exhibited activity in the ARR3-luciferase assay. This material was fractionated further using silica gel flash chromatography, employing a step gradient from 19:1 hexanes/EtOAc to EtOAc. A fraction, eluting with 1:1 hexanes/EtOAc, was subjected to $C_{18}$ reversed-phase HPLC using a CSC-Inertsil 150A/ODS2, 5 μm 25×0.94 cm column, with 13:7 MeCN/$H_2O$ as eluent, to give 5 fractions. The least polar fraction contained pure sintokamide B (2) (4.4 mg) and the second most polar fraction contained pure dysamide D (7) (0.2 mg). The earliest eluting most polar fraction consisted of a mixture of sintokamide C (3) and sintokamide D (4). An additional HPLC step using the same column, but with 67:33 MeOH/$H_2O$ as eluent, gave clean sintokamide C (3) (0.4 mg) and sintokamide D (4) (0.3 mg). From the third eluting fraction, after a further HPLC fractionation with 70:30 MeOH/$H_2O$ as eluent, a pure sample of sintokamide E (5) (0.5 mg) was obtained along with a very small quantity of sintokamide A (1). From the last fraction using 3:1 MeOH/$H_2O$ sintokamide A (1) (29.6 mg). Also isolated were the known diketopiperazines, dysamide A (6) and B (7).

Optical rotations were measured using a Jasco P-1010 Polarimeter with sodium light (589 nm). UV spectra were recorded with a Waters 2487 Dual λ Absorbance Detector. The $^1H$ and $^{13}C$ NMR spectra were recorded on a Bruker AV-600 spectrometer with a 5 mm CPTCI cryoprobe. $^1H$ chemical shifts are referenced to the residual $C_6D_6$ signal (δ 7.15 ppm) and $^{13}C$ chemical shifts are referenced to the C₆D₆ solvent peak (δ 128.0 ppm). Low resolution ESI-QIT-MS were recorded on a Bruker-Hewlett Packard 1100 Esquire-LC system mass spectrometer. Merck Type 5554 silica gel plates and Whatman MKC18F plates were used for analytical thin layer chromatography. Reversed-phase HPLC purifications were performed on a Waters 600E System Controller liquid chromatography attached to a Waters 996 Photodiode Array Detector. All solvents used for HPLC were Fisher HPLC grade. The structures of (6) and (7) were confirmed by comparing their spectroscopic data with literature values (Su, J.-Y. et al. (1993) J. Nat. Prod. 56:637-642). Sintokamide A (1) gave crystals from MeOH that were suitable for x-ray diffraction analysis. An ORTEP diagram confirmed the constitution from the NMR analysis and revealed the absolute configuration 2S,4S,10R,16S. The structures of sintokamides B (2) to E (5) differ from sintokamide A (1) in the degree of chlorination at Me-18 or Me-19.

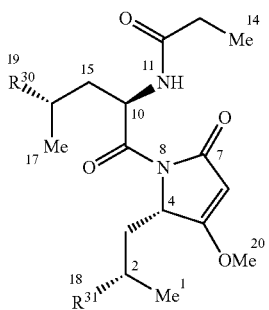

1 $R^{30}$ = CCl₃, $R^{31}$ = CHCl₂
2 $R^{30}$ = CCl₃, $R^{31}$ = CCl₃
3 $R^{30}$ = CHCl₂, $R^{31}$ = CHCl₂
4 $R^{30}$ = CCl₃, $R^{31}$ = CH₂Cl
5 $R^{30}$ = CCl₃, $R^{31}$ = CH₃

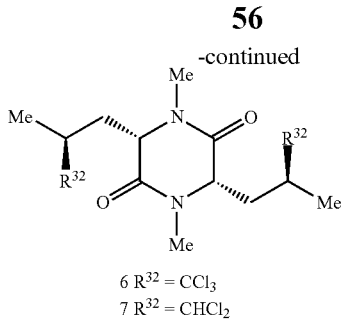

6 $R^{32}$ = CCl₃
7 $R^{32}$ = CHCl₂

Sintokamide A (1): Isolated as a clear oil; $[\alpha]^{25}{}_D$+35.9° (c 19.73, CH₂Cl₂); UV (CH₂Cl₂) $\lambda_{max}$ 224, 242 nm; ¹H, see Table 1; ¹³C and ¹⁵N NMR, see Table 2; positive ion HRESIMS [M+Na]⁺ m/z 531.0145 (calcd for C₁₈H₂₅N₂O₄Cl₅Na, 531.0154).

Sintokamide B (2): Isolated as a clear oil; $[\alpha]^{25}{}_D$+35.0° (c 2.93, CH₂Cl₂); UV (CH₂Cl₂) $\lambda_{max}$ 224, 242 nm; ¹H, see Table 1; ¹³C and ¹⁵N NMR, see Table 2; positive ion HRESIMS [M+Na]⁺ m/z 564.9738 (calcd for C₁₈H₂₄N₂O₄Cl₆Na, 564.9765).

Sintokamide C (3): Isolated as a clear oil; $[\alpha]^{25}{}_D$+58.7° (c 0.26, CH₂Cl₂); UV (CH₂Cl₂) $\lambda_{max}$ 224, 242 nm; ¹H, see Table 1; ¹³C and ¹⁵N NMR, see Table 2; positive ion HRESIMS [M+Na]⁺ m/z 497.0532 (calcd for C₁₈H₂₆N₂O₄Cl₄Na, 497.0544).

Sintokamide D (4): Isolated as a clear oil; $[\alpha]^{25}{}_D$+42.0° (c 0.20, CH₂Cl₂); UV (CH₂Cl₂) $\lambda_{max}$ 224, 242 nm; ¹H, see Table 1; ¹³C and ¹⁵N NMR, see Table 2; positive ion HRESIMS [M+Na]⁺ m/z 497.0532 (calcd for C₁₈H₂₆N₂O₄Cl₄Na, 497.0544).

Sintokamide E (5): Isolated as a clear oil; $[\alpha]^{25}{}_D$+47.6° (c 0.33, CH₂Cl₂); UV (CH₂Cl₂) $\lambda_{max}$ 224, 242 nm; ¹H, see Table 1; ¹³C and ¹⁵N NMR, see Table 2; positive ion HRESIMS [M+Na]⁺ m/z 463.0931 (calcd for C₁₈H₂₇N₂O₄Cl₃Na, 463.0934).

TABLE 1

¹H NMR Data for sintokamide A (1), sintokamide B (2), sintokamide C (3), sintokamide D (4) and sintokamide E (5) recorded with a 600 MHz spectrometer with a 5 mm CPTCI cryoprobe in C₆D₆.

| Atom # | | | | |
| --- | --- | --- | --- | --- |
| 1 | 2 | 3 | 4 | 5 |
| 1.02 d J = 6.7 Hz | 1.32 d J = 6.4 Hz | 0.98 d J = 6.7 Hz | 0.86 d J = 6.5 Hz | 0.84 d J = 6.2 Hz |
| 2.20 m | 2.86 m | 2.11 m | 1.82 | 1.71 |
| 1.97 | 2.31 dd | 1.93 dt | 1.83 | 1.71 |
| 1.78 ddd J = 13.9, 7.7, 5.3 Hz | 2.00 ddd J = 14.0, 9.8, 3.7 Hz | J = 14.0, 5.1 Hz 1.76 ddd J = 14.0, 7.9, 5.1 Hz | 1.65 | |
| 4.16 t J = 5.3 Hz | 4.25 dd J = 6.3, 3.7 Hz | 4.05 t J = 5.1 Hz | 4.18 t J = 4.7 Hz | 4.33 t J = 4.9 Hz |
| 4.47 s | 4.37 s | 4.32 s | 4.37 s | 4.41 s |
| 6.13 m | 6.14 dd J = 7.0, 7.0, 7.0 Hz | 6.15 ddd J = 10.1, 7.9, 3.5 Hz | 6.17 m | 6.27 m |
| 6.06 b | 5.65 bs | 5.73 bd J = 7.9 Hz | 5.78 bs | 5.88 bs |
| 1.95 m | 1.87 m | 1.83 m | 1.84 m | 1.83 m |
| 1.08 t J = 7.6 Hz | 1.04 t J = 7.5 Hz | 1.02 t J = 7.6 Hz | 1.04 t J = 7.6 Hz | 1.04 t J = 7.5 Hz |
| 2.84 dd, J = 13.8, 5.3 Hz | 2.85 m | 2.32 ddd, J = 14.2, 7.6, 3.5 Hz | 2.86 dd, J = 13.4, 5.5 Hz | 2.90 bdd, J = 14.2, 5.5 Hz |
| 1.65 ddd J = 13.8, 9.6, 6.7 Hz | 1.58 m | 1.36 ddd J = 14.2, 10.1, 5.3 Hz | 1.64 | 1.71 |

TABLE 1-continued $^1$H NMR Data for sintokamide A (1), sintokamide B (2), sintokamide C (3), sintokamide D (4) and sintokamide E (5) recorded with a 600 MHz spectrometer with a 5 mm CPTCI cryoprobe in $C_6D_6$.

| Atom # | 1 | 2 | 3 | 4 | 5 |
|---|---|---|---|---|---|
| | 3.09 m | 3.11 m | 2.49 m | 3.10 m | 3.13 m |
| | 1.42 d J = 6.7 Hz | 1.39 d J = 6.5 Hz | 1.17 d J = 6.7 Hz | 1.42 d J = 6.4 Hz | 1.45 d J = 6.4 Hz |
| | 5.45 d J = 2.8 Hz | | 5.37 d J = 2.8 Hz | 3.08 m | 0.84 d J = 6.2 Hz |
| | | | 6.42 d J = 2.2 Hz | 3.01 m | |
| | 2.79 s | 2.68 s | 2.69 s | 2.70 s | 2.72 s |

TABLE 2

$^{13}$C and $^{15}$N NMR Data for sintokamide A (1), sintokamide B (2), sintokamide C (3), sintokamide D (4) and sintokamide E (5) recorded with a 600 MHz spectrometer with a 5 mm CPTCI cryoprobe in $C_6D_6$.

| | $^{13}$C | | | | | $^{15}$N$^a$ | | | | |
|---|---|---|---|---|---|---|---|---|---|---|
| Atom # | 1 | 2 | 3 | 4 | 5 | 1 | 2 | 3 | 4 | 5 |
| 1 | 16.0 | 17.5 | 16.2 | 18.8 | 23.8 | | | | | |
| 2 | 40.8 | 52.0 | 40.7 | 32.2 | 24.6$^1$ | | | | | |
| 3 | 34.0 | 35.9 | 33.6 | 34.8 | 39.6$^1$ | | | | | |
| 4 | 57.5 | 57.7 | 57.3 | 57.9 | 58.3 | | | | | |
| 5 | 179.0 | 178.3 | 178.6 | 179.3 | 180.2 | | | | | |
| 6 | 93.7 | 93.8 | 93.7 | 93.5 | 93.4 | | | | | |
| 7 | 169.1 | 169.1 | 168.6 | 169.1 | 169.3 | | | | | |
| 8 | | | | | | −212.0 | −211.5 | −213.6 | −211.1 | −213.0 |
| 9 | 172.4 | 172.8 | 172.3 | 172.1 | 172.0 | | | | | |
| 10 | 51.8 | 51.8 | 51.3 | 51.8 | 51.7 | | | | | |
| 11 | | | | | | −262.6 | −263.0 | −265.6 | −262.8 | −264.0 |
| 12 | 173.0 | 172.9 | 173.1 | 172.7 | 172.6 | | | | | |
| 13 | 29.4 | 29.4 | 29.4 | 29.4 | 29.5 | | | | | |
| 14 | 9.9 | 9.8 | 9.9 | 9.8 | 9.8 | | | | | |
| 15 | 37.0 | 37.0 | 37.3 | 37.2 | 37.4 | | | | | |
| 16 | 53.3 | 53.4 | 41.8 | 53.3 | 53.3 | | | | | |
| 17 | 17.1 | 17.0 | 15.3 | 17.1 | 17.1 | | | | | |
| 18 | 78.7 | 106.1 | 78.7 | 50.5 | 22.6 | | | | | |
| 19 | 106.5 | 106.5 | 78.5 | 106.6 | 106.6 | | | | | |
| 20 | 58.0 | 57.6 | 57.8 | 57.7 | 57.6 | | | | | |

$^a$The $^{15}$N assignments were not calibrated with an external standard. The δ value has an accuracy of about 1 ppm in reference to $CH_3NO_2$ (0 ppm) and are assigned on the basis of $^{15}$NHSQC and $^{15}$NlrHMQC correlations.
$^1$Assignments within a column are interchangeable.

Example 2

Synthesis of N—((R)-1-((S)-2-isobutyl-3-methoxy-5-oxo-2,5-dihydro-1H-pyrrol-1-yl)-4-methyl-1-oxo-pentan-2-yl)propionamide N-phthalimide-L-leucine (1)

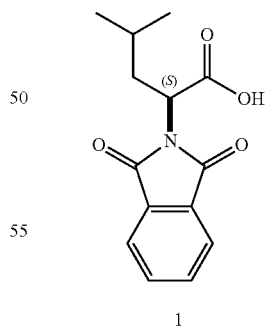

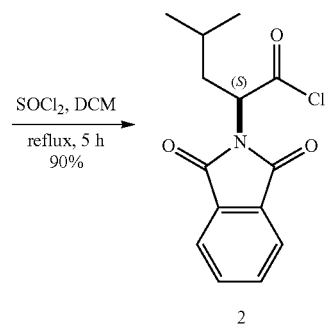

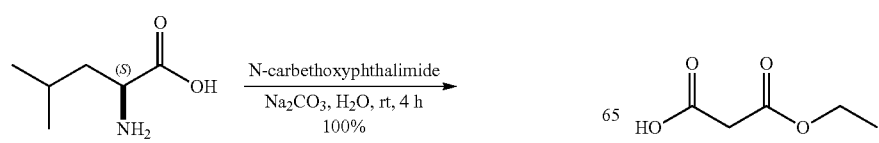

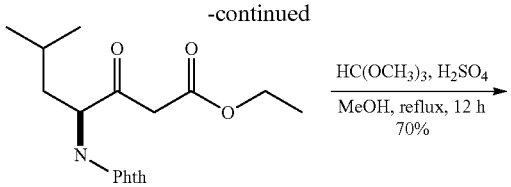

3

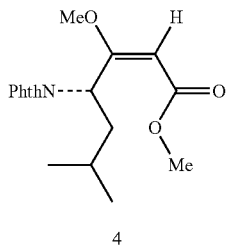

4

L-leucine (5.12 g, 39.1 mmol) and Na$_2$CO$_3$ (4.14 g, 39.1 mmol) were dissolved in 40 mL distilled H$_2$O. The solution was added N-carbethoxy-phthalimide (8.55 g, 39.1 mmol) and then stirred at room temperature for 2 h. The resultant clear solution was acidified using 6 N HCl to pH=0 and then extracted with hexanes (3×100 mL). The combined organic layers were dried in vacuo. Column chromatography on silica gel was applied eluting with hexanes/acetone (3:1) to get N-phthalimide-L-leucine (1) (10.2 g, 39.1 mmol, quantitative) as colorless oil. $^1$H NMR (400 MHz, CDCl$_3$) δ 0.92 (d, J=6.70 Hz, 3H), 0.94 (d, J=6.70 Hz, 3H), 1.37-1.60 (m, 1H), 1.95 (ddd, J=14.31, 10.05, 4.26 Hz, 1H), 2.36 (ddd, J=14.31, 10.05, 4.26 Hz, 1H), 4.99 (dd, J=11.57, 4.26 Hz, 1H), 7.73 (dd, J=5.48, 3.05 Hz, 2H), 7.85 (dd, J=5.48, 3.05 Hz, 2H), 11.32 (br. s., 1H); $^{13}$C NMR (75 MHz, CDCl$_3$) δ: 21.2, 23.3, 25.3, 37.2, 50.6, 123.8, 131.9, 134.4, 167.9, 176.0.

(S)-ethyl 6-methyl-4-phthalimido-3-oxoheptanoate (3)

N-Phthalimide-L-leucine (1) (550 mg, 2.11 mmol) in 4 mL dry DCM was refluxed with SOCl$_2$ (1.5 mL, 20.5 mmol) for 5 h. Excess SOCl$_2$ and solvent were evaporated under reduced pressure to produce N-phthalimide-L-leucinyl chloride (2) (535 mg, 1.91 mmol, 90%) as yellow oil and the product was used without further purification. Adding n-BuLi (3.7 mL, 2.0 M in hexanes, 7.4 mmol) dropwise to monoethyl malonate (450 mg, 3.41 mmol) in 5 mL dry THF at −70° C. gave a white suspension which was warmed up gently to −5° C. and then cooled back to −78° C. Acid chloride (2) (535 mg, 1.91 mmol) dissolved in 2 mL dry THF was added to this suspension all at once and the solution was further stirred for 20 min, then poured into a solution of 7 mL 1 N HCl and 10 mL ether and continue to stir for 5 min. The mixture was separated and the aqueous layer was extracted with ether (2×10 mL). The combined organic layers were washed with saturated NaHCO$_3$ (3×10 mL). After dried over anhydrous MgSO$_4$, the ethereal phase was evaporated in vacuo to give red oil. The crude was chromatographed over silica gel (hexanes/acetone=93:7) to give the homologous 1,3-diketone ester (3) (336 mg, 1.01 mmol, 53%) as yellow oil. $^1$H NMR (300 MHz, CDCl$_3$) δ: 0.93 (d, J=7.08 Hz, 3H), 0.95 (d, J=7.08 Hz, 3H), 1.23 (t, J=7.08 Hz, 3H), 1.37-1.57 (m, 1H), 1.91 (ddd, J=14.16, 10.05, 4.11 Hz, 1H), 2.24 (ddd, J=14.16, 10.05, 4.11 Hz, 1H), 3.52 (s, 2H), 4.14 (q, J=7.08 Hz, 2H), 5.00 (dd, J=11.31, 4.23 Hz, 1H), 7.76 (dd, J=5.60, 3.08 Hz, 2H), 7.88 (dd, J=5.60, 3.08 Hz, 2H); $^{13}$C NMR (75 MHz, CDCl$_3$) δ: 14.2, 21.3, 23.5, 25.3, 36.5, 46.5, 57.7, 61.9, 123.8, 131.9, 134.6, 166.6, 168.0, 198.3.

(S,E)-methyl 3-methoxy-6-methyl-4-phthalimido-hept-2-enoate (4)

The 1,3-diketone ethyl ester (3) (186 mg, 0.56 mmol) in 5 mL anhydrous MeOH was refluxed with trimethyl orthoformate (2.5 mL, 2.24 mmol) in the presence of a catalytic amount of conc. H$_2$SO$_4$ for 12 h. After adding ether (80 mL), the organic layer was washed with saturated NaHCO$_3$ (3×10 mL), dried over anhydrous MgSO$_4$, and then concentrated in vacuo. Flash chromatographing the crude over silica gel eluting with hexanes/acetone (9:1) gave ester exchanged E-enol ether product (4) (130 mg, 0.39 mmol) as yellow oil with 70% yield. $^1$H NMR (300 MHz, CDCl$_3$) δ: 0.96 (d, J=6.40 Hz, 3H), 1.00 (d, J=6.62 Hz, 3H), 1.49-1.60 (m, 1H), 1.67 (ddd, J=13.19, 11.48, 3.88 Hz, 1H), 2.66 (ddd, J=13.19, 11.48, 3.88 Hz, 1H), 3.63 (s, 3H), 3.74 (s, 3H), 5.05 (s, 1H), 6.33 (dd, J=11.42, 4.80 Hz, 1H), 7.71 (dd, J=5.48, 2.97 Hz, 2H), 7.83 (dd, J=5.48, 2.97 Hz, 2H); $^{13}$C NMR (100 MHz, CDCl$_3$) δ: 21.2, 23.4, 25.6, 38.3, 50.2, 51.4, 56.3, 91.2, 123.4, 132.2, 134.0, 167.0, 168.7, 172.3.

(S)-5-isobutyl-4-methoxy-1H-pyrrol-2(5H)-one (5)

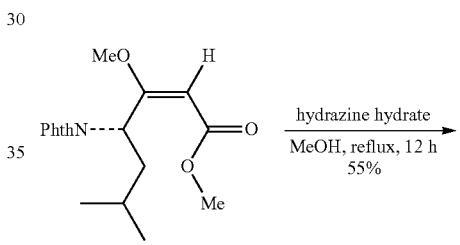

4

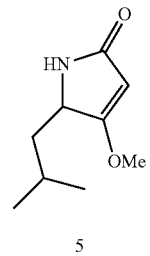

5

Enol ether (4) (53 mg, 0.16 mmol) in MeOH was refluxed with excess hydrazine monohydrate (2 mL) overnight. After removal of the solvent, the residue was dissolved in 50 mL DCM and added 40 mL distilled water. The organic phase was separated and the aqueous layer was extracted with DCM (3×40 mL). The combined organic layers were filtered over anhydrous Na$_2$SO$_4$ and then concentrated in vacuo. Flash chromatography on silica gel was applied using DCM/MeOH (200:1) as elute to obtain the tetramic acid (5) (15 mg, 0.088 mmol) as white solid with a yield of 55%. $^1$H NMR (400 MHz, CDCl$_3$) δ: 0.95 (d, J=2.05 Hz, 3H), 0.97 (d, J=2.05 Hz, 3H), 1.38 (td, J=9.22, 4.78 Hz, 1H), 1.64 (td, J=9.22, 4.78 Hz, 1H), 1.70-1.83 (m, 1H), 3.79 (s, 3H), 4.06 (dd, J=9.56, 3.41 Hz, 1H), 5.00 (d, J=1.02 Hz, 1H), 6.24 (br. s., 1H); $^{13}$C NMR (100 MHz, CDCl$_3$) δ: 22.0, 23.6, 25.6, 41.6, 56.2, 58.4, 93.3, 174.5, 179.2; ESIMS [M+H]$^+$ 170.2.

(R)-4-nitrophenyl 2-(tert-butoxycarbonylamino)-4-methylpentanoate (6)

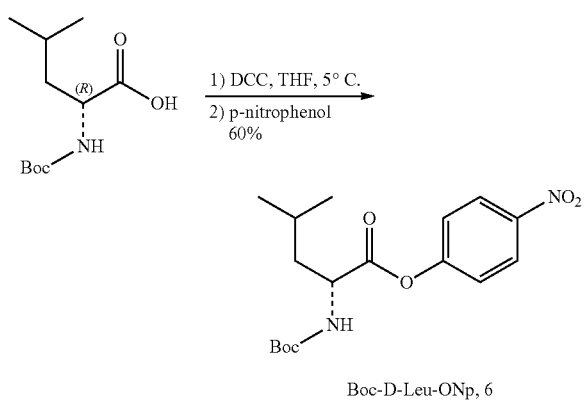

Boc-D-Leucine (462 mg, 2.0 mmol) in 5 mL dry THF was added to p-nitrophenol (294 mg, 2.1 mmol) and the mixture was then treated with DCC (413 mg, 2.0 mmol) at 5° C. and then stirred at room temperature overnight. The solution was filtered and then dried in vacuo. The crude was chromatographed over silica gel (hexanes/acetone=3:2) to give Boc-D-Leu-ONp (6) (420 mg, 1.2 mmol) as colorless oil with a yield of 60%. $^1$H NMR (400 MHz, CDCl$_3$) δ: 1.02 (d, J=2.05 Hz, 3H), 1.04 (d, J=2.05 Hz, 3H), 1.47 (s, 9H), 1.61-1.71 (m, 1H), 1.75-1.86 (m, 2H), 4.52 (br. s., 1H), 4.94 (d, J=6.14 Hz, 1H), 7.31 (d, J=9.22 Hz, 2H), 8.28 (d, J=9.22 Hz, 2H); $^{13}$C NMR (100 MHz, CDCl$_3$) δ21.9, 23.0, 25.1, 28.5, 41.3, 52.7, 80.6, 122.5, 125.4, 145.6, 155.5, 155.7, 171.6.

tert-butyl (R)-1-((S)-2-isobutyl-3-methoxy-5-oxo-2,5-dihydro-1H-pyrrol-1-yl)-4-methyl-1-oxopentan-2-ylcarbamate (7)

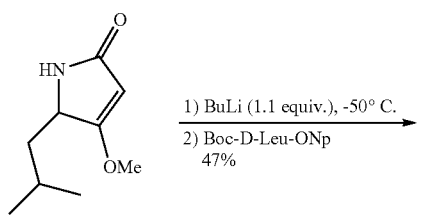

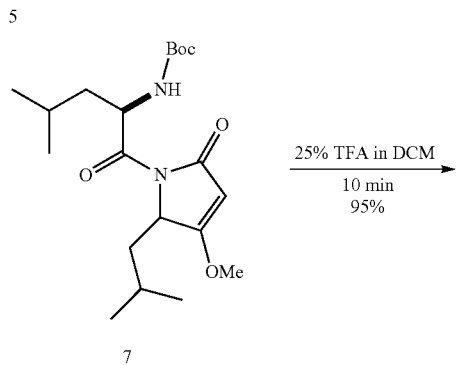

The tetramic acid (5) (11.2 mg, 0.066 mmol) in 2 mL dry THF was treated with n-BuLi (32 μl, 1.60 M, 0.066 mmol) at −50° C. for 10 min whereafter Boc-D-Leu-ONp (6) (25.6 mg, 0.073 mmol) in 2 mL dry THF was added dropwise in 15 min. The mixture was further stirred for 10 min and quenched with 0.1 mL AcOH and evaporated in vacuo. Pure coupling product (7) (12.0 mg, 0.031 mmol) as white powder was obtained after a flash chromatography on silica gel (hexanes/ethyl acetate=3:1), the yield is 47%. $^1$H NMR (400 MHz, CDCl$_3$) δ: 0.89 (d, J=5.87 Hz, 3H), 0.93 (d, J=6.60 Hz, 6H), 1.04 (d, J=6.36 Hz, 3H), 1.32-1.40 (m, 1H), 1.46 (s, 9H), 1.75-1.88 (m, 6H), 4.58 (t, J=5.12 Hz, 1H), 5.04 (s, 3H), 5.10 (br.d, J=8.07 Hz, 1H), 5.45 (td, J=2.93, 1.96 Hz, 1H).

(S)-1-((R)-2-amino-4-methylpentanoyl)-5-isobutyl-4-methoxy-M-pyrrol-2(5H)-one (8)

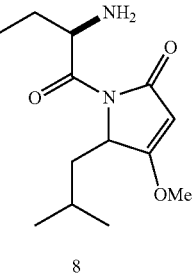

The Boc-protected coupling product (7) (5.0 mg, 0.013 mmol) in 1 mL dry DCM was added 1 mL 33% TFA's DCM solution and stirred for 10 min. The solvent was neutralized with 10 mL 25% ammonia solution and extracted using DCM (3×10 mL). The organic phase was combined and dried over anhydrous Na$_2$SO$_4$ and concentrated with reduced pressure. The crude was flash chromatographed over silica gel eluting with DCM/MeOH (98:2) to obtain deprotected product (8) (3.3 mg, 0.012 mmol) as white powder with a yield of 95%. $^1$H NMR (400 MHz, CDCl$_3$) δ: 0.90 (d, J=6.43 Hz, 3H), 0.93 (d, J=2.92 Hz, 3H), 0.95 (d, J=2.63 Hz, 3H), 0.98 (d, J=6.72 Hz, 3H), 1.32 (td, J=8.99, 4.82 Hz, 1H), 1.54 (ddd, J=13.45, 9.06, 4.38 Hz, 1H), 1.76 (td, J=13.37, 6.58 Hz, 1H), 1.83-1.92 (m, 2H), 3.87 (s, 3H), 4.55 (dd, J=9.50, 4.24 Hz, 1H), 4.60 (t, J=5.12 Hz, 1H), 5.05 (s, 1H); ESIMS [M+H]$^+$ 283.3.

N—((R)-1-((S)-2-isobutyl-3-methoxy-5-oxo-2,5-dihydro-1H-pyrrol-1-yl)-4-methyl-1-oxopentan-2-yl)propionamide (9)

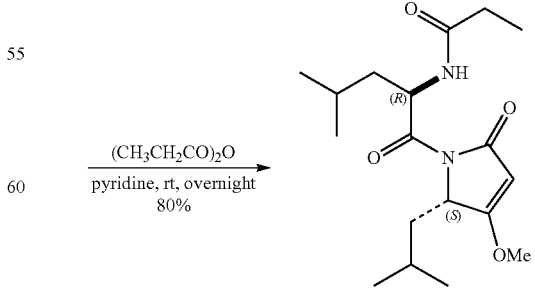

Stir amino-free compound (8) (1.0 mg, 0.0035 mmol) with propionyl anhydride (1.4 µl, 0.011 mmol) in 2 mL dry pyridine at room temperature for 12 h. The solution was acidified with 10 mL 1 N HCl and the extracted into ethyl acetate (3×10 mL). The combined organic phase was filtered over anhydrous $MgSO_4$ and evaporated in vacuo. The N-propionylated product (9) (1.0 mg, 0.0029 mmol) was obtained after flash chromatography over silica gel (hexanes/ethyl acetate=3:1) as colourless solid with a yield of 80%. $^1H$ NMR (600 MHz, $CDCl_3$) δ: 0.88 (d, J=6.24 Hz, 3H), 0.92 (d, J=6.60 Hz, 6H), 1.05 (d, J=6.60 Hz, 3H), 1.17 (t, J=7.52 Hz, 3H), 1.40 (dt, J=6.97, 3.67 Hz, 1H), 1.59 (dt, J=6.97, 3.67 Hz, 1H), 1.75-1.79 (m, 1H), 1.80-1.83 (m, 3H), 2.25 (q, J=7.70 Hz, 2H), 3.87 (s, 3H), 4.57 (dd, J=6.24, 4.03 Hz, 1H), 5.05 (s, 1H), 5.75 (ddd, J=10.73, 9.08, 2.93 Hz, 1H), 6.04 (d, J=8.80 Hz, 1H); $^{13}C$ NMR (150 MHz, $CDCl_3$) δ10.0, 21.4, 22.7, 23.8, 23.9, 24.3, 25.2, 29.9, 39.3, 41.7, 51.6, 58.9, 58.9, 93.6, 169.6, 173.1, 173.3, 181.0.

In all, there are 9 steps in this synthesis and an overall yield of 3.9% was observed.

Example 3

Biological Activity of Sintokamide A

Screen to Identify CB3.1

A high throughput screen was used to identify active compounds that inhibited the activity of the androgen receptor (AR). The initial screen was a cell-based assay comprising of LNCaP cells stably expressing the ARR3-luciferase reporter. The assay consisted of activating the endogenous AR using a synthetic androgen, R1881, and measuring levels of luciferase activity. Marine sponge extracts were added 1 hr prior to the addition of R1881 to the cells and incubated for an additional 48 h before harvesting and measuring luciferase activity in the cell lysates. Marine sponge extract 06-80 strongly inhibited androgen-induced luciferase activity (FIG. 1A).

Cytotoxicity

Figure 1B:
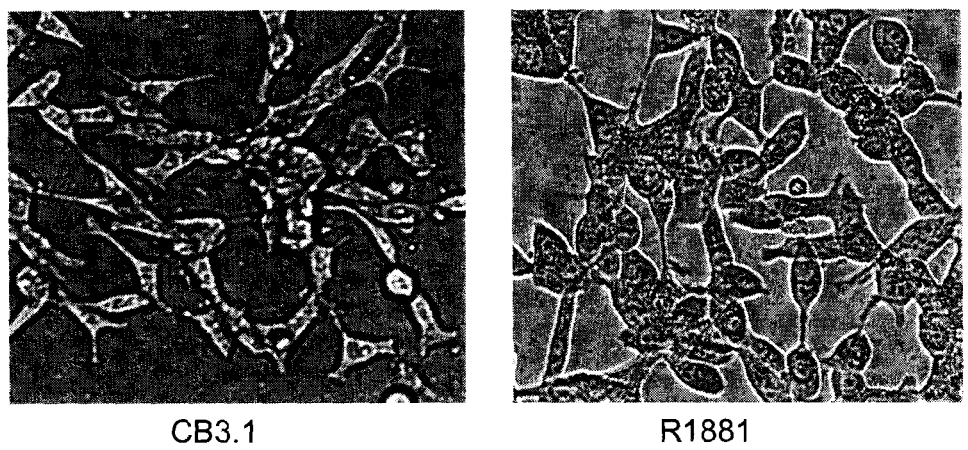
FIG. 1B shows micrographs of the morphology of LNCaP cells treated with the active isolated compound from 06-80 called CB3.1 (10 µg/ml) or R1881 (1 nM) and DMSO (vehicle for compounds) for 48 hrs and visualized with aid of an inverted microscope.

From this extract, the pure active compound, Sintokamide A (CB3.1) was isolated and to ensure that the inhibitory effect of CB3.1 was not due to generally cytotoxicity, cell morphology of LNCaP cells was examined. FIG. 1B shows that LNCaP cells treated for 48 h with CB3.1 (10 µM) have no obvious signs of toxicity indicating that the inhibitory effect on AR activation was not simply due to general cytotoxicity. Cells treated with R1881 are also shown to provide an indication of cell number and for comparison. CB3.1 did not decrease androgen-induced luciferase activity by a mechanism involving non-specific toxicity.

Transactivation of the AR NTD

Figure 3A:
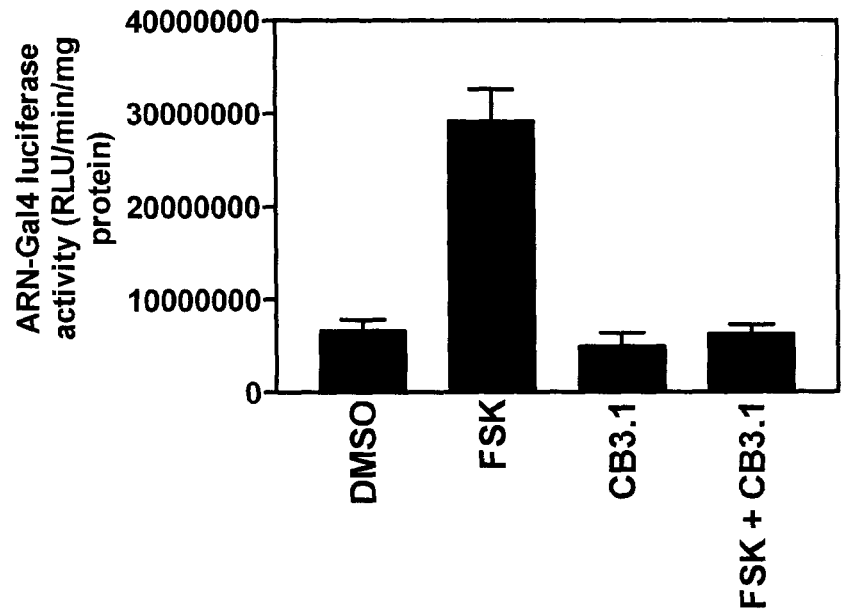
FIG. 3A shows a bar graph of Sintokamide A blockage of FSK-induced transactivation of the AR NTD. Sintokamide A (CB3.1) (5 µg/ml) was tested for its ability to inhibit the AR NTD. LNCaP cells were co-transfected with the expression vector for Gal4DBD-AR$_{1-558}$ and the complimentary 5XGal4UAS-luciferase reporter. Induction of this reporter by FSK is a measure of transactivation of the Gal4DBD-AR$_{1-558}$ fusion protein (Sadar 1999 J. Biol. Chem. 274, 7777-7783). R1881 does not induce such assays (binds to the ligand-binding domain (LBD) of the AR which is not present in the Gal4DBD-AR$_{1-558}$ chimera) and therefore was not used.

To determine if CB3.1 blocked transactivation of the AR NTD, LNCaP cells were transfected with the plasmids for the AR NTD-Gal4DBD chimera protein and the Gal4-luciferase reporter and pretreated for 1 hr with CB3.1 (5 µg/ml) prior to addition of forskolin (FSK 50 µM) for an additional 24 h (see: Sadar et al. (1999) J. Biol. Chem. 274:7777-83). CB3.1 reduced FSK-induced transactivation of the AR NTD to baseline levels (see FIG. 3A) and inhibited transactivation of the AR NTD.

Steroid Receptor Specificity

Sequence similarities of amino acids in the AR with related human steroid receptors (glucocorticoid receptor (GR) and progesterone receptor (PR)) are significant in some domains such as the DNA-binding-domain (DBD). Although the AR-NTD shares less than 15% homology with the PR and GR, these receptors do interact with some of the same proteins such as SRC-1 (steroid receptor coactivator-1). Therefore, reporter gene assays were used to determine if candidate compounds that block AR activity have any effect on GR and PR transcriptional activity. Cells were co-transfected with expression plasmids for full-length hGR and PRβ and the relative reporter (i.e., pGR-Luc or PRE-E1b-Luc reporters). Cells were then treated with ethanol vehicle, dexamethasone (GR), 4-pregnene-3,20 dione (progesterone) (PR) followed by measurement of luciferase activity. CB3.1 (5 µg/ml) strongly inhibited AR activity as measured using the PSA (6.1) luciferase reporter (see FIG. 2A), but did not inhibit PRE-luciferase or GRE-luciferase activities in response to ligand (see FIGS. 2B-C) The data shows that CB3.1 does not alter the transactivation of other steroid receptors and does not have non-specific and general effects on transcription or translation since it did not inhibit induction of the GR and PR luciferase reporters. CB3.1 appears to be specific to the AR and suggests that fewer side effects from systemic delivery would be expected.

Proliferation Assay

Figure 3B:
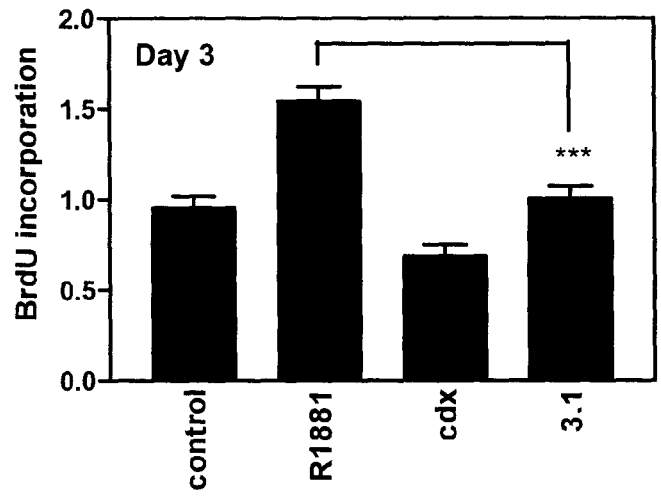
FIG. 3B shows a bar graph illustrating Sintokamide A (CB3.1) blockage of androgen-dependent proliferation of LNCaP cells treated with bicalutamide (BIC, 10 µM) or CB3.1 (5 µg/mL) for 1 hr before the addition of R1881 (0.1 nM). Cells were harvested and measured for BrdU incorporation after 3 days of treatment with androgen. p=0.0001 between CB3.1 plus R1881 and only R1881-treated.
Figure 3C:
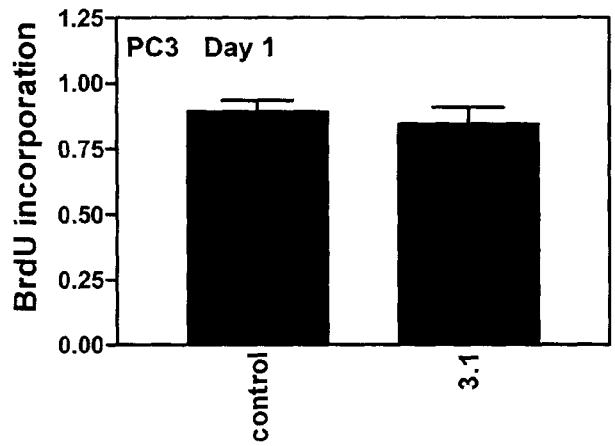
FIG. 3C shows a bar graph illustrating Sintokamide A (CB3.1) failure to block proliferation of PC3 cells. Cells were treated with vehicle (DMSO), CB3.1 (5 µg/mL) for 1 days before harvesting and measurement of BrdU incorporation. Bars represent the mean±SEM (n=6).

CB3.1 reduced proliferation of LNCaP cells treated with androgen (R1881). LNCaP cells were pretreated for 1 hr with bicalutamide (cdx, 10 µM, positive control) or CB3.1 (5 µg/ml) prior to addition of 0.1 nM R1881. BrdU incorporation was measured 3 days later to indicate changes in proliferation in response to androgen (see FIG. 3B). 0.1 nM R1881 increased proliferation over control (vehicle for R1881 and small molecules). CB3.1 was as effective in blocking androgen-induced proliferation. CB3.1 did not block proliferation of PC3 human prostate cancer cells (see FIG. 3C) that do not express AR (Kaighn et al 1978 Natl. Cancer Inst. Monogr. 49, 17-21) and thus do not rely on the AR for growth and survival.

Example 4

Sintokamides Inhibit Androgen-Induced Levels of PSA mRNA in LNCaP Cells

Figure 4:
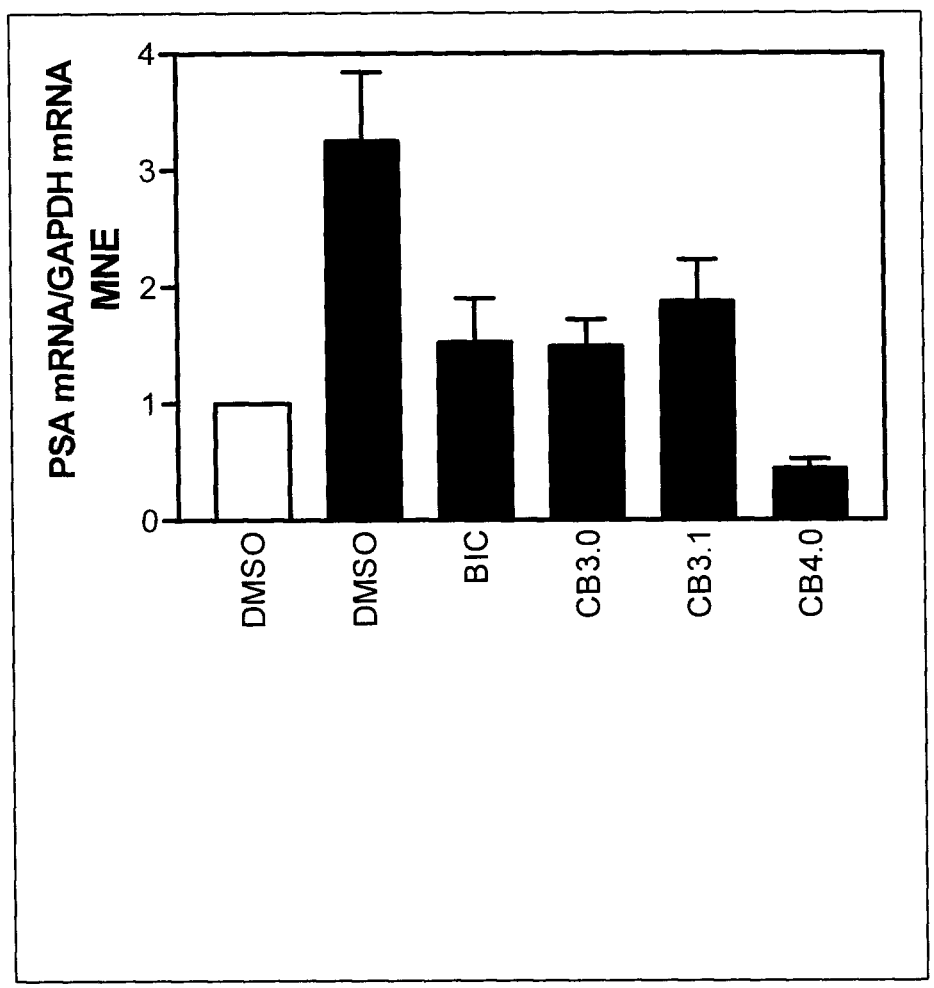
FIG. 4 shows a bar graph demonstrating that Sintokamides inhibit androgen-induced levels of PSA mRNA in LNCaP cells. Cells were pre-treated for 1 hour with bicalutamide (BIC, 10 µM) or 10 µg/ml of each of the compounds (CB3.0 (Dysamide A), CB3.1 (Sintokamide A), and CB4.0 (Sintokamide B) in DMSO carrier) before the addition of the synthetic androgen R1881 (1 nM) and then incubated for an additional 16 hours before harvesting and isolating total RNA. Levels of PSA mRNA were measured by quantitative real-time (qRT)-PCR and normalized to levels of GAPDH mRNA (housekeeping gene). White bar: no R1881. Black bars: R1881 (1 nM). MNE: mean normalized expression. DMSO (no R1881) was arbitrarily set at 1.0 for each individual experiment. Bars represent the mean±SE from 3 separate experiments using triplicate technical samples from each experiment.

PSA is an androgen-regulated gene containing several well-characterized androgen response elements (AREs) in the enhancer and promoter regions. Levels of PSA mRNA are induced by androgen by a mechanism dependent androgen receptor. To test if sintokamides would also block endogenous gene expression induced by androgen, levels of PSA mRNA were measured in response to the synthetic androgen R1881. R1881 induced levels of PSA mRNA at least 3-fold (see FIG. 4) and this could be blocked by the antiandrogen, bicalutamide as well as by each of the sintokamides. This data is consistent with sintokamides blocking the transcriptional activity of the androgen receptor.

Example 5

Inhibition of R1881 Induction of PSA (6.1)-Luciferase by Sintokamides

Figure 5:
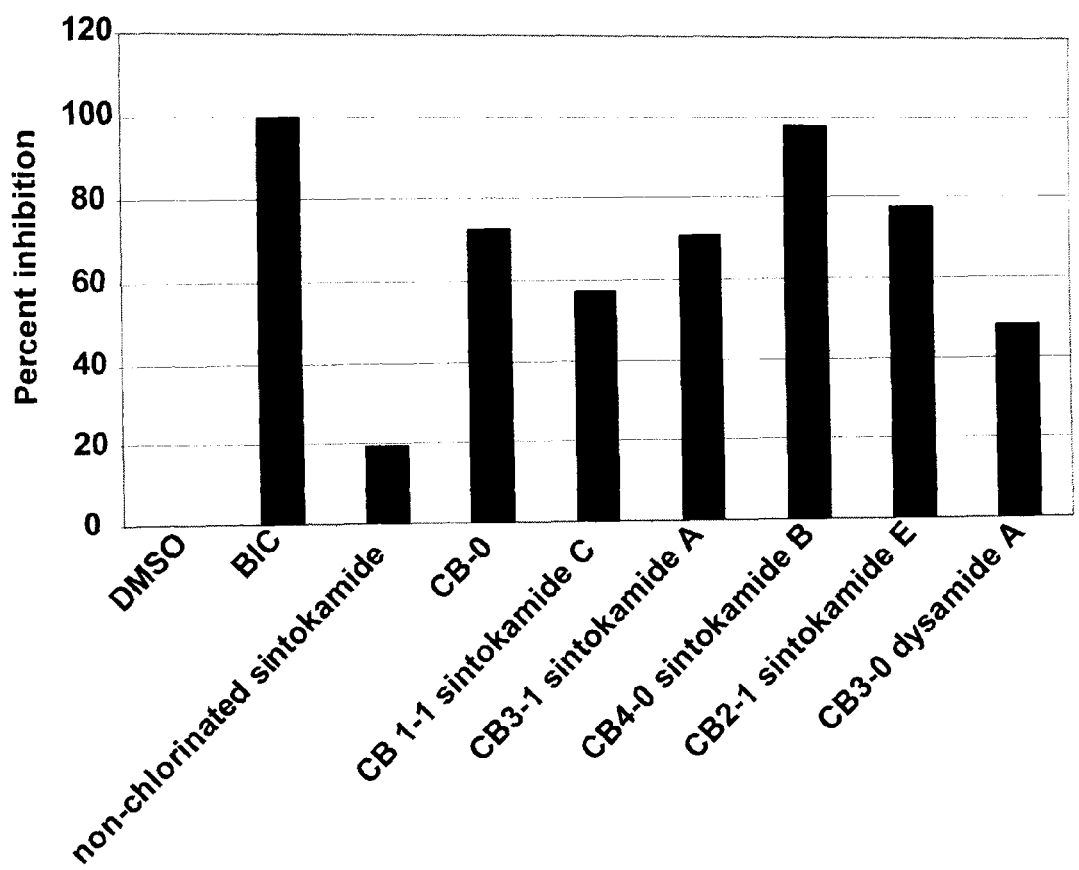
FIG. 5 shows a bar graph demonstrating that inhibition of R1881 induction of PSA (6.1)-luciferase by sintokamides A, B, C and E and Dysimide A. LNCaP cells (8×10$^4$ cells per well) in 12-well plates were seeded in phenol red-free RPMI supplemented with 5% FBS and the next day the cells were transfected with PSA (6.1 kb)-luciferase reporter plasmid (0.5 µg/well), pLuc (1 µg/well) using lipofectin at 2.5 ul per well in serum-free, phenol red-free RPMI. 24 hours after transfaction, the cells were pre-treated for 1 hour with bicalutamide (BIC, 10 µM), non-chlorinated sintokamide (10 µM), or 5 µg/ml of CB-0 extract or sintokamides and dysamide A prior to addition of vehicle (DMSO) or R1881 (1 nM). The cells were harvested 24 hours later and analyzed for luciferase activity. The data is normalized to protein that was measured using Bradford assay.

Activation of the endogenous AR was measured in LNCaP human prostate cancer cells by measuring an androgen-responsive reporter containing androgen response elements (AREs). The PSA (6.1 kb)-luciferase reporter gene construct contains several well-characterized AREs and is induced by androgen. LNCaP cells were maintained as monolayers, were transfected with PSA-luciferase and were used to screen the crude extract (CB-0) prepared from marine sponge as well as purified sintokamides and dysamides (CB3.0 (Dysamide A), CB2.1 (Sintokamide E), CB1.1 (Sintokamide C), CB3.1 (Sintokamide A), and CB4.0 (Sintokamide B) as well as a non-chlorinated sintokamide. The synthetic androgen R1881 (1 nM) induced PSA-luciferase activity by approximately 6-fold. The antiandrogen bicalutamide (BIC) blocked this induction by 100% (see FIG. 5). The partially purified extract CB-0 strongly inhibited androgen-induced activity. The non-chlorinated sintokamide had some activity as did all purified sintokamides and dysamide A. This data supports the conclusion that sintokamides and dysamides have inhibitory effects on PSA expression is at the transcriptional level.

Example 6

Sintokamide A (CB3.1) Reduced Tumor Growth of LNCaP Xenografts

The subcutaneous xenograft model was used to test whether sintokamides that inhibit activation of the androgen receptor in vitro have any effect on these tumors. CB3.1 was tested in vivo using the LNCaP subcutaneous xenograft model. In vivo experiments were done to provide information relevant to toxicity and whether CB3.1 had an effect on tumor growth and progression to androgen independence. LNCaP human prostate cancer cells express endogenous androgen receptor (AR) and prostate-specific antigen (PSA), and progress to androgen independence in castrated hosts. LNCaP cells ($10^6$/ml) were implanted subcutaneously into NOD-SCID male mice that were at least 8 weeks in age. The cells were suspended in 75 µl of RPMI medium 1640 (5% FBS) with 75 µl of Matrigel and injected into the flank region of the host under anesthesia. LNCaP cells were implanted subcutaneously into NOD-SCID male mice and the animals were castrated when the tumors were approximately 100 $mm^3$ (mean=123.3.1±27.4 $mm^3$; n=18) and randomized into two groups. One week after castration the animals were treated every 3 days with an intratumoral dose of 30 mg/kg body weight of CB3.1 or matching volume of vehicle (control, DMSO). CB3.1 showed a reduction of tumor volume (see FIG. 6). Fifteen days after the first injection of CB3.1, the tumors were 111.81%±38.12 the tumor volume on the day of the $1^{st}$ injection. While 15 days after injection of DMSO, the tumors were 180.27%±111.67 the tumor volume on the day of the $1^{st}$ injection. Serum PSA provides an indication of prognosis. For animals receiving CB3.1, serum PSA was 98.47%±170.51 on day 15 after the $1^{st}$ injection. DMSO-treated animals had a doubling of serum PSA at day 15 after the first injection (i.e., 203.73%±315.63). Tumor volume and serum PSA values were consistent with CB3.1 reducing tumor burden and serum PSA compared to vehicle-treated animals. No change in animal body weight was detected upon the duration of the experiment (start: 24.6±1.1 grams; finish: 25.0±1.4 grams) indicating that CB3.1 is not generally toxic to the animals.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention.

What is claimed is:

1. A compound of the Formula (A):

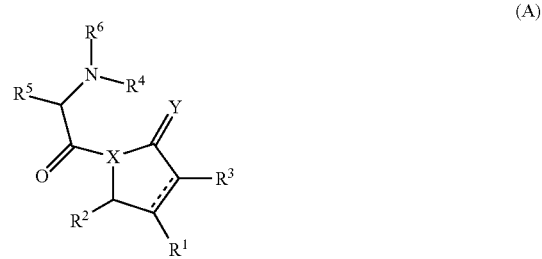

or a salt thereof, wherein:

X is C or N;

Y is O or S;

$R^1$ is H, OH, J, OJ, SJ, or NJJ', wherein J and J' are each independently a one to ten carbon linear, branched, non-aromatic cyclic, or aromatic or partially aromatic cyclic, saturated or unsaturated, optionally substituted alkyl group, wherein the optional substituent is selected from one or more of: oxo, COOH, COOR, $CONH_2$, CONHR, $CONR_2$, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is a linear, or branched saturated and unsubstituted $C_1$-$C_{10}$ alkyl;

$R^2$ is H, an amino acid side chain or a two to ten carbon linear, branched, or non-aromatic cyclic, saturated or unsaturated, optionally substituted alkyl group, wherein the optional substituent is selected from one or more of: oxo, COOH, COOR, $CONH_2$, CONHR, $CONR_2$, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is a linear, or branched saturated and unsubstituted $C_1$-$C_{10}$ alkyl, provided that $R^2$ is not a proline or phenylalanine side chain;

$R^3$ is H, OH, OG, SG, NGG' or a one to ten carbon linear, branched, or non-aromatic cyclic, or aromatic or partially aromatic cyclic, saturated or unsaturated, optionally substituted alkyl group, wherein G and G' are each independently a one to ten carbon linear, branched, non-aromatic cyclic, or aromatic cyclic, saturated or unsaturated, optionally substituted alkyl group and wherein the optional substituent is selected from one or more of: oxo, COOH, OH, COOR, $CONH_2$, CONHR, $CONR_2$, R, F, Cl, Br, I, $NH_2$, CN, SH, $SO_3H$, and $NO_2$, wherein R is an unsubstituted $C_1$-$C_{10}$ alkyl; and $R^4$ and $R^6$ are each independently H, an amino acid side chain or a one to ten carbon linear, branched, aromatic or partially aromatic cyclic, or non-aromatic cyclic, saturated or unsaturated, optionally substituted alkyl group, wherein the optional substituent is selected from one or more of: oxo, COOH, OH, OR, R, F, Cl, Br, I, $NH_2$, NHR, $NR_2$, CN, SH, SR, $SO_3H$, $SO_3R$, $SO_2R$, $OSO_3R$, and $NO_2$, and wherein R is an unsubstituted $C_1$-$C_{10}$ alkyl, provided that both $R^4$ and $R^6$ are not H and provided that neither $R^4$ or $R^6$ are:

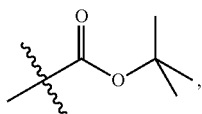

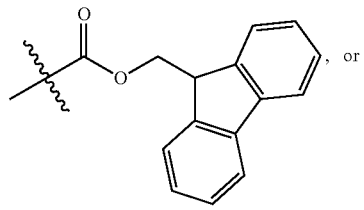

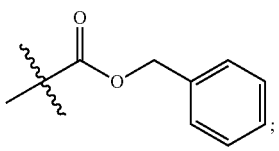

and provided that neither $R^4$ or $R^6$ is a proline side chain;

$R^5$ is H, an amino acid side chain or a one to ten carbon linear, branched, or non-aromatic cyclic, saturated or unsaturated, optionally substituted alkyl group, wherein the optional substituent is selected from one or more of: oxo, COOH, CONH$_2$, OH, F, Cl, Br, I, NH$_2$, SO$_3$H, and NO$_2$, provided that $R^5$ is not a proline or phenylalanine side chain; and ====== is a double bond;

and provided that the compound is not:

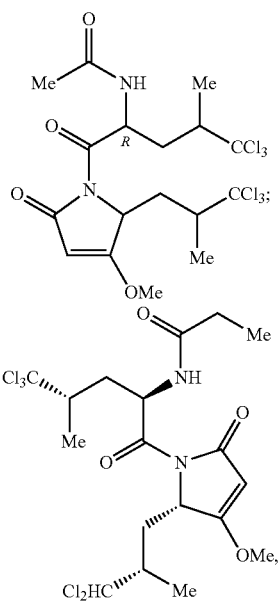

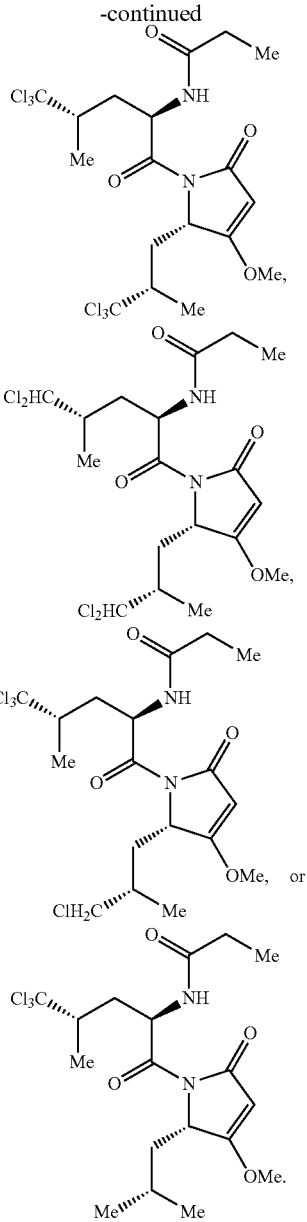

2. A compound having the following Formula (B):

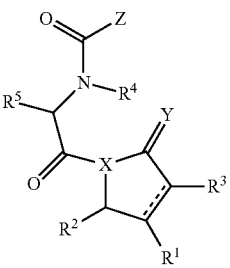

(B)

or a salt thereof, wherein:

X is C or N;

Y is O or S;

R[1] is H, OH, J, OJ, SJ, or NJJ', wherein J and J' are each independently a one to ten carbon linear, branched, non-aromatic cyclic, or aromatic cyclic, saturated or unsaturated, optionally substituted alkyl group, wherein the optional substituent is selected from one or more of: oxo, COOH, OH, F, Cl, Br, I, $NH_2$, CN, SH, $SO_3H$, and $NO_2$;

R[2] is H or a two to ten carbon linear, branched, or non-aromatic cyclic, saturated or unsaturated, optionally substituted alkyl group, wherein the optional substituent is selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is a linear, or branched saturated and unsubstituted C1-C10 alkyl;

R[3] is H, OH, OG, SG, NGG' or a one to ten carbon linear, branched, or non-aromatic cyclic, saturated or unsaturated, optionally substituted alkyl group, wherein G and G' are each independently a one to ten carbon linear, branched, or non-aromatic cyclic, saturated or unsaturated alkyl group and wherein the optional substituent is selected from one or more of: oxo, COOH, OH, F, Cl, Br, I, $NH_2$, CN, SH, $SO_3H$, and $NO_2$; and R[4] is H or a one to ten carbon linear, branched, aromatic cyclic, or non-aromatic cyclic, saturated or unsaturated, optionally substituted alkyl group, wherein the optional substituent is selected from one or more of: oxo, COOH, OH, OR, R, F, Cl, Br, I, $NH_2$, NHR, $NR_2$, CN, SH, SR, $SO_3H$, $SO_3R$, $SO_2R$, $OSO_3R$, and $NO_2$, and wherein R is an unsubstituted $C_1$-$C_{10}$ alkyl, provided that R[4] is not:

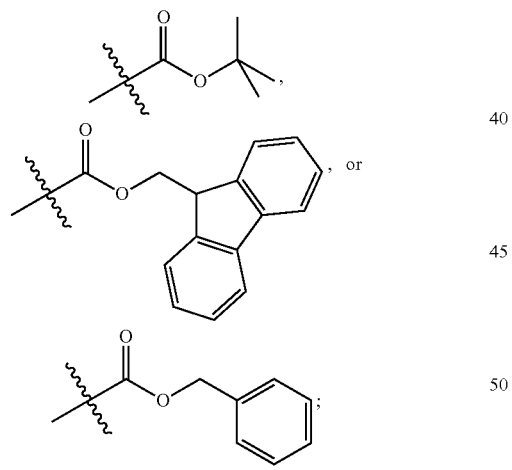

R[5] is H or a one to ten carbon linear, branched, or non-aromatic cyclic, saturated or unsaturated, optionally substituted alkyl group, wherein the optional substituent is selected from one or more of: oxo, COOH, OH, F, Cl, Br, I, $NH_2$, $SO_3H$, and $NO_2$;

Z is an optionally substituted Bu, Pr or Et, wherein the optional substituent is selected from one or more of: oxo, COOH, OH, F, Cl, Br, I, $NH_2$, $SO_3H$, and $NO_2$; and ====== is a single bond or a double bond, provided that the compound is not,

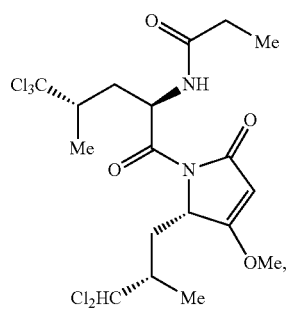

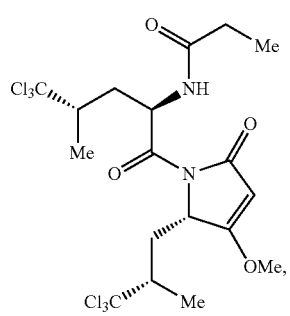

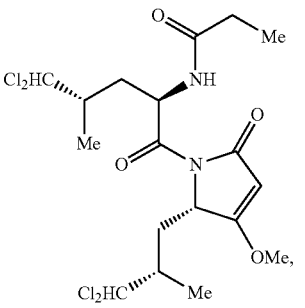

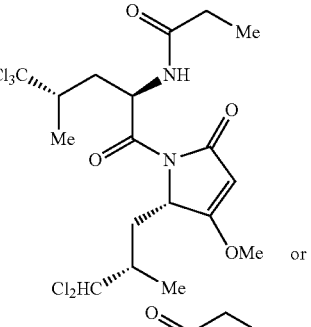 or

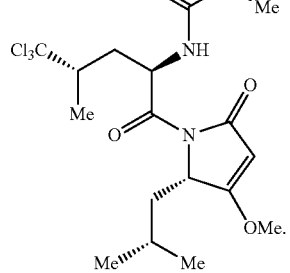

3. The compound of claim 1, wherein R[3] is H, OH, OG, or a one to ten carbon linear, or branched, saturated or unsaturated, optionally substituted alkyl group, wherein G is a one to ten carbon linear, or branched, saturated or unsaturated alkyl group and wherein the optional substituent is selected from one or more of: oxo, COOH, OH, F, Cl, Br, I, NH$_2$, CN, SH, SO$_3$H, and NO$_2$.

4. The compound of claim 1, wherein R$^3$ is H, OH, OBu, OPr, OEt, or OMe.

5. The compound of claim 1, wherein R$^1$ is H, OH, J, or OJ, wherein J is a one to ten carbon linear, branched, non-aromatic cyclic, or aromatic cyclic, saturated or unsaturated, optionally substituted alkyl group, wherein the optional substituent is selected from one or more of: oxo, COOH, OH, F, Cl, Br, I, NH$_2$, and NO$_2$.

6. The compound of claim 1, wherein R$^1$ is H, OH, J, or OJ, wherein J is a one to four carbon linear, or branched, saturated or unsaturated, optionally substituted alkyl group, wherein the optional substituent is selected from one or more of: oxo, COOH, OH, F, Cl, Br, I, and NH$_2$.

7. The compound of claim 1, wherein R$^1$ is H, OH, OBu, OPr, OEt, OMe, Bu, Pr, Et, or Me.

8. The compound of claim 1, wherein R$^1$ is OMe.

9. The compound of claim 2, wherein ===== is a double bond.

10. The compound of claim 1, wherein R$^2$ is H or a two to ten carbon linear, or branched, saturated or unsaturated, optionally substituted alkyl group, wherein the optional substituent is selected from one or more of: oxo, COOH, OH, F, Cl, Br, I, NH$_2$, and NO$_2$.

11. The compound of claim 1, wherein R$^2$ is H or a two to four carbon linear, or branched, saturated optionally substituted alkyl group, wherein the optional substituent is selected from one or more of: oxo, OH, F, Cl, Br, I, and NH$_2$.

12. The compound of claim 1, wherein R$^4$ is H or a one to ten carbon linear, or branched, saturated or unsaturated, optionally substituted alkyl group, wherein the optional substituent is selected from one or more of: oxo, COOH, OH, F, Cl, Br, I, NH$_2$, SH, SO$_3$H, and NO$_2$.

13. The compound of claim 1, wherein R$^4$ is H or a one to four carbon linear, or branched, saturated optionally substituted alkyl group, wherein the optional substituent is selected from one or more of: oxo, OH, F, Cl, Br, I, and NH$_2$.

14. The compound of claim 1, wherein R$^5$ is H or a one to ten carbon linear, or branched, saturated or unsaturated, optionally substituted alkyl group, wherein the optional substituent is selected from one or more of: oxo, COOH, OH, F, Cl, Br, I, NH$_2$, SO$_3$H, and NO$_2$.

15. The compound of claim 1, wherein R$^5$ is H or a one to four carbon linear, or branched, saturated optionally substituted alkyl group, wherein the optional substituent is selected from one or more of: oxo, OH, F, Cl, Br, I, and NH$_2$.

16. The compound of claim 1, wherein X is N.

17. The compound of claim 1, wherein Y is O.

18. The compound of claim 2, wherein Z is an optionally substituted Bu, Pr or Et, wherein the optional substituent is selected from one or more of: oxo, OH, F, Cl, Br, and I.

19. The compound of claim 2, wherein Z is an optionally substituted Bu, Pr or Et, wherein the optional substituent is selected from one or more of: F, Cl, Br, and I.

20. The compound of claim 1, wherein the compound has the following Formula (C):

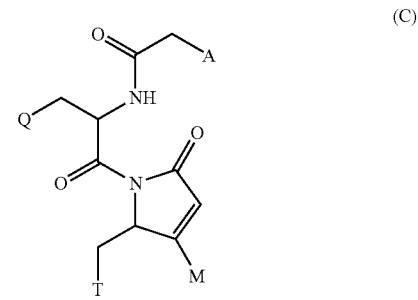

or a salt thereof, wherein:

A is Bu, Pr, Et, or Me;

M is H, OH, OBu, OPr, OEt, OMe, Bu, Pr, Et, or Me;

T is

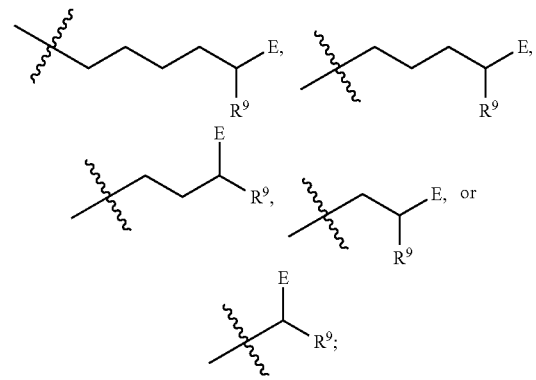

E is Bu, Pr, Et, or Me;

Q is

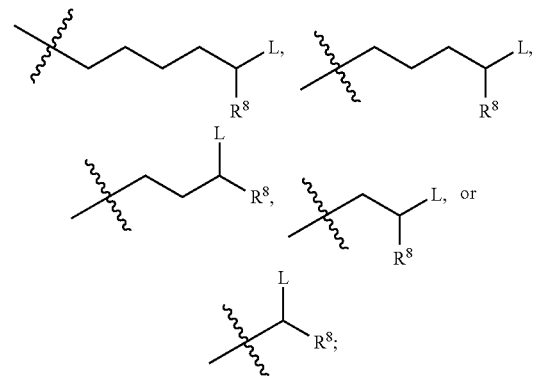

L is Bu, Pr, Et, or Me;

R$^8$ is Cl$_3$C, Cl$_2$HC, ClH$_2$C, Bu, Pr, Et, or Me; and

R$^9$ is Cl$_3$C, Cl$_2$HC, ClH$_2$C, Bu, Pr, Et, or Me;

and wherein,

A, T, E, Q, and L are optionally substituted, wherein the optional substituent is selected from one or more of: oxo, COOH, OH, F, Cl, Br, I, NH$_2$, SO$_3$H, and NO$_2$.

21. The compound of claim 1, wherein the compound has the following Formula (D):

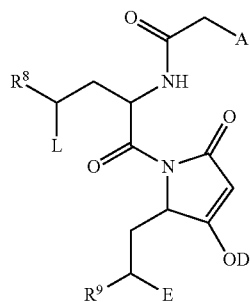
(D)

or a salt thereof, wherein:
A is Bu, Pr, Et, or Me;
D is Bu, Pr, Et, or Me;
E is Bu, Pr, Et, or Me;
L is Bu, Pr, Et, or Me;
$R^8$ is $Cl_3C$, $Cl_2HC$, $ClH_2C$, Bu, Pr, Et, or Me; and
$R^9$ is $Cl_3C$, $Cl_2HC$, $ClH_2C$, Bu, Pr, Et, or Me.

22. The compound of claim 1, wherein the compound has the following Formula (E):

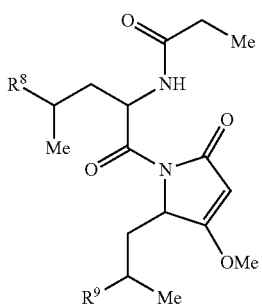
(E)

or a salt thereof, wherein:
$R^8$ is $Cl_3C$, $Cl_2HC$, $ClH_2C$, Et, or Me; and
$R^9$ is $Cl_3C$, $Cl_2HC$, $ClH_2C$, Et, or Me.

23. The compound of claim 1, wherein the compound has one of the following structures:

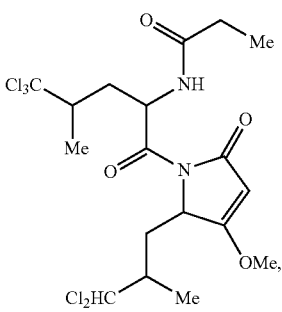

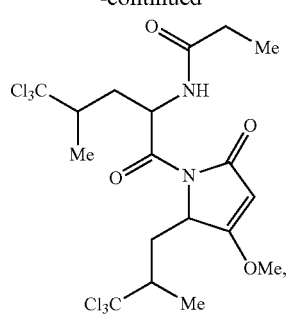

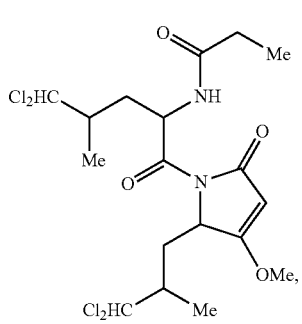

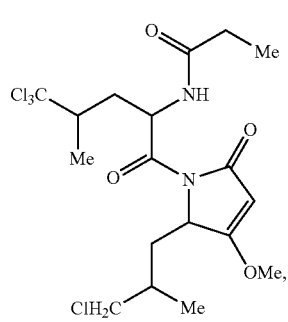

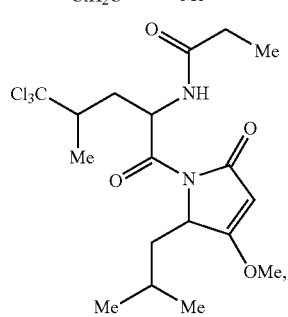

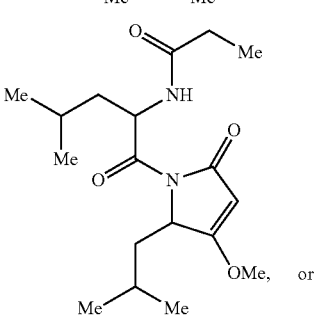

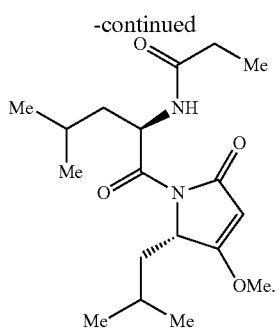

24. A method for modulating androgen receptor (AR) activity, the method comprising administering to a mammalian cell a compound having a structure of Formula A:

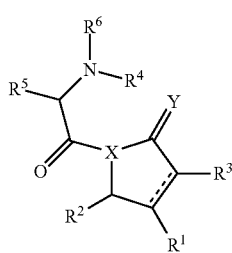

(A)

or a salt thereof, wherein:
X is C or N;
Y is O or S;
$R^1$ is H, OH, J, OJ, SJ, or NJJ', wherein J and J' are each independently a one to ten carbon linear, branched, non-aromatic cyclic, or aromatic cyclic, saturated or unsaturated, optionally substituted alkyl group, wherein the optional substituent is selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is an linear, or branched saturated and unsubstituted $C_1$-$C_{10}$ alkyl;
$R^2$ is H or a one to ten carbon linear, branched, or non-aromatic cyclic, saturated or unsaturated, optionally substituted alkyl group, wherein the optional substituent is selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is an linear, or branched saturated and unsubstituted $C_1$-$C_{10}$ alkyl;
$R^3$ is H, OH, OG, SG, NGG' or a one to ten carbon linear, branched, or non-aromatic cyclic, saturated or unsaturated, optionally substituted alkyl group, wherein G and G' are each independently a one to ten carbon linear, branched, or non-aromatic cyclic, saturated or unsaturated, optionally substituted alkyl group and wherein the optional substituent is selected from one or more of: oxo, COOH, OH, F, Cl, Br, I, $NH_2$, CN, SH, $SO_3H$, and $NO_2$;
$R^4$ and $R^6$ are each independently H or a one to ten carbon linear, branched, aromatic cyclic, or non-aromatic cyclic, saturated or unsaturated, optionally substituted alkyl group, wherein the optional substituent is selected from one or more of: oxo, COOH, OH, OR, R, F, Cl, Br, I, $NH_2$, NHR, $NR_2$, CN, SH, SR, $SO_3H$, $SO_3R$, $SO_2R$, $OSO_3R$, and $NO_2$, and wherein R is a linear, or branched saturated and unsubstituted $C_1$-$C_{10}$ alkyl;
$R^5$ is H or a one to ten carbon linear, branched, or non-aromatic cyclic, saturated or unsaturated, optionally substituted alkyl group, wherein the optional substituent is selected from one or more of: oxo, COOH, OH, F, Cl, Br, I, $NH_2$, $SO_3H$, and $NO_2$; and
===== is a single bond or a double bond.

25. A pharmaceutical composition comprising a pharmaceutically acceptable and sterile excipient and a compound having the following structure (A);

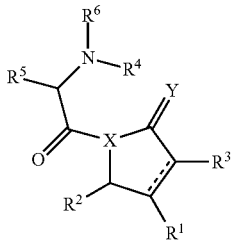

(A)

or a salt thereof, wherein;
X is C or N;
Y is O or S;
$R^1$ is H, OH, J, OJ, SJ, or NJJ', wherein J and J' are each independently a one to ten carbon linear, branched, non-aromatic cyclic, or aromatic or partially aromatic cyclic, saturated or unsaturated, optionally substituted alkyl group, wherein the optional substituent is selected from one or more of: oxo, COOH, COOR, $CONH_2$, CONHR, $CONR_2$, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is an linear, or branched saturated and unsubstituted $C_1$-$C_{10}$ alkyl;
$R^2$ is H, an amino acid side chain or a two to ten carbon linear, branched, or non-aromatic cyclic, saturated or unsaturated, optionally substituted alkyl group, wherein the optional substituent is selected from one or more of: oxo, COOH, COOR, $CONH_2$, CONHR, $CONR_2$, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is an linear, or branched saturated and unsubstituted $C_1$-$C_{10}$ alkyl, provided that $R^2$ is not a proline or phenylalanine side chain;
$R^3$ is H, OH, OG, SG, NGG' or a one to ten carbon linear, branched, or non-aromatic cyclic, or aromatic or partially aromatic cyclic, saturated or unsaturated, optionally substituted alkyl group, wherein G and G' are each independently a one to ten carbon linear, branched, non-aromatic cyclic, or aromatic cyclic, saturated or unsaturated, optionally substituted alkyl group and wherein the optional substituent is selected from one or more of: oxo, COOH, OH, COOR, $CONH_2$, CONHR, $CONR_2$, R, F, Cl, Br, I, $NH_2$, CN, SH, $SO_3H$, and $NO_2$, wherein R is an unsubstituted $C_1$-$C_{10}$ alkyl; and
$R^4$ and $R^6$ are each independently H, an amino acid side chain or a one to ten carbon linear, branched, aromatic or partially aromatic cyclic, or non-aromatic cyclic, saturated or unsaturated, optionally substituted alkyl group, wherein the optional substituent is selected from one or more of: oxo, COOH, OH, OR, R, F, Cl, Br, I, $NH_2$, NHR, $NR_2$, CN, SH, SR, $SO_3H$, $SO_3R$, $SO_2R$, $OSO_3R$, and $NO_2$, and wherein R is an unsubstituted $C_1$-$C_{10}$ alkyl, provided that both $R^4$ and $R^6$ are not H and provided that neither $R^4$ and $R^6$ are:

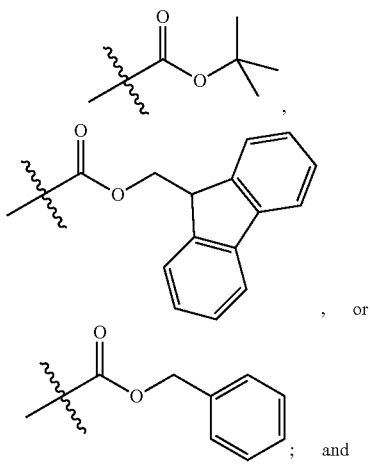

, or

; and provided that neither $R^6$ or $R^6$ is a proline side chain;

$R^5$ is H, an amino acid side chain or a one to ten carbon linear, branched, or non-aromatic cyclic, saturated or unsaturated, optionally substituted alkyl group, wherein the optional substituent is selected from one or more of: oxo, COOH, CONH$_2$, OH, F, Cl, Br, I, NH$_2$, SO$_3$H, and NO$_2$, provided that $R^5$ is not a proline or phenylalanine side chain; and --------- is a double bond.

26. The compound of claim 2, wherein $R^3$ is H, OH, OG, or a one to ten carbon linear, or branched, saturated or unsaturated, optionally substituted alkyl group, wherein G is a one to ten carbon linear, or branched, saturated or unsaturated alkyl group and wherein the optional substituent is selected from one or more of: oxo, COOH, OH, F, Cl, Br, I, NH$_2$, CN, SH, SO$_3$H, and NO$_2$.

27. The compound of claim 2, wherein $R^3$ is H, OH, OBu, OPr, OEt, or OMe.

28. The compound of claim 2, wherein $R^1$ is H, OH, J, or OJ, wherein J is a one to ten carbon linear, branched, non-aromatic cyclic, or aromatic cyclic, saturated or unsaturated, optionally substituted alkyl group, wherein the optional substituent is selected from one or more of: oxo, COOH, OH, F, Cl, Br, I, NH$_2$, and NO$_2$.

29. The compound of claim 2, wherein $R^1$ is H, OH, J, or OJ, wherein J is a one to four carbon linear, or branched, saturated or unsaturated, optionally substituted alkyl group, wherein the optional substituent is selected from one or more of: oxo, COOH, OH, F, Cl, Br, I, and NH$_2$.

30. The compound of claim 2, wherein $R^1$ is H, OH, OBu, OPr, OEt, OMe, Bu, Pr, Et, or Me.

31. The compound of claim 2, wherein $R^1$ is OMe.

32. The compound of claim 2, wherein $R^2$ is H or a two to ten carbon linear, or branched, saturated or unsaturated, optionally substituted alkyl group, wherein the optional substituent is selected from one or more of: oxo, COOH, OH, F, Cl, Br, I, NH$_2$, and NO$_2$.

33. The compound of claim 2, wherein $R^2$ is H or a two to four carbon linear, or branched, saturated optionally substituted alkyl group, wherein the optional substituent is selected from one or more of: oxo, OH, F, Cl, Br, I, and NH$_2$.

34. The compound of claim 2, wherein $R^4$ is H or a one to ten carbon linear, or branched, saturated or unsaturated, optionally substituted alkyl group, wherein the optional substituent is selected from one or more of: oxo, COOH, OH, F, Cl, Br, I, NH$_2$, SH, SO$_3$H, and NO$_2$.

35. The compound of claim 2, wherein $R^4$ is H or a one to four carbon linear, or branched, saturated optionally substituted alkyl group, wherein the optional substituent is selected from one or more of: oxo, OH, F, Cl, Br, I, and NH$_2$.

36. The compound of claim 2, wherein $R^5$ is H or a one to ten carbon linear, or branched, saturated or unsaturated, optionally substituted alkyl group, wherein the optional substituent is selected from one or more of: oxo, COOH, OH, F, Cl, Br, I, NH$_2$, SO$_3$H, and NO$_2$.

37. The compound of claim 2, wherein $R^5$ is H or a one to four carbon linear, or branched, saturated optionally substituted alkyl group, wherein the optional substituent is selected from one or more of: oxo, OH, F, Cl, Br, I, and NH$_2$.

38. The compound of claim 2, wherein X is N.

39. The compound of claim 2, wherein Y is O.

40. A pharmaceutical composition comprising a pharmaceutically acceptable and sterile excipient and a compound having the following structure (B):

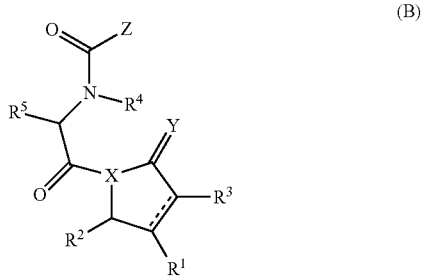

(B)

or a salt thereof, wherein:

X is C or N;

Y is O or S;

$R^1$ is H, OH, J, OJ, SJ, or NJJ', wherein J and J' are each independently a one to ten carbon linear, branched, non-aromatic cyclic, or aromatic cyclic, saturated or unsaturated, optionally substituted alkyl group, wherein the optional substituent is selected from one or more of: oxo, COOH, OH, F, Cl, Br, I, NH$_2$, CN, SH, SO$_3$H, and NO$_2$;

$R^2$ is H or a two to ten carbon linear, branched, or non-aromatic cyclic, saturated or unsaturated, optionally substituted alkyl group, wherein the optional substituent is selected from one or more of: oxo, COOH, R, OH, OR, F, Cl, Br, I, NH$_2$, NHR, NR$_2$, CN, SH, SR, SO$_3$H, SO$_3$R, SO$_2$R, OSO$_3$R, and NO$_2$, and wherein R is a linear, or branched saturated and unsubstituted C1-C10 alkyl;

$R^3$ is H, OH, OG, SG, NGG' or a one to ten carbon linear, branched, or non-aromatic cyclic, saturated or unsaturated, optionally substituted alkyl group, wherein G and G' are each independently a one to ten carbon linear, branched, or non-aromatic cyclic, saturated or unsaturated alkyl group and wherein the optional substituent is selected from one or more of: oxo, COOH, OH, F, Cl, Br, I, NH$_2$, CN, SH, SO$_3$H, and NO$_2$; and $R^4$ is H or a one to ten carbon linear, branched, aromatic cyclic, or non-aromatic cyclic, saturated or unsaturated, optionally substituted alkyl group, wherein the optional substituent is selected from one or more of: oxo, COOH, OH, OR, R, F, Cl, Br, I, NH$_2$, NHR, NR$_2$, CN, SH, SR, SO$_3$H, SO$_3$R, SO$_2$R, OSO$_3$R, and NO$_2$, and wherein R is an unsubstituted $C_1$-$C_{10}$ alkyl, provided that $R^4$ is not:

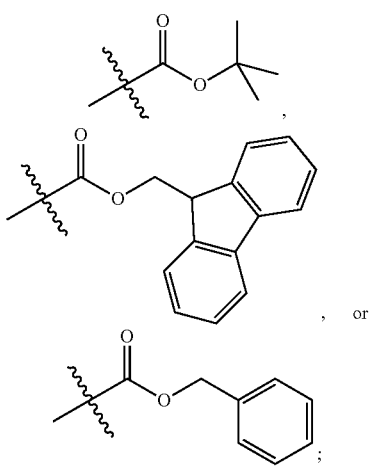

, or

R⁵ is H or a one to ten carbon linear, branched, or non-aromatic cyclic, saturated or unsaturated, optionally substituted alkyl group, wherein the optional substituent is selected from one or more of: oxo, COOH, OH, F, Cl, Br, I, $NH_2$, $SO_3H$, and $NO_2$;

Z is an optionally substituted Bu, Pr or Et, wherein the optional substituent is selected from one or more of: oxo, COOH, OH, F, Cl, Br, I, $NH_2$, $SO_3H$, and $NO_2$; and ===== is a single bond or a double bond.

41. The method of claim 25, wherein the compound has the following Formula (B):

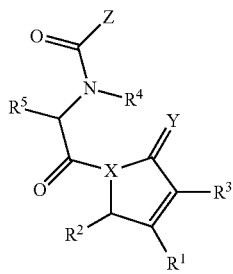

(B)

or a salt thereof, wherein:

X is C or N;
Y is O or S;
$R^1$ is H, OH, J, OJ, SJ, or NJJ', wherein J and J' are reach independently a one to ten carbon linear, branched, non-aromatic cyclic, or aromatic cyclic, saturated or unsaturated, optionally substituted alkyl group, wherein the optional substituent is selected from one or more of: oxo, COOH, OH, F, Cl, Br, I, $NH_2$, CN, SH, $SO_3H$, and $NO_2$;
$R^2$ is H or a one to ten carbon linear, branched, or non-aromatic cyclic, saturated or unsaturated, optionally substituted alkyl group, wherein the optional substituent is selected from one or more of: oxo, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$, and wherein R is a linear, or branched saturated and unsubstituted C1-C10 alkyl;
$R^3$ is H, OH, OG, SG, NGG' or a one to ten carbon linear, branched, or non-aromatic cyclic, saturated or unsaturated, optionally substituted alkyl group, wherein G and G' are each independently a one to ten carbon linear, branched, or non-aromatic cyclic, saturated or unsaturated alkyl group, wherein the optional substituent is selected from one or more of: oxo, COOH, OH, F, Cl, Br, I, $NH_2$, CN, SH, $SO_3H$, and $NO_2$;
$R^4$ is H or a one to ten carbon linear, branched, aromatic cyclic, or non-aromatic cyclic, saturated or unsaturated, optionally substituted alkyl group, wherein the optional substituent is selected from one or more of: oxo, COOH, OH, OR, R, F, Cl, Br, I, $NH_2$, NHR, $NR_2$, CN, SH, SR, $SO_3H$, $SO_3R$, $SO_2R$, $OSO_3R$, and $NO_2$, wherein R is an unsubstituted $C_1$-$C_{10}$ alkyl,
$R^5$ is H or a one to ten carbon linear, branched, or non-aromatic cyclic, saturated or unsaturated, optionally substituted alkyl group, wherein the optional substituent is selected from one or more of: oxo, COOH, OH, F, Cl, Br, I, $NH_2$, $SO_3H$, and $NO_2$;
Z is an optionally substituted Bu, Pr, Et, or Me, wherein the optional substituent is selected from one or more of: oxo, COOH, OH, F, Cl, Br, I, $NH_2$, $SO_3H$, and $NO_2$; and ===== is a double bond.

42. The method of claim 24, wherein ===== is a double bond.

43. The method of claim 24, wherein the compound has the following Formula (C):

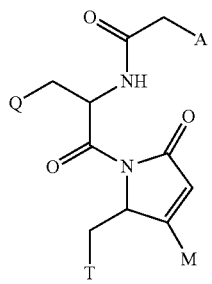

(C)

or a salt thereof, wherein:
A is Bu, Pr, Et, or Me;
M is H, OH, OBu, OPr, OEt, OMe, Bu, Pr, Et, or Me;
T

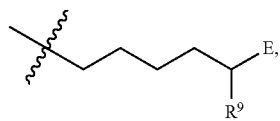

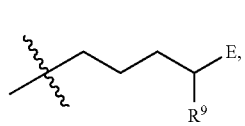 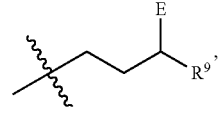

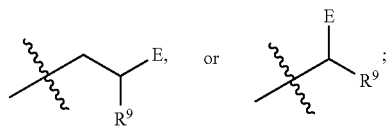

E is Bu, Pr, Et, or Me:
Q is

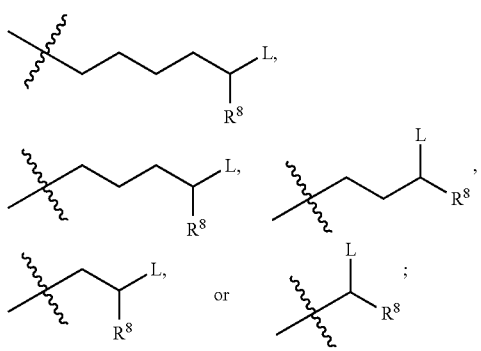

L is Bu, Pr, Et, or Me;
R$^8$ is Cl$_3$C, Cl$_2$HC, ClH$_2$C, Bu, Pr, Et, or Me; and
R$^9$ is Cl$_3$C, Cl$_2$HC, ClH$_2$C, Bu, Pr, Et, or Me;
and wherein,
A, T, E, Q, and L are optionally substituted, wherein the optional substituent is selected from one or more of: oxo, COOH, OH, F, Cl, Br, I, NH$_2$, SO$_3$H, and NO$_2$.

44. The method of claim 24, wherein the compound has the following Formula (D):

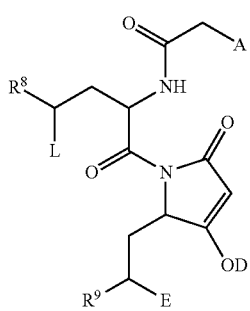
(D)

or a salt thereof, wherein:
A is Bu, Pr, Et, or Me;
D is Bu, Pr, Et, or Me;
E is Bu, Pr, Et, or Me;
L is Bu, Pr, Et, or Me;
R$^8$ is Cl$_3$C, Cl$_2$HC, ClH$_2$C, Bu, Pr, Et, or Me; and
R$^9$ is Cl$_3$C, Cl$_2$HC, ClH$_2$C, Bu, Pr, Et, or Me.

45. The method of claim 24, wherein the compound has the following Formula (E):

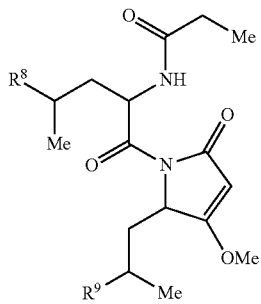
(E)

or a salt thereof, wherein:

R$^8$ is Cl$_3$C, Cl$_2$HC, ClH$_2$C, Et, or Me; and
R$^9$ is Cl$_3$C, Cl$_2$HC, ClH$_2$C, Et, or Me.

46. The method of claim 24, wherein the compound has one of the following structures:

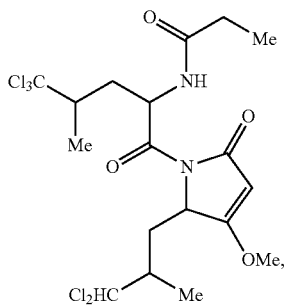

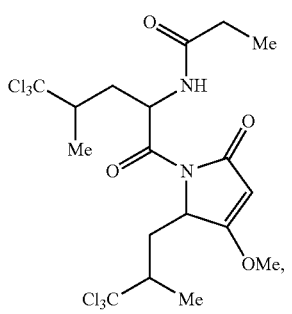

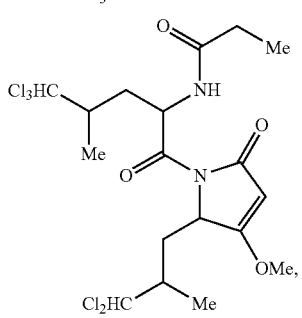

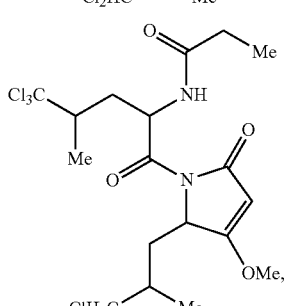

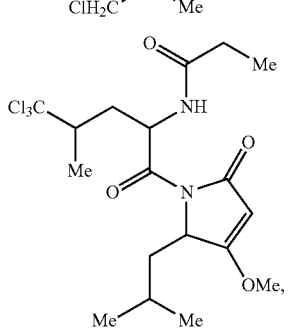

-continued

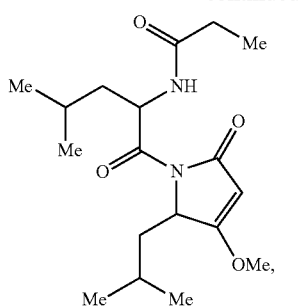

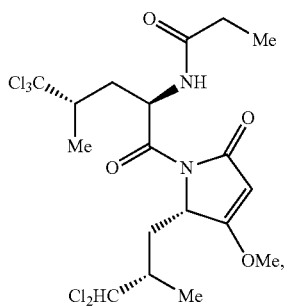

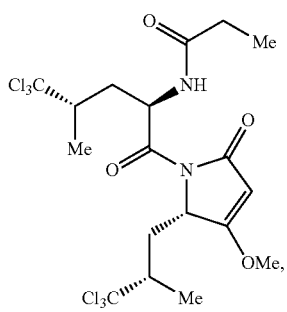

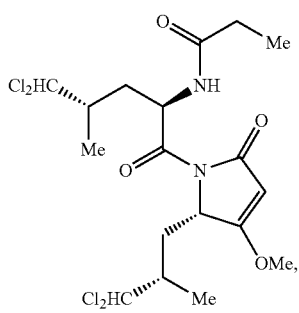

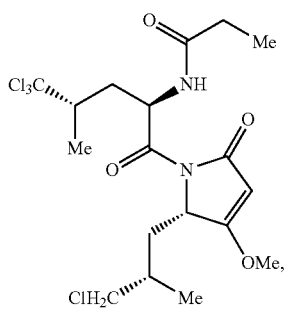

-continued

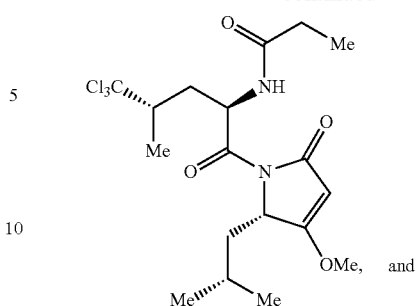

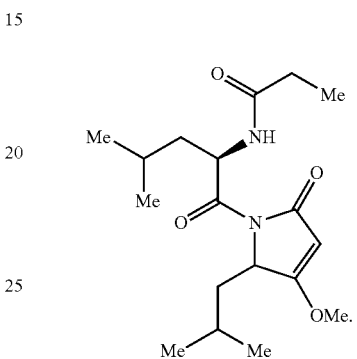

47. The method of claim 24, wherein the modulation of AR activity is in a human cell.

48. The method of claim 24, wherein the modulation of AR activity is for the inhibition of AR N-terminal domain (NTD) activity.

49. The method of claim 24, wherein the modulation of AR activity is for the prevention or treatment of prostate cancer, breast cancer, ovarian cancer, endometrial cancer, hair loss, acne, hirsutism, ovarian cysts, polycystic ovary disease, precocious puberty, or age-related macular degeneration.

50. The method of claim 49, wherein the modulation of AR activity is for the prevention or treatment of prostate cancer.

51. The method of claim 50, wherein the prostate cancer is androgen-independent prostate cancer.

52. The method of claim 50, wherein the prostate cancer is androgen-dependent prostate cancer.

53. The pharmaceutical composition of claim 25, wherein the compound is not:

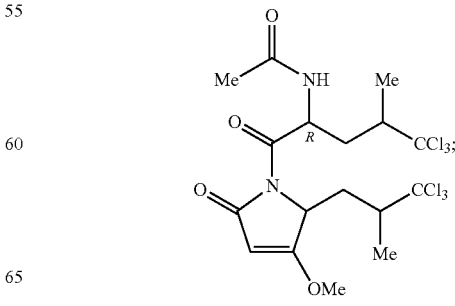

-continued
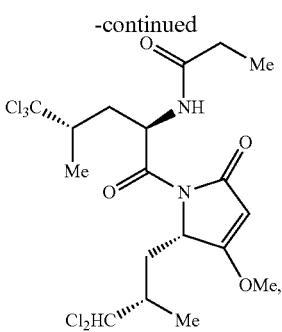
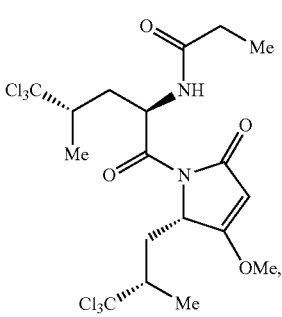
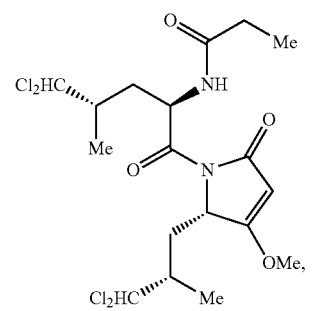
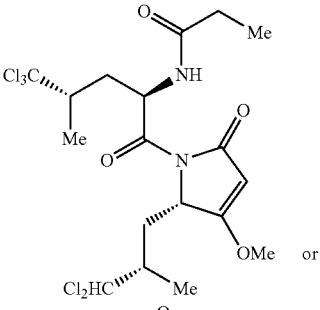
or
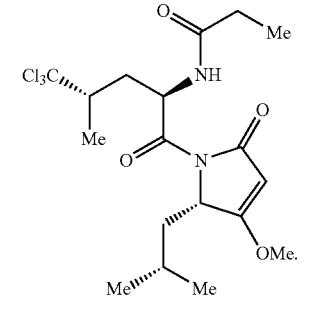
54. The pharmaceutical composition of claim 40, wherein the compound is not:
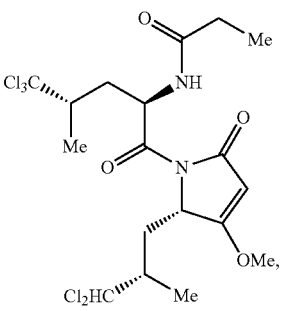
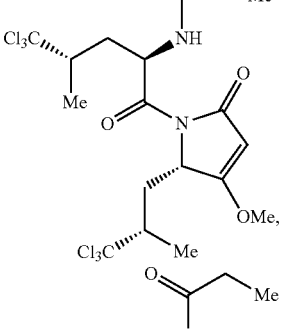
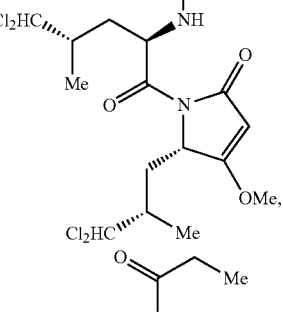
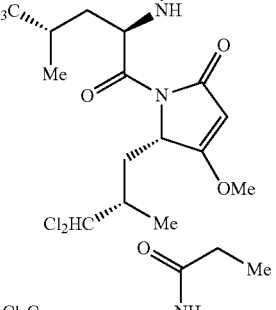
or
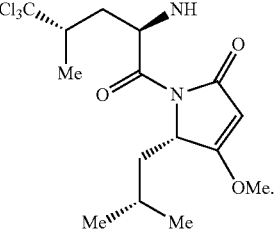
* * * * *

UNITED STATES PATENT AND TRADEMARK OFFICE
CERTIFICATE OF CORRECTION

PATENT NO. : 9,487,479 B2
APPLICATION NO. : 12/999035
DATED : November 8, 2016
INVENTOR(S) : Marianne D. Sadar et al.

It is certified that error appears in the above-identified patent and that said Letters Patent is hereby corrected as shown below:

In the Claims

In Claim 2, Column 70, Lines 40-52, please replace

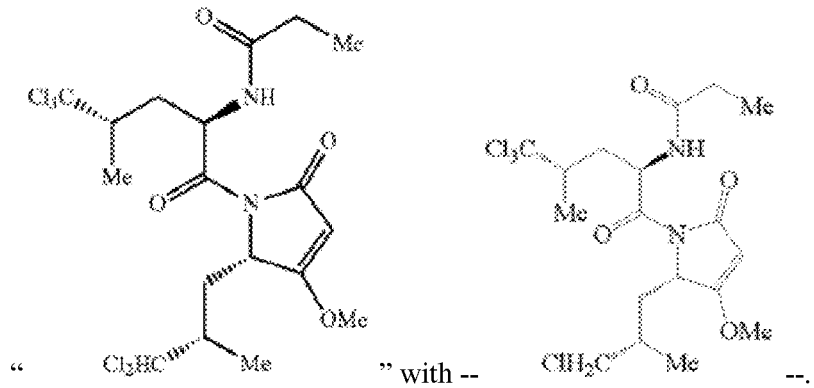

" with --  --.

In Claim 41, Column 79, Line 31, please replace "claim 25" with -- claim 24 --.

In Claim 46, Column 82, Lines 31-43, please replace

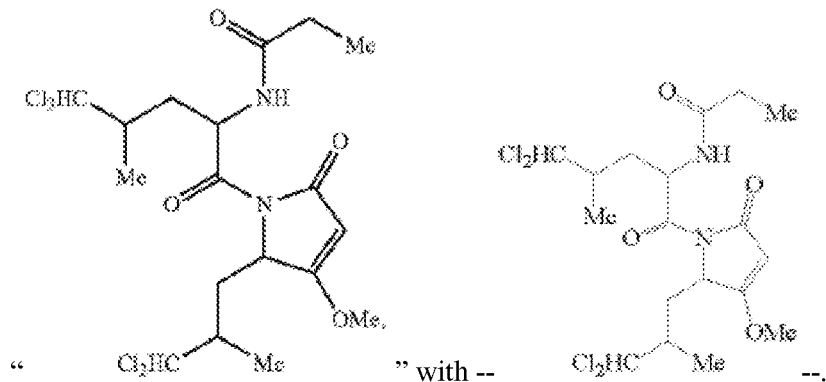

" with --  --.

Signed and Sealed this
Twentieth Day of February, 2018

Andrei Iancu
*Director of the United States Patent and Trademark Office*

CERTIFICATE OF CORRECTION (continued)
U.S. Pat. No. 9,487,479 B2

Page 2 of 2

In Claim 53, Column 85, Lines 41-52, please replace

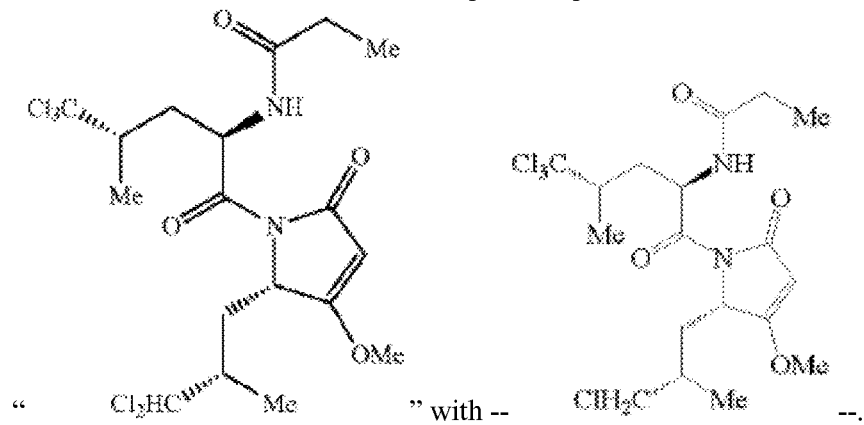

" with --    --.

In Claim 54, Column 86, Lines 38-50, please replace

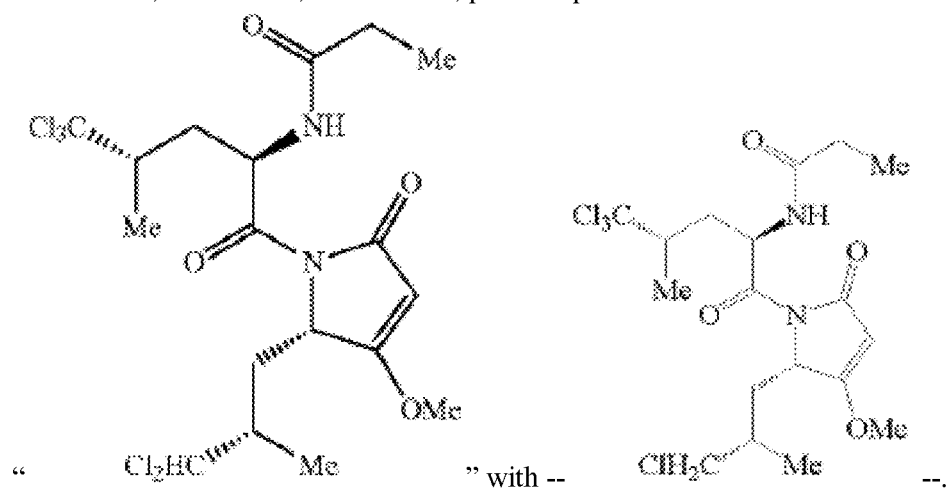

" with --    --.

UNITED STATES PATENT AND TRADEMARK OFFICE
CERTIFICATE OF CORRECTION

| | |
|---|---|
| PATENT NO. | : 9,487,479 B2 |
| APPLICATION NO. | : 12/999035 |
| DATED | : November 8, 2016 |
| INVENTOR(S) | : Marianne D. Sadar et al. |

It is certified that error appears in the above-identified patent and that said Letters Patent is hereby corrected as shown below:

In the Specification

At Column 1, Lines 19-23:
"This invention was made in part with government support under grant number W81XWH-05-1-0058 (PC040768), awarded by U.S. Army Medical Research and Materiel Command. The United States government may have certain rights in the invention."

Should read:
-- This invention was made with government support under W81XWH-05-1-0058 awarded by the Medical Research and Development Command. The government has certain rights in the invention. --

Signed and Sealed this
Nineteenth Day of March, 2024

Katherine Kelly Vidal
*Director of the United States Patent and Trademark Office*